(12) United States Patent
Fardis

(10) Patent No.: US 11,819,517 B2
(45) Date of Patent: *Nov. 21, 2023

(54) METHODS OF USING TUMOR INFILTRATING LYMPHOCYTES IN DOUBLE-REFRACTORY MELANOMA

(71) Applicant: Iovance Biotherapeutics, Inc., San Carlos, CA (US)

(72) Inventor: Maria Fardis, San Carlos, CA (US)

(73) Assignee: IOVANCE BIOTHERAPEUTICS, INC., San Carlos, CA (US)

(*) Notice: Subject to any disclaimer, the term of this patent is extended or adjusted under 35 U.S.C. 154(b) by 843 days.

This patent is subject to a terminal disclaimer.

(21) Appl. No.: 16/618,039

(22) PCT Filed: Jun. 5, 2018

(86) PCT No.: PCT/US2018/036088
§ 371 (c)(1),
(2) Date: Nov. 27, 2019

(87) PCT Pub. No.: WO2018/226714
PCT Pub. Date: Dec. 13, 2018

(65) Prior Publication Data
US 2021/0145877 A1    May 20, 2021

Related U.S. Application Data

(60) Provisional application No. 62/515,257, filed on Jun. 5, 2017.

(51) Int. Cl.
| | |
|---|---|
| *A61K 35/17* | (2015.01) |
| *A61P 35/04* | (2006.01) |
| *C12N 5/0783* | (2010.01) |
| *C12N 5/078* | (2010.01) |
| *G01N 33/574* | (2006.01) |
| *A61K 35/00* | (2006.01) |

(52) U.S. Cl.
CPC .............. *A61K 35/17* (2013.01); *A61P 35/04* (2018.01); *C12N 5/0634* (2013.01); *C12N 5/0638* (2013.01); *G01N 33/574* (2013.01); *A61K 35/00* (2013.01); *C12N 2501/04* (2013.01); *C12N 2501/2302* (2013.01); *C12N 2501/515* (2013.01); *C12N 2502/30* (2013.01); *G01N 2333/522* (2013.01)

(58) Field of Classification Search
CPC ....... A61K 35/17; A61P 35/04; C12N 5/0638; C12N 2501/04; C12N 2501/2302; C12N 2502/30
USPC .................................................... 424/93.71
See application file for complete search history.

(56) References Cited

U.S. PATENT DOCUMENTS

| | | |
|---|---|---|
| 4,766,106 A | 8/1988 | Katre et al. |
| 4,902,502 A | 2/1990 | Nitecki et al. |
| 5,089,261 A | 2/1992 | Nitecki et al. |
| 5,206,344 A | 4/1993 | Katre et al. |
| 5,928,893 A | 7/1999 | Kang et al. |
| 6,210,669 B1 | 4/2001 | Aruffo et al. |
| 6,303,121 B1 | 10/2001 | Kwon |
| 6,362,325 B1 | 3/2002 | Kwon |
| 6,569,997 B1 | 5/2003 | Kwon |
| 6,706,289 B2 | 3/2004 | Lewis et al. |
| 6,887,673 B2 | 5/2005 | Kunkel et al. |
| 6,905,685 B2 | 6/2005 | Kwon |
| 6,974,863 B2 | 12/2005 | Kwon |
| 7,214,493 B2 | 5/2007 | Kunkel et al. |
| 7,288,638 B2 | 10/2007 | Jure-Kunkel et al. |
| 7,504,101 B2 | 3/2009 | Weinberg |
| 7,550,140 B2 | 6/2009 | Bakker et al. |
| 7,622,444 B2 | 11/2009 | Weinberg |
| 7,696,175 B2 | 4/2010 | Epstein et al. |
| 7,943,743 B2 | 5/2011 | Korman et al. |
| 7,960,515 B2 | 6/2011 | Min et al. |
| 7,961,515 B2 | 6/2011 | Kato et al. |
| 8,008,449 B2 | 8/2011 | Korman et al. |
| 8,034,334 B2 | 10/2011 | Dudley et al. |
| 8,133,983 B2 | 3/2012 | Bakker et al. |
| 8,236,930 B2 | 8/2012 | Hill et al. |
| 8,287,857 B2 | 11/2012 | Dudley et al. |
| 8,337,850 B2 | 12/2012 | Ahrens et al. |
| 8,383,099 B2 | 2/2013 | Dudley et al. |
| 8,450,460 B2 | 5/2013 | Hill et al. |
| 8,809,050 B2 | 8/2014 | Vera et al. |
| 8,821,867 B2 | 9/2014 | Ahrens et al. |
| 8,921,519 B2 | 12/2014 | Hill et al. |
| 8,956,860 B2 | 2/2015 | Vera et al. |
| 8,962,804 B2 | 2/2015 | Williams et al. |
| 9,006,399 B2 | 4/2015 | Liu et al. |

(Continued)

FOREIGN PATENT DOCUMENTS

| | | |
|---|---|---|
| EP | 0672141 B1 | 5/2003 |
| WO | WO 95/12673 | 5/1995 |

(Continued)

OTHER PUBLICATIONS

Merhavi-Shoham et al., "Adoptive Cell Therapy for Metastatic Melanoma," The Cancer Journal, Jan./Feb. 2017, 23(1): 48-53.
Baruch et al., "Adoptive T Cell Therapy: An Overview of Obstacles and Opportunities," Cancer, Jun. 1, 2017, 123(S11), 2154-2162.
Goff et al., "Randomized, Prospective Evaluation Comparing Intensity of Lymphodepletion Before Adoptive Transfer of Tumor-Infiltrating Lymphocytes for Patients With Metastatic Melanoma," Journal of Clinical Oncology, Jul. 10, 2016, 34(20): 2389-2397.
Rosenberg et al., "Adoptive cell transfer as personalized immunotherapy for human cancer," Science—Special Section—Cancer Immunology and Immunotherapy, Apr. 3, 2015, 348(6230): 62-68.

(Continued)

*Primary Examiner* — Yan Xiao
(74) *Attorney, Agent, or Firm* — Morgan, Lewis & Bockius LLP

(57) ABSTRACT

Methods of treating melanomas refractory to other therapies using tumor infiltrating lymphocytes are disclosed.

15 Claims, 43 Drawing Sheets

Specification includes a Sequence Listing.

(56) References Cited

U.S. PATENT DOCUMENTS

| | | | |
|---|---|---|---|
| 9,028,824 B2 | 5/2015 | Min et al. | |
| 9,074,185 B2 | 7/2015 | Dudley et al. | |
| 9,163,085 B2 | 10/2015 | Liu et al. | |
| 9,340,599 B2 | 5/2016 | Hill et al. | |
| 9,359,420 B2 | 6/2016 | Hill et al. | |
| 9,468,678 B2 | 10/2016 | Ahrens et al. | |
| 9,844,569 B2 | 12/2017 | Gros et al. | |
| 9,914,783 B1 | 3/2018 | Afar et al. | |
| 11,433,097 B2* | 9/2022 | Fardis | C12N 5/0634 |
| 2005/0095244 A1 | 5/2005 | Jure-Kunkel et al. | |
| 2005/0106717 A1 | 5/2005 | Wilson et al. | |
| 2005/0191293 A1 | 9/2005 | Desphande et al. | |
| 2010/0136030 A1 | 6/2010 | Salah-Eddine et al. | |
| 2011/0027218 A1 | 2/2011 | Hill et al. | |
| 2011/0052530 A1 | 3/2011 | Dudley et al. | |
| 2011/0111494 A1 | 5/2011 | Hill et al. | |
| 2011/0136228 A1 | 6/2011 | Vera et al. | |
| 2012/0244133 A1 | 9/2012 | Rosenberg et al. | |
| 2013/0102075 A1 | 4/2013 | Vera et al. | |
| 2013/0115617 A1 | 5/2013 | Wilson | |
| 2014/0328791 A1 | 11/2014 | Bossard et al. | |
| 2014/0377284 A1 | 12/2014 | Simons et al. | |
| 2014/0377739 A1 | 12/2014 | Welch et al. | |
| 2015/0110734 A1 | 4/2015 | Hill et al. | |
| 2015/0126709 A1 | 5/2015 | Hill et al. | |
| 2015/0126710 A1 | 5/2015 | Hill et al. | |
| 2015/0132288 A1 | 5/2015 | Simons et al. | |
| 2015/0175966 A1 | 6/2015 | Vera et al. | |
| 2015/0190506 A1 | 7/2015 | Cheung et al. | |
| 2016/0010058 A1 | 1/2016 | Gros et al. | |
| 2016/0208216 A1 | 7/2016 | Vera et al. | |
| 2016/0215262 A1 | 7/2016 | Powell | |
| 2017/0044496 A1 | 2/2017 | Sarnaik et al. | |
| 2017/0081635 A1 | 3/2017 | Sarnaik et al. | |
| 2017/0107490 A1 | 4/2017 | Maeurer | |
| 2017/0152478 A1 | 6/2017 | Rosenberg et al. | |
| 2018/0127715 A1 | 5/2018 | Veerapathran et al. | |
| 2018/0187150 A1 | 7/2018 | De Larichaudy | |
| 2018/0207201 A1 | 7/2018 | Wardell et al. | |
| 2018/0228841 A1 | 8/2018 | Frank et al. | |

FOREIGN PATENT DOCUMENTS

| | | |
|---|---|---|
| WO | WO 95/21925 | 8/1995 |
| WO | WO 2004031370 A1 | 4/2004 |
| WO | WO 2006/121810 | 11/2006 |
| WO | WO 2008/025516 A2 | 3/2008 |
| WO | WO 2009/007120 A2 | 1/2009 |
| WO | WO 2009040789 A2 | 4/2009 |
| WO | WO 2010/003766 A2 | 1/2010 |
| WO | WO 2010/010051 A1 | 1/2010 |
| WO | WO 2010/042433 | 4/2010 |
| WO | WO 2010/078966 A1 | 7/2010 |
| WO | WO 2011/072088 A2 | 6/2011 |
| WO | WO 2012/027328 | 3/2012 |
| WO | WO 2012/032433 A1 | 3/2012 |
| WO | WO 2012/065086 A1 | 5/2012 |
| WO | WO 2012/177788 | 6/2012 |
| WO | WO 2012/129201 A1 | 9/2012 |
| WO | WO 2013/028231 | 2/2013 |
| WO | WO 2013/038191 | 3/2013 |
| WO | WO 2013/057500 A1 | 4/2013 |
| WO | WO 2013/088147 A1 | 6/2013 |
| WO | WO 2013/173835 A1 | 11/2013 |
| WO | WO 2013173835 A1 | 11/2013 |
| WO | WO 2013/188427 A1 | 12/2013 |
| WO | WO 2013188427 A1 | 12/2013 |
| WO | WO 2014/148895 | 9/2014 |
| WO | WO 2014/210036 A1 | 12/2014 |
| WO | WO 2015009604 A1 | 1/2015 |
| WO | WO 2015/119923 | 8/2015 |
| WO | WO 2015/157636 A1 | 10/2015 |
| WO | WO 2015/188839 A1 | 12/2015 |
| WO | WO 2015/189356 A1 | 12/2015 |
| WO | WO 2015/189357 A1 | 12/2015 |
| WO | WO 2015189357 A1 | 12/2015 |
| WO | WO 2016/053338 A1 | 4/2016 |
| WO | WO 2016/096903 A1 | 6/2016 |
| WO | WO 2016096903 A1 | 6/2016 |
| WO | WO2018129336 | 1/2018 |
| WO | WO 2018/081473 A1 | 5/2018 |
| WO | WO 2018/094167 A1 | 5/2018 |
| WO | WO 2018081473 A1 | 5/2018 |
| WO | WO2018094167 | 5/2018 |
| WO | WO 2018/129332 A1 | 7/2018 |
| WO | WO 2018/129336 A1 | 7/2018 |
| WO | WO 2018/182817 A1 | 10/2018 |
| WO | WO 2018/209115 A1 | 11/2018 |
| WO | WO 2018209115 A1 | 11/2018 |
| WO | WO 2018/226714 A1 | 12/2018 |
| WO | WO 2018226714 A1 | 12/2018 |

OTHER PUBLICATIONS

International Search Report and Written Opinion for International Patent Application No. PCT/US2018/036088 dated Dec. 13, 2018, 15 pages.

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Meng, Qingda et al. "Expansion of Tumor-reactive T Cells From Patients With Pancreatic Cancer." Journal of immunotherapy (Hagerstown, Md. : 1997) vol. 39,2 (2016): 81-9. doi:10.1097/CJI.0000000000000111.

Peng, Weiyi et al. "PD-1 blockade enhances T-cell migration to tumors by elevating IFN-γ inducible chemokines." Cancer research vol. 72,20 (2012): 5209-18. doi: 10.1158/0008-5472.CAN-12-1187.

Akkök, C. A et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.

Andersen, Rikke et al. "Long-Lasting Complete Responses in Patients with Metastatic Melanoma after Adoptive Cell Therapy with Tumor-Infiltrating Lymphocytes and an Attenuated IL2 Regimen." Clinical cancer research : an official journal of the American Association for Cancer Research vol. 22,15 (2016): 3734-45. doi:10.1158/1078-0432.CCR-15-1879.

Axelsson et al., "Cryopreserved peripheral blood mononuclear cells are suitable for the assessment of immunological markers in type 1 diabetic children", Cryobiology, Aug. 2008, 57, 201-208.

Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.

Chang C.-H. et al., "Metabolic competition in the tumor microenvironment is a driver of cancer progression", Cell., Sep. 10, 2015, vol. 162, No. 6, pp. 1229-1241.

Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.

Garaud, Soizic et al. "A simple and rapid protocol to non-enzymatically dissociate fresh human tissues for the analysis of infiltrating lymphocytes." Journal of visualized experiments : JoVE ,94 52392. Dec. 6, 2014, doi:10.3791/52392.

Gassner, et al., "Fludarabine modulates composition and function of the T Cell pool in patients with chronic lymphocytic leukaemia", Cancer. Immunol. Immunother., 2011, 60, 75-85.

Gattinoni, et al., "Adoptive immunotherapy for cancer: building on success", Nat. Rev. Immunol. May 2006, 6(5), 383-393.

Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.

(56) References Cited

OTHER PUBLICATIONS

Glassman, A B, and C E Bennett. "Cryopreservation of human lymphocytes: a brief review and evaluation of an automated liquid nitrogen freezer." Transfusion vol. 19,2 (1979): 178-81. doi:10.1046/j.1537-2995.1979.19279160289.x.

Goff et al., "Tumor Infiltrating Lymphocyte Therapy for Metastatic Melanoma: Analysis of Tumors Resected for TIL", J. Immunother, Oct. 2010, 33(8), 840-847.

Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.

Iyer, R.K. et al., "Industrializing Autologous Adoptive Immunotherapies: Manufacturing Advances and Challenges", Frontiers in Medicine, vol. 5, May 23, 2018.

Jin et al., "Enhanced clinical-scale manufacturing of TCR transduced T-cells using closed culture system modules", Journal of Transactional Medicine, col. 16. No. 1, Jan. 24, 2018.

Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.

Lee et al., "Tumor-Infiltrating Lymphocytes in Melanoma", Curr Oncol Rep. Aug. 2012, 14, 468-474.

Muranski, et al., "Increased intensity lymphodepletion and adoptive immunotherapy—how far can we go?", Nat. Clin. Pract. Oncol., Dec. 2006, 3, 668-681.

Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.

Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.

Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.

Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.

Tsoukas et al., "Activation of resting T lymphocytes by anti-CD3 (T3) antibodies in the absence of monocytes", J. Immunol. 1985, 135, 1719.

Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi:10.3791/53424.

Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.

Wilson Wolf—Superior Cell Culture Devices, G-Rex, Oct. 31, 2016.

Ye et al., "Engineered Artificial antigen presenting cells facilitate direct and efficient expansion of tumor infiltrating lymphocytes", J. Translat. Med. 2011, 9(131), 13 pages.

Alva et al., Contemporary experience with high-dose interleukin-2 therapy and impact on survival in patients with metastatic melanoma and metastatic renal cell carcinoma., Cancer Immunol. Immunother. 2016, 65, 1533-1544.

Larkin et al., Combined Nivolumab and Ipilimumab or Monotherapy in Untreated Melanoma., N. Engl. J. Med. 2015, 373, 23-34.

Robert et al., Pembrolizumab versus Ipilimumab in Advanced Melanoma., N. Engl. J. Med. 2015, 372, 2521-32.

Hofmann et al., Cutaneous, gastrointestinal, hepatic, endocrine, and renal side-effects of anti-PD-1 therapy., Eur. J. Cancer 2016, 60, 190-209.

Johnson, et al., Fulminant Myocarditis with Combination Immune Checkpoint Blockade., N. Engl. J. Med. 2016, 375, 1749-1755.

Guy, et al., Vital Signs: Melanoma Incidence and Mortality Trends and Projections United States, 1982-2030., Morbidity Mortality Weekly Rep. 2015, 64, 591-596.

Nelson, IL-2, Regulatory T Cells, and Tolerance., J. Immunol. 2004, 172, 3983-88.

Malek, The Biology of Interleukin-2., Annu. Rev. Immunol. 2008, 26, 453-79.

Fehniger and Caligiuri, Interleukin 15: biology and relevance to human disease., Blood 2001, 97, 14-32.

Spolski and Leonard, Interleukin-21: a double-edged sword with therapeutic potential., Nat. Rev. Drug. Disc. 2014, 13, 379-95.

Swartz et al., Tumor Microenvironment Complexity: Emerging Roles in Cancer Therapy., Cancer Res., 2012, 72, 2473.

Zaretsky, et al., Mutations associated with acquired resistance to PD-1 blockade in melanoma, N. Engl. J. Med. 2016, 375, 819-29.

Gassner Fludarabine modulates composition and function of the T cell pool in patients with chronic lymphocytic leukaemia., et al., Cancer Immunol. Immunother. 2011, 60, 75-85.

Lee, et al., 4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells., PLOS One 2013, 8, e69677.

Gieffers, et al., APG350 Induces Superior Clustering of TRAIL Receptors and Shows Therapeutic Antitumor Efficacy Independent of Cross-Linking via Fog Receptors., Mol. Cancer Therapeutics 2013, 12, 2735-47.

Fisher, et al., Targeting of 4-1BB by monoclonal antibody PF-05082566 enhances T-cell function and promotes anti-tumor activity., Cancer Immunolog. & Immunother. 2012, 61, 1721-33.

Segal, et al., Results from an Integrated Safety Analysis of Urelumab, an Agonist Anti-CD137 Monoclonal Antibody., Clin. Cancer Res. 2016, available at http:/dx.doi.org/ 10.1158/1078-0432.CCR-16-1272.

De Marco, Biotechnological applications of recombinant single-domain antibody fragments., Microbial Cell Factories, 2011, 10, 44.

Ahmad, et al., scFv Antibody: Principles and Clinical Application., Clin. & Dev. Immunol. 2012, 980250.

Monnier, et al., In Vivo Applications of Single Chain Fv (Variable Domain) (scFv) Fragments., Antibodies, 2013, 2, 193-208.

Sadun, et al., Fc-mOX40L Fusion Protein Produces Complete Remission and Enhanced Survival in 2 Murine Tumor Models., J Immunother vol. 31, No. 3, Apr. 2008.

Curti, et al., OX40 Is a Potent Immune-Stimulating Target in Late-Stage Cancer Patients., Cancer Res. 2013, 73, 7189-98.

Weinberg, et al., Anti-OX40 (CD134) Administration to Nonhuman Primates: Immunostimulatory Effects and Toxicokinetic Study., J. Immunother. 2006, 29, 575-585.

Luster, A. D. et al. γ-Interferon transcriptionally regulates an early-response gene containing homology to platelet proteins. (1985) Nature 315:672-676.

Radvanyi, et al., Specific Lymphocyte Subsets Predict Response to Adoptive Cell Therapy Using Expanded Autologous Tumor-Infiltrating Lymphocytes in Metastatic Melanoma Patients., Clin. Cancer Res. 2012, 18, 6758-70.

Santegoets et al., IL-21 promotes the expansion of CD27+CD28+ tumor infiltrating lymphocytes with high cytotoxic potential and low collateral expansion of regulatory T cells., S. J., J Transl Med., 203, 11:37 (https://www.ncbi.nlm.nih.gov/pmc/articles/PMC3626797/).

Sarnaik et al. Efficacy of single administration of tumor-infiltrating lymphocytes (TIL) in heavily pretreated patients with metastatic melanoma following checkpoint therapy. J Clin Oncol. 2017; 35 [suppl; abstr 3045].

International Search Report and Written Opinion for International Patent Application No. PCT/US2018/012633 dated May 25, 2018, 14 pages.

Jia He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Rosenberg, "IL-2: The First Effective Immunotherapy for Human Cancer," The Journal of Immunology, col. 192, No. 12, Jun. 6, 2014.

(56) References Cited

OTHER PUBLICATIONS

Dudley et al., "Generation of Tumor-Infiltrating Lymphocyte Cultures for Use in Adoptive Transfer Therapy for Melanoma Patients," J Immunother., 2003: 26(4): 332-342.

International Search Report and Written Opinion for International Patent Application No. PCT/US2017/058610 dated Mar. 8, 2018, 13 pages.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Chang et al., "Emerging concepts in immunotherapt T-cell metabolism as a therapeutic target", Nat. Immunol., Apr. 2016, 17(4), 364-368.

Donia M, et al.. Simplified protocol for clinical-grade tumor-infiltrating lymphocyte manufacturing with use of the Wave bioreactor. Cytotherapy. Aug. 2014;16(8):1117-20. doi: 10.1016/j.jcyt.2014. 02.004; PubMed PMID: 24831841.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley, et al.,"Cancer Regression and Autoimmunity in Patients After Clonal Repopulation with Antitumor Lymphocytes", Science, Oct. 2002, 298, 850-54.

Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley, et al., "Adoptive Cell Therapy for Patients with Metastatic Melanoma: Evaluation of Intensive Myeloablative Chemoradiation Preparative Regimens" , J. Clin. Oncol., Nov. 2008, 26(32), 5233-39.

Dudley et al., "CD8+ Enriched "Young" Tumor Infiltrating Lymphocytes Can Mediate Regression of Metastatic Melanoma" Clin Cancer Res, 16:6122-6131 (2010).

Goff et al., "Randomized, Prospective Evaluation Comparing Intensity of Lymphodepletion Before Adoptive Transfer of Tumor-Infiltrating Lymphocytes for Patients with Metastatic Melanoma," Journal of Clinical Oncology, vol. 34, No. 20, Jul. 10, 2016, pp. 2389-2397.

Henning AL,et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.

Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.

Huang et al., "Survival, Persistence, and Progressive Differentiation of Adoptively Transferred Tumor-Reactive T Cells Associated with Tumor Regression"; J. Immunother, 28(3), 258-267 (2005).

Jin et al., "Simplified method of the growth of human tumor infiltrating lymphocytes in gas-permiable flasks to numbers needed for patient treatment", J. Immunotherapy, 2012, 35:283-292.

Riddell, et al., "Restoration of Viral Immunity in Immunodeficient Humans by the Adoptive Transfer of T Cell Clones", Science, Jul. 1992, 257, 238-41.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. Adoptive cell therapy for the treatment of patients with metastatic melanoma. Curr Opin Immunol. Apr. 2009;21(2):233-40.

Rufer N, et al.. Telomere length dynamics in human lymphocyte subpopulations measured by flow cytometry. Nat Biotechnol. Aug. 1998;16(8):743-7. PubMed PMID: 9702772.

Sadeghi, et al., "Rapid expansion of T cells: Effects of culture and cryopreservation and improtance of short-term cell recovery", Acta Oncologica 2013, 52, 978-986.

Shen X,et al.. Persistence of tumor infiltrating lymphocytes in adoptive immunotherapy correlates with telomere length. J Immunother. Jan. 2007;30(1):123-9. PubMed PMID:17198091; PubMed Central PMCID: PMC2151201.

Somerville RP, et al.. Clinical scale rapid expansion of lymphocytes for adoptive cell transfer therapy in the WAVE® bioreactor. J Transl Med. Apr. 4, 2012;10:69.

Tran et al., "Minimally Cultured tumor-infiltrating lymphocytes display optimal characteristics for adoptive cell therapy", 2008, J. Immunother., Oct. 2008 31(8), 742-751.

Zhou J, et al., Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.

Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.

Merhavi-Shoham et al, "Adoptive Cell Therapy for Metastatic Melanoma," Cancer Journal, vol. 23, No. 1, Jan. 1, 2017, pp. 48-53.

International Search Report and Written Opinion for International Patent Application No. PCT/US2018/040474 dated Nov. 14, 2018, 17 pages.

Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.

Bajgain, P. et al., "Optimizing the production of suspension cells using the G-Rex "M" series", Molecular Therapy—Methods and Clinical Development, vol. 1, Jan. 1, 2014.

Klapper, J.A. et al., "Single-pass, closed-system rapid expansion of lymphocyte cultures for adoptive cell therapy", Journal of Immunological Methods, vol. 345, No. 1-2, Jun. 30, 2009.

Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.

Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS ONE, vol. 8, No. 4, Apr. 1, 2013, 25 pages.

Forget et al., "Activation and propagation of tumor infiltrating lymphocytes on clinical-grade designer artificial antigen presenting cells for adoptive immunotherapy of melanoma", Journal of Immunotherapy, vol. 37 No.9, Nov. 1, 2014, pp. 448-460.

Hall et al., "Expansion of tumor-infiltrating lymphocytes (TIL) from human pancreatic tumors", Journal for ImmunoTherapy of Cancer, vol. 4, No. 1, pp. 1-12.

Hernandez-Chacon et al., "Costimulation through the CD137/4-1BB Pathway Protects Human Melanoma Tumor-infiltrating Lymphocytes from Activation-induced Cell Death and Enhances Antitumor Effector Function", Journal of ImmunoTherapy, col. 34, No. 3, Apr. 1, 2011, pp. 236-250.

Rosenberg et al, "Durable Complete Responses in Heavily Pretreated Patients with Metastatic Melanoma Using T-Cell Transfer Immunotherapy," Clinical Cancer Research, Vo. 17, No. 13, Jul. 1, 2011, pp. 4550-4557.

Mullinax et al, "Combination of Ipilimumab and Adoptive Cell Therapy with Tumor-Infiltrating Lymphocytes for Patients with Metastatic Melanoma," Frontiers in Oncology, vol. 8, Article 44, Mar. 2, 2018, pp. 1-9.

(56) References Cited

OTHER PUBLICATIONS

Rohaan et al, "Adoptive transfer of tumor-infiltrating lymphocytes in melanoma: a viable treatment option," Journal for ImmunoTherapy of Cancer, vol. 6, No. 1, Oct. 3, 2018 pp. 1-16.

Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.

Wang & Riviere, "Manufacture of tumor- and virus-specific T lymphocytes for adoptive cell therapies", Cancer Gene Therapy, 2015, 22: 85-94.

Frank et al., "Remarkably Stable Tumor-Infiltrating Lymphocytes (TIL) for Infusion Phenotype Following Cryopreservation", Nov. 6, 2016, Retrieved from the Internet: http://www.lovance.com/wp-content/uploads/2017/05/LION16701_Frank_POSTERS_final-0005.

Baruch et al, "Adoptive T Cell Therapy: An Overview of Obstacles and Opportunities: ACT Obstacles and Opportunities," Cancer, vol. 123, No. S11. May 19, 2017, pp. 2154-2162.

International Search Report and Written Opinion dated Jul. 17, 2019 for International Patent Application No. PCT/US2018/064135.

International Search Report and Written Opinion dated Sep. 6, 2018 for International Patent Application No. PCT/US2018/036088.

\* cited by examiner

| CHARACTERISTIC | N=16, % |
|---|---|
| Gender, n (%) | |
| Male | 7 (43.8) |
| Female | 9 (56.3) |
| Age, n (%) | |
| Mean (SD) | 54.8 (8.44) |
| Median | 54.5 |
| Min, Max | 41, 72 |
| Prior therapies, n (%) | |
| IL-2 | 2 (12.5) |
| anti-CTLA-4 | 14 (87.5) |
| anti-PD-1 | 16 (100.0) |

Figure 8

| CHARACTERISTIC | N=16, % |
|---|---|
| Baseline ECOG score, n (%) | |
| 0 | 9 (56.3) |
| 1 | 7 (43.8) |
| BRAF Status, n (%) | |
| Mutated | 9 (56.3) |
| Wild Type | 7 (43.8) |
| Baseline LDH (U/L) | N (%) |
| 1-2 times ULN | 7 (43.8%) |
| > 2 times ULN | 1 (6.25%) |
| Number of Metastatic Sites at enrollment | |
| Median (range) | 4 (2-11) |
| > 3 | 64.3% |

Figure 9

|  | 144-01 (N=16) | | |
| --- | --- | --- | --- |
| PREFERRED TERM | ANY GRADE n (%) | GRADE ≥3 n (%) | GRADE 5 n (%) |
| Number of subjects reporting at least one Treatment-Emergent SAE | 9 (56.3) | 9 (56.3) | 1 (6.3) |
| Febrile neutropenia | 4 (25.0) | 4 (25.0) | 0 (0.0) |
| Pyrexia | 1 (6.3) | 1 (6.3) | 0 (0.0) |
| Systemic inflammatory response syndrome | 1 (6.3) | 1 (6.3) | 0 (0.0) |
| Parvovirus B19 infection* | 1 (6.3) | 1 (6.3) | 1 (6.3) |
| Viral infection | 1 (6.3) | 1 (6.3) | 0 (0.0) |
| Neutrophil count decreased | 3 (18.8) | 3 (18.8) | 0 (0.0) |
| Platelet count decreased | 3 (18.8) | 2 (12.5) | 0 (0.0) |
| Blood bilirubin increased | 1 (6.3) | 1 (6.3) | 0 (0.0) |
| White blood cell count decreased | 1 (6.3) | 1 (6.3) | 0 (0.0) |
| Dehydration | 1 (6.3) | 1 (6.3) | 0 (0.0) |
| Myelodysplastic syndrome | 1 (6.3) | 1 (6.3) | 0 (0.0) |
| Confusional state | 1 (6.3) | 1 (6.3) | 0 (0.0) |
| Hypoxia | 1 (6.3) | 1 (6.3) | 0 (0.0) |
| Hypotension | 1 (6.3) | 1 (6.3) | 0 (0.0) |

Figure 10

| RESPONSE | PATIENTS N=14 n (%) |
|---|---|
| Objective Response Rate | 4 (29%) |
| Disease Control Rate | 9 (64%) |
| Complete Response | 1 (7%) |
| Partial Response | 3 (21%) |
| Stable Disease | 5 (36%) |
| Progressive Disease | 4 (29%) |
| Non-Evaluable* | 1 (7%) |

| TIL # | Number of TIL infused (x10⁹) | Progression on anti-PD-1 before TIL therapy (Yes/No) | Progression on Ipi before TIL therapy (Yes/No) | Ipi Before TIL Harvest (Yes/No) | Progression on DH IL-2 Before TIL | Progression on BRAF inhibitor before TIL (does not include sorafenib) | Progression on Biochemo before TIL (does not include chemo alone) | Brain met at time of treatment | Pre-Radiation treatment of Brain met (Yes/No) |
|---|---|---|---|---|---|---|---|---|---|
| 2543 | 66.60 | Yes | Yes | No | Yes | No | No | Yes | Yes |
| 2594 | 33.00 | Yes | Yes | Yes | No | No | No | No | |
| 2596 | 40.50 | Yes | Yes | Yes | Yes | No | No | Yes | No |
| 2735 | 99.00 | Yes | Yes | Yes | Yes | Yes | No | No | |
| 2751 | 131.00 | Yes | Yes | Yes | No | Yes | No | Yes | Yes |
| 2780 | 41.00 | Yes | Yes | Yes | Yes | No | Yes | Yes | Yes |
| 2692 | 33.00 | Yes | Yes | Yes | Yes | No | Yes | No | |
| 2646 | 24.10 | Yes | Yes | Yes | Yes | No | No | No | |
| 2884 | 17.00 | Yes | Yes | Yes | No | Yes | No | Yes | Yes |

| TIL # | Staging | ECOG | Melanoma type | Age | BRAF mutation | NRASD mutation | Kit mutation | Vital Status | Progressed 1=Yes 0=No |
|---|---|---|---|---|---|---|---|---|---|
| 2543 | IV; M1c | 0 | Cutaneous | 42 | V600E | NT | NT | Alive | 1 |
| 2594 | IV; M1c | 0 | Cutaneous | 53 | WT | WT | WT | Deceased | 1 |
| 2596 | IV; M1c | 0 | Cutaneous | 41 | WT | Q61R | WT | Deceased | 1 |
| 2735 | IV; M1c | 1 | Cutaneous | 35 | V600E | WT | WT | Deceased | 1 |
| 2751 | IV; M1c | 1 | Cutaneous | 56 | V600E | WT | WT | Deceased | 1 |
| 2780 | IV; M1c | 0 | Undetermined | 55 | G466E | WT | WT | Alive | 1 |
| 2692 | IV; M1c | 0 | Cutaneous | 54 | WT | WT | WT | Deceased | 1 |
| 2646 | IV; M1c | 1 | Undetermined | 47 | WT | Q61R | WT | Deceased | 1 |
| 2884 | IV; M1c | 0 | Undetermined | 55 | V600E | WT | WT | Deceased | |

| # of systemic therapies before TIL | LDH at time of TIL HARVEST (elevated/ no elevated) | LDH at time of TIL INFUSION (elevated/ no elevated) | LDH value at time of TIL INFUSION (normal range is 313-618) | Site for TIL resection | Gender | Best irRC |
|---|---|---|---|---|---|---|
| 4 | non elevated | Not Elevated | 380 | small bowel | Male | PR |
| 2 | elevated | Not Elevated | 387 | cut/sub-cut | Male | SD |
| 4 | non elevated | Not Elevated | 389 | cut/sub-cut | Female | SD |
| 10 | non elevated | Not Elevated | 390 | Liver | Male | PR |
| 7 | elevated | Not Elevated | 596 | cut/sub-cut and other | Male | PD |
| 8 | elevated | Not Elevated | 598 | cut/sub-cut | Male | PR |
| 5 | non elevated | Elevated | 872 | Liver | Female | SD |
| 11 | elevated | Elevated | 1478 | cut/sub-cut and other | Male | SD |
| 6 | elevated | Elevated | 3073 | other | Female | PD |

| Number of Months from TIL Infusion to Progression (+/- 1 month) | Number of Months between TIL treatment and date of death or between TIL treatment and last contact date if patient still alive | # Months between TIL treatment and date of death | Site of TIL Harvest | Time from metastatic disease DX to RX (months) | # of IL-2 doses (1st course) | # of IL-2 doses (2nd course) |
|---|---|---|---|---|---|---|
| 7 | 50 |  | 4 | 21 | 7 | 8 |
| 11 | 17 | 17 | 1 | 26 | 6 | 0 |
| 4 | 11 | 11 | 1 | 21 | 7 | 14 |
| 2 | 3 | 3 | 4 | 78 | 4 | 6 |
|  | 4 | 4 | 4 | 23 | 1 | 0 |
| 5 | 17 |  | 1 | 21 | 1 | 0 |
| 2 | 9 | 9 | 4 | 40 | 3 | 6 |
| 1 | 3 | 3 | 1,2 | 16 | 3 | 0 |
|  | 3 | 3 | 4 | 14 | 3 | 0 |

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

Figure 22

| Process 1C: 43-55 Days for Steps A - E | Process 2A: about 22 days from Steps A - E |
|---|---|
| 1. STEP A<br>Obtain Patient Tumor Sample | 1. STEP A<br>Obtain Patient Tumor Sample |
| 2. STEP B<br>Fragmentation and First Expansion<br>11 days to 21 days | 2. STEP B<br>Fragmentation and First Expansion<br>3 days to 14 days |
| 3. STEP C<br>First Expansion to Second Expansion Transition<br>Optional Storage until Selection | 3. STEP C<br>First Expansion to Second Expansion Transition<br>No Storage and Closed System |
| 4. STEP D<br>Second Expansion<br>IL-2, OKT-3, antigen-presenting feeder cells<br>Optionally repeat one or more times | 4. STEP D<br>Second Expansion<br>IL-2, OKT-3, and antigen-presenting feeder cells<br>Closed System |
| 5. STEP E<br>Harvest TILS from Step D | 5. STEP E<br>Harvest TILS from Step D<br>Closed System |
| 6. STEP F<br>Final Formulation and/or Transfer to Infusion Bag | 6. STEP F<br>Final Formulation and/or Transfer to Infusion Bag<br>(optionally cryopreserve) |

Figure 23

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40×10$^6$ TIL | • Pre-REP TIL directly move to REP on day 11<br>• REP requires 25-200×10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5×10$^6$ TIL and 5×10$^8$ PBMC feeders per flask on REP day 0<br>• Split to 18-36 flasks on REP day 7<br>• 14 day duration | • 1 GREX-500M flask on day 11<br>• 25-200×10$^6$ TIL and 5×10$^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system' | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in LN$_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

Ongoing: Melanoma Phase 2 Study, Cohort 1 (Cont.)

| Pt No | Infusion | # Cells Infused | Response Day 42 | Response Day 84 | Response 6 Months | Response 9 Months | BOR |
|---|---|---|---|---|---|---|---|
| 007-001 | 5-Jan-17 | $3.0 \times 10^{10}$ | SD | PD | - | - | SD |
| 004-005 | 25-Jan-17 | $3.3 \times 10^{9}$ | PD | - | - | - | PD |
| 007-002 | 28-Feb-17 | $8.0 \times 10^{10}$ | SD | PD | - | - | SD |
| 003-010 | 5-Apr-17 | $3.0 \times 10^{10}$ | SD | SD | - | - | SD |
| 003-012 | 15-Mar-17 | $5.2 \times 10^{10}$ | PD | PD | - | - | PD |
| 007-005 | 16-May-17 | $6.4 \times 10^{10}$ | PR | - | - | - | SD |
| 008-001 | 16-Jun-17 | $4.53 \times 10^{10}$ | SD | PD | - | - | SD |
| 003-014 | 11-May-17 | $3.16 \times 10^{10}$ | PD | - | PD | - | PD |
| 007-007 | 25-Jul-17 | $1.1 \times 10^{11}$ | PR | PR | PR | Patient left study prior to Month 9 - physician discretion | PR |
| 004-007 | 9-Aug-17 | $7.3 \times 10^{9}$ | PD | - | - | - | PD |

*Figure 24A*

Ongoing: Melanoma Phase 2 Study, Cohort 1 (Cont.)

| Pt No | Infusion | # Cells Infused | Response Day 42 | Response Day 84 | Response 6 Months | Response 9 Months | BOR |
|---|---|---|---|---|---|---|---|
| 003-020 | 20-Sep-2017 | 8.0 x 10 | PD | Discontinued from the study due to PD | - | - | PD |
| 006-003 | 17-Oct-2017 | 8.3 x 10 | SD | - | - | - | SD |

*Figure 24B*

| CHARACTERISTIC | Historical Cohort 1* N = 16, (%) | Cohort 2 N = 13, (%) |
|---|---|---|
| Gender, n (%) | | |
|   Male | 7 (44) | 5 (39) |
|   Female | 9 (56) | 8 (62) |
| Age | | |
|   Median | 55 | 54 |
|   Min, Max | 41, 72 | 35, 66 |
| Prior therapies, n (%) | | |
|   Mean # prior systemic therapies | 3 | 4 |
|   Anti-CTLA-4 | 14 (88) | 13 (100) |
|   Anti-PD-1 | 21 (100) | 13 (100) |
| Target Lesion Sum of Diameter (mm) | | |
|   Mean (SD) | 104 (68) | 141 (102) |
|   Min, Max | 15, 225 | 38, 342 |

| CHARACTERISTIC | Historical Cohort 1* N = 16, (%) | Cohort 2 N = 13, (%) |
|---|---|---|
| Baseline ECOG score, n (%) | | |
|   0 | 9 (56) | 8 (62) |
|   1 | 7 (44) | 5 (39) |
| BRAF Status, n (%) | | |
|   Mutated | 9 (56) | 6 (46) |
|   Wild Type | 7 (44) | 7 (54) |
| Baseline LDH (U/L [SD]) | | |
|   1-2 times ULN | 7 (44) | 7 (54) |
|   Min, Max | 1 (6) | 2 (15) |
| Number of Target & Non-Target Lesions (at Base Line) | | |
|   >3 | 12 (75) | 10 (77) |
|   Mean | 5.6 | 5.5 |

*Figure 27*

| PREFERRED TERM | Historical Cohort 1 (N = 16) | | | Cohort 2 (N = 13) | | |
| --- | --- | --- | --- | --- | --- | --- |
| | Any Grade n (%) | Grade 3/4 n (%) | Grade 5 n (%) | Any Grade n (%) | Grade 3/4 n (%) | Grade 5 n (%) |
| Number of patients reporting at least one Treatment-Emergent AE | 14 (87.5) | 14 (87.5) | 0 | 12 (85.7) | 11 (78.6) | 0 |
| Nausea | 14 (87.5) | 0 | 0 | 7 (53.8) | 0 | 0 |
| Platelet count decreased | 12 (75.0) | 12 (75.0) | 0 | 7 (53.8) | 6 (46.2) | 0 |
| Anaemia | 11 (68.8) | 8 (50.0) | 0 | 8 (61.5) | 7 (53.8) | 0 |
| Neutrophil count decreased | 11 (68.8) | 11 (68.8) | 0 | 6 (46.2) | 6 (46.2) | 0 |
| Febril neutropenia | 10 (62.5) | 10 (62.5) | 0 | 7 (53.8) | 6 (46.2) | 0 |
| White blood count decreased | 10 (62.5) | 10 (62.5) | 0 | 6 (46.2) | 6 (46.2) | 0 |
| Chills | 9 (56.3) | 0 | 0 | 6 (46.2) | 1 (7.7) | 0 |
| Diarrhoea | 8 (50.0) | 1 (6.3) | 0 | 4 (30.8) | 0 | 0 |
| Fatigue | 7 (43.8) | 0 | 0 | 7 (53.8) | 0 | 0 |
| Vomiting | 7 (43.8) | 0 | 0 | 2 (15.4) | 0 | 0 |
| Constipation | 6 (37.5) | 0 | 0 | 3 (23.1) | 0 | 0 |
| Decreased appetite | 5 (31.3) | 0 | 0 | 4 (30.8) | 0 | 0 |
| Headache | 5 (31.3) | 0 | 0 | 3 (23.1) | 0 | 0 |
| Hypocalcaemia | 5 (31.3) | 0 | 0 | 1 (7.7) | 0 | 0 |
| Hypokalaemia | 5 (31.3) | 0 | 0 | 3 (23.1) | 0 | 0 |
| Hypophosphataemia | 5 (31.3) | 5 (31.3) | 0 | 4 (23.1) | 1 (7.7) | 0 |
| Hypotension | 5 (31.3) | 2 (12.5) | 0 | 3 (23.1) | 3 (7.7) | 0 |
| Lymphocyte count decreased | 5 (31.3) | 5 (31.3) | 0 | 3 (23.1) | 3 (23.1) | 0 |
| Nasal Congestion | 5 (31.3) | 0 | 0 | 0 | 0 | 0 |
| Pyrexia | 5 (31.3) | 0 | 0 | 9 (69.2) | 1 (7.7) | 0 |
| Cough | 4 (25.0) | 0 | 0 | 4 (30.8) | 0 | 0 |
| Oedema peripheral | 4 (25.0) | 0 | 0 | 4 (30.8) | 0 | 0 |
| Pruritus | 4 (25.0) | 0 | 0 | 4 (30.8) | 0 | 0 |

Notes: Adverse events are coded by MedDRA version 18.1.

Patients with multiple events for a given preferred term are counted only once using the maximum grade under each preferred term.

Events are sorted by decreasing frequency of preferred term under SOC per any grade.

Treatment-Emergent Adverse Events refer to all AEs starting on or after the first dose date of pre-treatment chemotherapy (Fludarabine and Cyclophosphamide) up to the last dose of IL2 + 30 days.

Figure 28

| CHARACTERISTIC | Cohort 2<br>N = 17, (%) |
|---|---|
| Gender, n (%) | |
|   Male | 8 (47) |
|   Female | 9 (53) |
| Age | |
|   Median | 54 |
|   Min, Max | 35, 66 |
| Prior therapies, n (%) | |
|   Mean # prior systemic therapies | 3.6 |
|   Anti-CTLA-4 | 15 (88) |
|   Anti-PD-1 | 16 (94) |
| Target Lesion Sum of Diameter (mm) | |
|   Mean (SD) | 140 (93) |
|   Min, Max | 38, 342 |

| CHARACTERISTIC | Cohort 2<br>N = 17, (%) |
|---|---|
| Baseline ECOG, n (%) | |
|   0 | 11 (65) |
|   1 | 6 (35) |
| BRAF Status, n (%) | |
|   Mutated | 5 (29) |
|   Wild Type | 9 (53) |
|   Unknown | 3 (18) |
| Baseline LDH (U/L [SD]) | |
|   1-2 times ULN | 8 (47) |
|   > 2 times ULN | 2 (12) |
| Number of Target & Non-Target Lesions (at Base Line) | |
|   > 3 | 12 (71) |
|   Mean | 5.9 |

Cohort 2 has:

3.6 median prior therapies

High tumor burden at baseline as reflected by 140 mm sum of diameters for target lesions

*Figure 34*

|  | Cohort 2 (N = 17) | | |
| --- | --- | --- | --- |
| PREFERRED TERM | Any Grade n (%) | Grade 3/4 n (%) | Grade 5 n (%) |
| Number of patients reporting at least one Treatment-Emergent AE | 16 (94.1) | 16 (94.1) | 0 |
| Pyrexia | 13 (76.5) | 1 (5.9) | 0 |
| Anaemia | 11 (64.7) | 10 (58.8) | 0 |
| Neutrophil count decreased | 10 (58.8) | 10 (58.8) | 0 |
| Platelet count decreased | 10 (58.8) | 8 (47.1) | 0 |
| Februle neutropenia | 10 (58.8) | 8 (47.1) | 0 |
| Fatigue | 10 (58.8) | 0 | 0 |
| Chills | 9 (52.9) | 1 (5.9) | 0 |
| Nausea | 9 (52.9) | 0 | 0 |
| White blood cell count decreased | 8 (47.1) | 8 (47.1) | 0 |
| Lymphocyte count decreased | 6 (35.3) | 6 (35.3) | 0 |
| Diarroea | 6 (35.3) | 0 | 0 |
| Decreased appetite | 6 (35.3) | 0 | 0 |

Notes: Patients with multiple events for a given preferred term are counted only once using the maximum grade under each preferred term. Treatment-Emergent Adverse Events refer to all AEs starting on or after the first dose date of pre-treatment chemotherapy (Fludarabine and Cyclophosphamide) up to the last dose of IL-2 + 30 days.

*Figure 35*

| RESPONSE | PATIENTS, N=10 n (%) |
|---|---|
| Objective Response Rate | 4 (40%) |
| Disease Control Rate | 8 (80%) |
| Partial Response | 4 (40%) |
| Stable Disease | 4 (40%) |
| Progressive Disease | 1 (10%) |
| Non-Evaluable* | 1 (10%) |

*Figure 38*

METHODS OF USING TUMOR INFILTRATING LYMPHOCYTES IN DOUBLE-REFRACTORY MELANOMA

CROSS-REFERENCE TO RELATED APPLICATION

This application is a U.S. National Phase entry of International Patent Application No. PCT/US2018/036088, filed Jun. 5, 2018, which claims the benefit of U.S. Provisional Patent Application No. 62/515,257, filed Jun. 5, 2017, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Mar. 25, 2020, is named 116983-5031-US_ST25.txt and is 122 kilobytes in size.

FIELD OF THE INVENTION

Methods of using tumor infiltrating lymphocytes (TILS) in the treatment of double-refractory melanoma are disclosed herein.

BACKGROUND OF THE INVENTION

Treatment of melanoma remains challenging, particularly for patients that do not respond to commonly-used initial lines of therapy, including nivolumab monotherapy, pembrolizumab monotherapy, therapy using a combination of nivolumab and ipilimumab, ipilimumab monotherapy, therapy using a combination of dabrafenib and trametinib, vemurafenib monotherapy, and pegylated interferon (preinterferon) alfa-2b. Approved first line treatments for metastatic melanoma include immunotherapeutic strategies blocking PD-1 (pembrolizumab, nivolumab), or combining nivolumab with the anti-CTLA4 blocker ipilimumab, or chemotherapy with agents targeting specific activating mutations in the BRAF pathway (e.g., vemurafenib, dabrafenib, trametinib). Following disease progression, patients can receive additional treatment with anti-PD-1 monotherapy; nivolumab/ipilimumab combination therapy; ipilimumab monotherapy; targeted therapy if BRAF mutant; high-dose aldesleukin (interleukin-2; IL-2); cytotoxic agents (e.g., dacarbazine, temozolomide, paclitaxel, cisplatin, carboplatin, vinblastine); or imatinib for KIT-mutant melanoma. In 2015, talimogene laherparepvec, a live oncolytic virus therapy, was approved for the local treatment of unresectable cutaneous, subcutaneous, and nodal lesions in patients with melanoma recurrent after initial surgical excision. This product has not been shown to improve overall survival or to have an effect on visceral metastases.

Until recently, high-dose aldesleukin was the only FDA-approved systemic therapy for metastatic melanoma capable of inducing durable objective cancer responses, with an overall objective response rate (ORR) of 16% and durable complete tumor regressions (CRs) observed in up to 6% of treated patients (Proleukin® (aldesleukin) Label, FDA, July 2012). Alva, et al. *Cancer Immunol. Immunother.* 2016, 65, 1533-1544. The recently approved PD-1 immune checkpoint inhibitors pembrolizumab and nivolumab approximately double the rate of durable responses in metastatic melanoma relative to aldesleukin treatment. Larkin, et al., *N. Engl. J. Med.* 2015, 373, 23-34; Robert, et al., *N. Engl. J. Med.* 2015, 372, 2521-32. In previously treated patients, the ORR for nivolumab is 32%, with higher and more durable responses correlated with higher levels of PD-1 ligand expression by tumors; and the ORR for pembrolizumab following prior therapy with ipilimumab is 21% (Table 2). In treatment naïve patients, durable objective responses are achieved in 50% of patients when nivolumab and ipilimumab administered in combination, although the CR rate remains low at 8.9% (Opdivo® (nivolumab) Label, FDA, October 2016).

Use of the checkpoint inhibitors is associated with a spectrum of immune-related adverse events, including pneumonitis, colitis, hepatitis, nephritis and renal dysfunction (Opdivo (nivolumab) Label, FDA, October 2016). Hofmann, et al., *Eur. J. Cancer* 2016, 60, 190-209. Increased toxicity is observed in patients treated with nivolumab and ipilimumab combination therapy. Treatment-related adverse events leading to discontinuation of therapy occurred in 36.4%, 7.7% and 14.8% of patients receiving the combination therapy, nivolumab alone or ipilimumab alone, respectively. Larkin, et al., *N. Engl. J. Med.* 2015, 373, 23-34; Johnson, et al., *N. Engl. J Med.* 2016, 375, 1749-1755.

Although the targeted therapies and immune checkpoint inhibitors can achieve dramatic responses in patients with metastatic melanoma, death rates for this cancer are projected to remain stable through 2030. The overall age-adjusted melanoma death rate was 2.7 per 100000 in 2011 and remained at this level in 2015. Guy, et al., *Morbidity Mortality Weekly Rep.* 2015, 64, 591-596.

Treatment of bulky, refractory cancers using adoptive autologous transfer of tumor infiltrating lymphocytes (TILs) represents a powerful approach to therapy for patients with poor prognoses. Gattinoni, et al., *Nat. Rev. Immunol.* 2006, 6, 383-393. TILs are dominated by T cells, and IL-2-based TIL expansion followed by a "rapid expansion process" (REP) has become a preferred method for TIL expansion because of its speed and efficiency. Dudley, et al., Science 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. A number of approaches to improve responses to TIL therapy in melanoma and to expand TIL therapy to other tumor types have been explored with limited success, and the field remains challenging. Goff, et al., *J. Clin. Oncol.* 2016, 34, 2389-97; Dudley, et al., *J. Clin. Oncol.* 2008, 26, 5233-39; Rosenberg, et al., *Clin. Cancer Res.* 2011, 17, 4550-57. There is an unmet need to standardize TIL production as well as identify patient populations and specific types of cancers that are most likely to benefit from TIL therapy.

The present invention provides the surprising finding that TILs may be used in the treatment of a subpopulation of patients suffering from melanoma that is refractory to at least two prior therapies, which may include immune checkpoint inhibitors.

SUMMARY OF THE INVENTION

In an embodiment, the present disclosure provides a method of treating double-refractory metastatic melanoma in a patient in need thereof, the method comprising administering a therapeutically effective population of tumor infiltrating lymphocytes (TILs) to the patient.

In an embodiment and in accordance with the above, wherein the double-refractory metastatic melanoma is a cutaneous double-refractory metastatic melanoma.

In an embodiment and in accordance with any of the above, the double-refractory metastatic melanoma is refractory to at least two prior systemic treatment courses, not including neo-adjuvant or adjuvant therapies.

In an embodiment and in accordance with any of the above, the double-refractory metastatic melanoma is refractory to aldesleukin or a biosimilar thereof.

In an embodiment and in accordance with any of the above, the double-refractory metastatic melanoma is refractory to pembrolizumab or a biosimilar thereof.

In an embodiment and in accordance with any of the above, the double-refractory metastatic melanoma is refractory to nivolumab or a biosimilar thereof.

In an embodiment and in accordance with any of the above, the double-refractory metastatic melanoma is refractory to ipilimumab or a biosimilar thereof.

In an embodiment and in accordance with any of the above, the double-refractory metastatic melanoma is refractory to ipilimumab or a biosimilar thereof and pembrolizumab or a biosimilar thereof.

In an embodiment and in accordance with any of the above, the double-refractory metastatic melanoma is refractory to ipilimumab or a biosimilar thereof and nivolumab or a biosimilar thereof.

In an embodiment and in accordance with any of the above, the double-refractory metastatic melanoma is refractory to a BRAF inhibitor.

In an embodiment and in accordance with any of the above, the double-refractory metastatic melanoma is refractory to a PD-L1 inhibitor.

In an embodiment and in accordance with any of the above, the PD-L1 inhibitor is selected from the group consisting of avelumab, atezolizumab, durvalumab, and biosimilars thereof.

In an embodiment and in accordance with any of the above, the double-refractory metastatic melanoma is refractory to a combination of a PD-1 inhibitor and a CTLA-4 inhibitor.

In an embodiment and in accordance with any of the above, the PD-1 inhibitor is nivolumab or a biosimilar thereof and the CTLA-4 inhibitor is selected from the group consisting of ipilumumab, tremelimumab, and biosimilars thereof.

The In an embodiment and in accordance with any of the above, the double-refractory metastatic melanoma is refractory to a combination of a BRAF inhibitor and a MEK inhibitor.

In an embodiment and in accordance with any of the above, the BRAF inhibitor is dabrafenib or a pharmaceutically-acceptable salt thereof and the MEK inhibitor is trametinib or a pharmaceutically-acceptable salt or solvate thereof.

In an embodiment and in accordance with any of the above, the metastatic melanoma is resistant to a PD-1 inhibitor or PD-L1 inhibitor.

In an embodiment and in accordance with any of the above, the PD-1 or PD-L1 inhibitor is selected from the group consisting of nivolumab, pembrolizumab, avelumab, atezolizumab, durvalumab, and biosimilars thereof.

In an embodiment and in accordance with any of the above, the patient does not possess a BRAF mutation.

In an embodiment and in accordance with any of the above, the patient has received at most 4 doses of nivolumab or a biosimilar thereof prior to receiving the therapeutically effective population of TILs.

In an embodiment and in accordance with any of the above, the patient has progressed or had no response to at least two prior systemic treatment courses.

In an embodiment, the present disclosure provides method of treating double-refractory metastatic melanoma in a patient in need thereof, the method comprising:
(a) obtaining a first population of TILs from a tumor resected from the patient by processing a tumor sample obtained from the patient into multiple tumor fragments;
(b) adding the tumor fragments into a closed system;
(c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d) to provide a harvested TIL population, wherein the transition from step (d) to step (e) occurs without opening the system;
(f) transferring the harvested TIL population from step (e) to an infusion bag, wherein the transfer from step (e) to (f) occurs without opening the system, and optionally cryopreserving the harvested TIL population and
(g) administering a therapeutically effective amount of the harvested TIL population to the patient with double-refractory metastatic melanoma.

In an embodiment and in accordance with the above-described method, wherein the patient has been previously treated with a PD-1 inhibitor or a biosimilar thereof.

In an embodiment and in accordance with any of the above, wherein the PD-1 inhibitor is selected from the group consisting of nivolumab, pembrolizumab, and biosimilars thereof.

In an embodiment and in accordance with any of the above, wherein the patient has been previously treated with a PD-L1 inhibitor or a biosimilar thereof.

In an embodiment and in accordance with any of the above, wherein the PD-L1 inhibitor is selected from the group consisting of avelumab, atezolizumab, durvalumab, and biosimilars thereof.

In an embodiment and in accordance with any of the above, wherein the PD-1 inhibitor or a biosimilar thereof was co-administered with a CTLA-4 inihbitor or biosimilar thereof.

In an embodiment and in accordance with any of the above, wherein the PD-L1 inhibitor or a biosimilar thereof was co-administered with a CTLA-4 inihbitor or biosimilar thereof.

In an embodiment and in accordance with any of the above, wherein the patient has been previously treated with one additional prior line of systemic therapy.

In an embodiment and in accordance with any of the above, wherein the one additional prior line of systemic therapy is a BRAF inhibitor or a pharmaceutically-acceptable salt thereof.

In an embodiment and in accordance with any of the above, wherein the BRAF inhibitor is selected from the group consisting of vemurafenib, dabrafenib, and pharmaceutically-acceptable salts thereof.

In an embodiment and in accordance with any of the above, wherein the one additional prior line of systemic therapy is a MEK inhibitor or a pharmaceutically-acceptable salt or solvate thereof.

In an embodiment and in accordance with any of the above, wherein the MEK inhibitor is selected from the group consisting of trametinib, cobimetinib, and pharmaceutically-acceptable salts or solvates thereof.

In an embodiment and in accordance with any of the above, wherein the one additional prior line of systemic therapy is a combination of a BRAF inhibitor or a pharmaceutically-acceptable salt thereof and a MEK inhibitor or a pharmaceutically-acceptable salt or solvate thereof.

In an embodiment and in accordance with any of the above, wherein the BRAF inhibitor is selected from the group consisting of vemurafenib, dabrafenib, and pharmaceutically-acceptable salts thereof, and the MEK inhibitor is selected from the group consisting of trametinib, cobimetinib, and pharmaceutically-acceptable salts or solvates thereof.

In an embodiment and in accordance with any of the above, wherein the one additional prior line of systemic therapy is a CTLA-4 inhibitor or a biosimilar thereof.

In an embodiment and in accordance with any of the above, wherein the CTLA-4 inhibitor is selected from the group consisting of ipilumumab, tremelimumab, and biosimilars thereof.

In an embodiment and in accordance with any of the above, wherein the one additional prior line of systemic therapy is chemotherapeutic regimen.

In an embodiment and in accordance with any of the above, wherein the chemotherapeutic regimen comprises dacarbazine or temozolimide.

In an embodiment and in accordance with any of the above, wherein the first expansion is performed over a period of about 11 days.

In an embodiment and in accordance with any of the above, wherein the IL-2 is present at an initial concentration of between 1000 IU/mL and 6000 IU/mL in the cell culture medium in the first expansion step (c).

In an embodiment and in accordance with any of the above, wherein in the second expansion step (d), the IL-2 is present at an initial concentration of between 1000 IU/mL and 6000 IU/mL and the OKT-3 antibody is present at an initial concentration of about 30 ng/mL.

In an embodiment and in accordance with any of the above, wherein the first expansion is performed using a gas permeable container.

In an embodiment and in accordance with any of the above, wherein the second expansion is performed using a gas permeable container.

In an embodiment and in accordance with any of the above, wherein the cell culture medium in the first expansion step (c) further comprises a cytokine selected from the group consisting of IL-4, IL-7, IL-15, IL-21, and combinations thereof.

In an embodiment and in accordance with any of the above, wherein the cell culture medium in the second expansion step (d) further comprises a cytokine selected from the group consisting of IL-4, IL-7, IL-15, IL-21, and combinations thereof.

In an embodiment and in accordance with any of the above, further comprising the step of treating the patient with a non-myeloablative lymphodepletion regimen prior to administering the TILs to the patient.

In an embodiment and in accordance with any of the above, wherein the non-myeloablative lymphodepletion regimen comprises the steps of administration of cyclophosphamide at a dose of 60 mg/m2/day for two days followed by administration of fludarabine at a dose of 25 mg/m2/day for five days.

In an embodiment and in accordance with any of the above, further comprising the step of treating the patient with an IL-2 regimen starting on the day after administration of the TILs to the patient.

In an embodiment and in accordance with any of the above, wherein the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In an embodiment and in accordance with any of the above, wherein the therapeutically effective population of TILs comprises from about 2.3×1010 to about 13.7×1010 TILs.

BRIEF DESCRIPTION OF THE DRAWINGS

The foregoing summary, as well as the following detailed description of the invention, will be better understood when read in conjunction with the appended drawings.

FIG. 8 summarizes patient characteristics in the clinical study.

FIG. 9 summarizes patient characteristics in the clinical study.

FIG. 10 summarizes treatment emergent serious adverse events in the clinical study. The "*" indicates a not related to therapy event occurring six months after treatment.

FIG. 11 summarizes efficacy results in the clinical study.

FIG. 17 illustrates the results of a second clinical study performing using a TIL manufacturing process as described in Radvanyi, et al., *Clin. Cancer Res.* 2012, 18, 6758-70. NT refers to not tested, WT refers to wild type, and irRC refers to immune-related response criteria. Site of TIL harvest is specified as follows: 1: skin/SC; 2: lymph nodes; 3: lungs; and 4: gastrointestinal/visceral.

FIG. 18: Exemplary Process 2A chart providing an overview of Steps A through F.

FIG. 22: Comparison table of Steps A through F from exemplary embodiments of process 1C and process 2A.

FIG. 23: Detailed comparison of an embodiment of process 1C and an embodiment of process 2A.

FIG. 24A-24B: Updated efficacy data for Cohort 1 from the final data cut (N=23 patients). Abbreviations: PR, partial response; SD, stable disease; PD, progressive disease.

FIG. 27: Table illustrating the Comparison Patient Characteristics from Cohort 1 (ASCO 2017) vs Cohort 2.

FIG. 28: Table illustrating treatment emergent adverse events (≥30%).

FIG. 34: Updated patient characteristics for Cohort 2 of the phase 2 clinical trial in metastatic melanoma from the second data cut (N=17 patients).

FIG. 35: Treatment emergent adverse events for Cohort 2 (≥30%) from the second data cut (N=17 patients).

FIG. 38: Updated efficacy data for evaluable patients from Cohort 2 from the second data cut (N=17 patients). The * indicates a non-evaluable patient that did not reach the first assessment. All efficacy-evaluable patients had received prior anti-PD-1 and anti-CTLA-4 checkpoint inhibitor therapies.

BRIEF DESCRIPTION OF THE SEQUENCE LISTING

Figure 1:
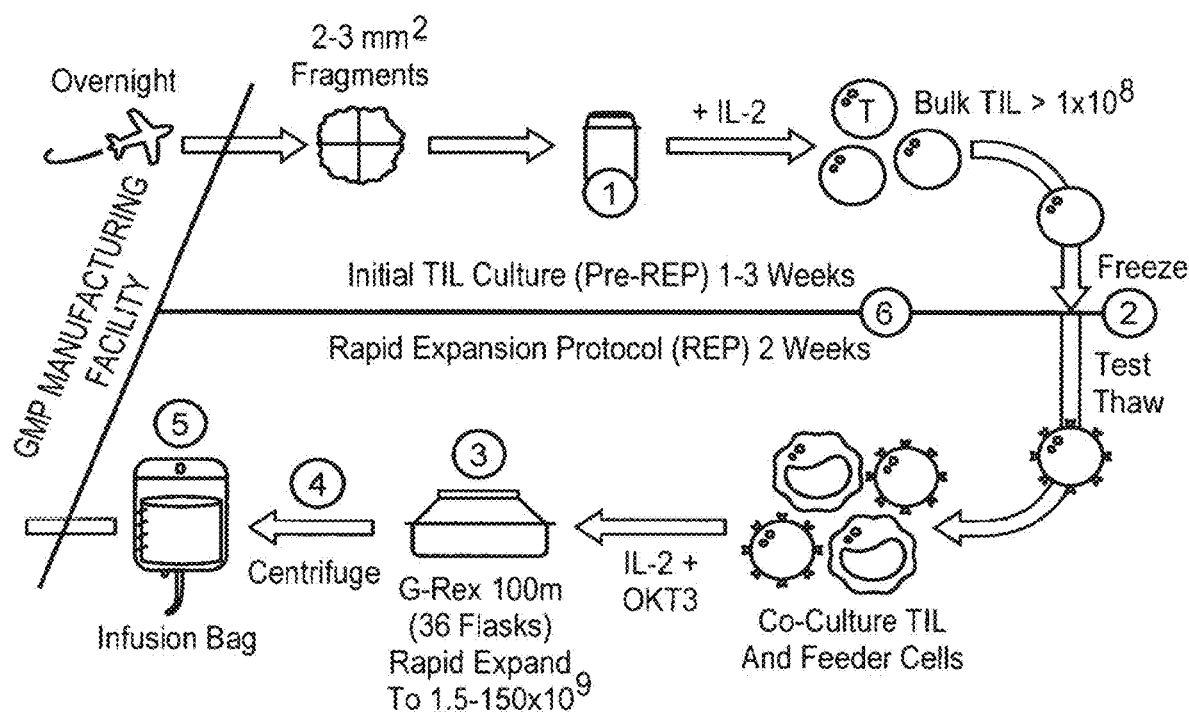
FIG. 1 illustrates a TIL expansion and therapeutic treatment process. Step 1 refers to the addition of 4 tumor fragments into 10 G-Rex 10 flasks. At step 2, approximately $40 \times 10^6$ TILs or greater are obtained. At step 3, a split occurs into 36 G-Rex 100 flasks for REP. TILs are harvested by centrifugation at step 4. Fresh TIL product is obtained at step 5 after a total process time of approximately 43 days, at which point TILs may be infused into a patient.

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO:10 is the amino acid sequence of murine 4-1BB.

SEQ ID NO:11 is the heavy chain for the 4-1BB agonist monoclonal antibody utomilumab (PF-05082566).

SEQ ID NO:12 is the light chain for the 4-1BB agonist monoclonal antibody utomilumab (PF-05082566).

SEQ ID NO:13 is the heavy chain variable region (VH) for the 4-1BB agonist monoclonal antibody utomilumab (PF-05082566).

SEQ ID NO:14 is the light chain variable region (VL) for the 4-1BB agonist monoclonal antibody utomilumab (PF-05082566).

SEQ ID NO:15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO:17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region (VH) for the 4-1BB agonist monoclonal antibody urelumab (BMS-663513).

SEQ ID NO:24 is the light chain variable region (VL) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:31 is an Fc domain for a TNFRSF agonist fusion protein.

SEQ ID NO:32 is a linker for a TNFRSF agonist fusion protein.

SEQ ID NO:33 is a linker for a TNFRSF agonist fusion protein.

SEQ ID NO:34 is a linker for a TNFRSF agonist fusion protein.

SEQ ID NO:35 is a linker for a TNFRSF agonist fusion protein.

SEQ ID NO:36 is a linker for a TNFRSF agonist fusion protein.

SEQ ID NO:37 is a linker for a TNFRSF agonist fusion protein.

SEQ ID NO:38 is a linker for a TNFRSF agonist fusion protein.

SEQ ID NO:39 is a linker for a TNFRSF agonist fusion protein.

SEQ ID NO:40 is a linker for a TNFRSF agonist fusion protein.

SEQ ID NO:41 is a linker for a TNFRSF agonist fusion protein.

SEQ ID NO:42 is an Fc domain for a TNFRSF agonist fusion protein.

SEQ ID NO:43 is a linker for a TNFRSF agonist fusion protein.

SEQ ID NO:44 is a linker for a TNFRSF agonist fusion protein.

SEQ ID NO:45 is a linker for a TNFRSF agonist fusion protein.

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region (VH) for the 4-1BB agonist antibody 4B4-1-1 version 1.

SEQ ID NO:49 is a light chain variable region (VL) for the 4-1BB agonist antibody 4B4-1-1 version 1.

SEQ ID NO:50 is a heavy chain variable region (VH) for the 4-1BB agonist antibody 4B4-1-1 version 2.

SEQ ID NO:51 is a light chain variable region (VL) for the 4-1BB agonist antibody 4B4-1-1 version 2.

SEQ ID NO:52 is a heavy chain variable region (VH) for the 4-1BB agonist antibody H39E3-2.

SEQ ID NO:53 is a light chain variable region (VL) for the 4-1BB agonist antibody H39E3-2.

SEQ ID NO:54 is the amino acid sequence of human OX40.

SEQ ID NO:55 is the amino acid sequence of murine OX40.

SEQ ID NO:56 is the heavy chain for the OX40 agonist monoclonal antibody tavolixizumab (MEDI-0562).

SEQ ID NO:57 is the light chain for the OX40 agonist monoclonal antibody tavolixizumab (MEDI-0562).

SEQ ID NO:58 is the heavy chain variable region (VH) for the OX40 agonist monoclonal antibody tavolixizumab (MEDI-0562).

SEQ ID NO:59 is the light chain variable region (VL) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO:66 is the heavy chain for the OX40 agonist monoclonal antibody 11D4.

SEQ ID NO:67 is the light chain for the OX40 agonist monoclonal antibody 11D4.

SEQ ID NO:68 is the heavy chain variable region (VH) for the OX40 agonist monoclonal antibody 11D4.

SEQ ID NO:69 is the light chain variable region (VL) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO:76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region (VH) for the OX40 agonist monoclonal antibody 18D8.

SEQ ID NO:79 is the light chain variable region (VL) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region (VH) for the OX40 agonist monoclonal antibody Hu119-122.

SEQ ID NO:87 is the light chain variable region (VL) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region (VH) for the OX40 agonist monoclonal antibody Hu106-222.

SEQ ID NO:95 is the light chain variable region (VL) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO:103 is a soluble portion of OX40L polypeptide.

SEQ ID NO:104 is an alternative soluble portion of OX40L polypeptide.

SEQ ID NO:105 is the heavy chain variable region (VH) for the OX40 agonist monoclonal antibody 008.

SEQ ID NO:106 is the light chain variable region (VL) for the OX40 agonist monoclonal antibody 008.

SEQ ID NO:107 is the heavy chain variable region (VH) for the OX40 agonist monoclonal antibody 011.

SEQ ID NO:108 is the light chain variable region (VL) for the OX40 agonist monoclonal antibody 011.

SEQ ID NO:109 is the heavy chain variable region (VH) for the OX40 agonist monoclonal antibody 021.

SEQ ID NO:110 is the light chain variable region (VL) for the OX40 agonist monoclonal antibody 021.

SEQ ID NO:111 is the heavy chain variable region (VH) for the OX40 agonist monoclonal antibody 023.

SEQ ID NO:112 is the light chain variable region (VL) for the OX40 agonist monoclonal antibody 023.

SEQ ID NO:113 is the heavy chain variable region (VH) for an OX40 agonist monoclonal antibody.

SEQ ID NO:114 is the light chain variable region (VL) for an OX40 agonist monoclonal antibody.

SEQ ID NO:115 is the heavy chain variable region (VH) for an OX40 agonist monoclonal antibody.

SEQ ID NO:116 is the light chain variable region (VL) for an OX40 agonist monoclonal antibody.

SEQ ID NO:117 is the heavy chain variable region (VH) for a humanized OX40 agonist monoclonal antibody.

SEQ ID NO:118 is the heavy chain variable region (VH) for a humanized OX40 agonist monoclonal antibody.

SEQ ID NO:119 is the light chain variable region (VL) for a humanized OX40 agonist monoclonal antibody.

SEQ ID NO:120 is the light chain variable region (VL) for a humanized OX40 agonist monoclonal antibody.

SEQ ID NO:121 is the heavy chain variable region (VH) for a humanized OX40 agonist monoclonal antibody.

SEQ ID NO:122 is the heavy chain variable region (VH) for a humanized OX40 agonist monoclonal antibody.

SEQ ID NO:123 is the light chain variable region (VL) for a humanized OX40 agonist monoclonal antibody.

SEQ ID NO:124 is the light chain variable region (VL) for a humanized OX40 agonist monoclonal antibody.

SEQ ID NO:125 is the heavy chain variable region (VH) for an OX40 agonist monoclonal antibody.

SEQ ID NO:126 is the light chain variable region (VL) for an OX40 agonist monoclonal antibody.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$, to $1.5 \times 10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 (CCR7hi) and CD62L (CD62hi). The surface phenotype of central memory T cells also includes TCR, CD3, CD127 (IL-7R), and IL-15R. Transcription factors for central memory T cells include BCL-6, BCL-6B, MBD2, and BMI 1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7lo) and are heterogeneous or low for CD62L expression (CD62Llo). The surface phenotype of central memory T cells also includes TCR, CD3, CD127 (IL-7R), and IL-15R. Transcription factors for central memory T cells include BLIMP 1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3E. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706. A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706. Anti-CD3 antibodies also include the UHCT1 clone (commercially available from BioLegend, San Diego, CA, USA), also known as T3 and CD3ε.

TABLE 1

Amino acid sequences of muromonab.

| Identifier | Sequence (One-Letter Amino Acid Symbols) | |
|---|---|---|
| SEQ ID NO: 1 Muromonab heavy chain | QVQLQQSGAE LARPGASVKM SCKASGYTFT RYTMHWVKQR PGQGLEWIGY INPSRGYTNY | 60 |
| | NQHFKDKATL TTDKSSSTAY MQLSSLTSED SAVYYCARYY DDHYCLDYWG QGTTLTVSSA | 120 |
| | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQQW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREHYSKCSS | 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP THSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQHMIHQ | 120 |
| | HLSSRTHGSE DS | 132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, Respir. Res. 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG1 expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, Nat. Rev. Drug. Disc. 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" and its grammatical equivalents, as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 27, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

Methods of Treating Cancer

The compositions and methods involving TILs (and populations thereof) described herein can be used in a method for treating hyperproliferative disorders. In a preferred embodiment, they are for use in treating cancers. In a preferred embodiment, the invention provides a method of treating a cancer, wherein the cancer is metastatic melanoma. In a preferred embodiment, the invention provides a method of treating a cancer, wherein the cancer is metastatic double-refractory melanoma.

Methods of treating metastatic double-refractory melanoma in accordance with the present invention include administering to a patient in need thereof a therapeutic population of TILS derived from that patient's own tumor (autologous cell product). In certain embodiments, the cell product is composed of ≥90% CD45$^+$CD3$^+$ T cells. In some embodiments, the cell product is composed of ≥80%, ≥85%, ≥90%, ≥96%, ≥97%, ≥98%, or ≥99% CD45$^+$CD3$^+$ T cells. Natural killer (NK) cells and B cells may be present in the cell product, but generally represent less than 5%, less than 4%, less than 3%, less than 2%, or less than 1% of the total cells in the cell product.

For any of the treatment methods described herein, the route of administration of TIL therapy is generally by intravenous infusion. As described in further detail herein, this administration of TILs follows two or more prior systemic therapies. This administration of TIL therapy may also follow a nonmyeloablative lymphodeletion therapy such as cyclophosphamide and/or fludarbine. In further embodiments, IL-2 is administered to the patient following the TIL therapy.

As will be appreciated, the TILs used in the treatment methods described herein can be obtained and processed using methods known in the art and described herein. In certain exemplary embodiments, the therapeutic population TILs used in treatment methods of the invention are expanded from tumors resected from the patient with the metastatic double-refractory melanoma. Thus, the therapeutic population of TILs is "derived from" TILs from a tumor from the patient. The methods of expansion will in further embodiments include expansions such as those described herein in the section entitled "Methods of Expanding Tumor Infiltrating Lymphocytes." Briefly, such methods include the steps of resecting a tumor from a patient, the tumor comprising a first population of TILs, fragmenting the tumor, contacting the tumor fragments with a first cell culture medium to expand that first population of TILs into a second population of TILs, contacting the second population of TILs with a cell culture medium containing IL-2, OKT-3 (anti-CD3 antibody), and irradiated allogeneic peripheral blood mononuclear cells (PBMCs) to perform an expansion of that second population of TILs to obtain a third population of TILs, where a therapeutically effective portion of that third population of TILs can be administered to the patient. In general, the expansion of the second population into the third (therapeutic) population of cells is performed over a period of 14 days or less. In additional embodiments, methods of expanding TILs include those exemplified in co-pending applications WO2018/081473, filed Oct. 26, 2017; PCT/US2018/012605, filed Jan. 5, 2018; and PCT/US18/12633, filed Jan. 5, 2018, each of which is herein incorporated by reference in its entirety for all purposes and in particular for all teachings related to methods of expanding TILs from a tumor sample.

In a preferred embodiment, the invention provides a method of treating a cancer, wherein the cancer is metastatic double-refractory cutaneous melanoma.

In a preferred embodiment, the invention provides a method of treating a cancer, wherein the cancer is metastatic double-refractory uveal (ocular) melanoma.

As is discussed in further detail herein, the term "double-refractory melanoma" encompasses melanoma refractory to two or more prior systemic therapies. To be refractory to a prior systemic therapy is meant that the patient either had no response or progressed after receiving the prior systemic therapies.

In a preferred embodiment, the invention provides a method of treating a cancer, wherein the cancer is metastatic double-refractory melanoma refractory to at least two prior systemic therapies, where those two prior system therapies are not including neo-adjuvant or adjuvant therapies such as interferon-a. As will be appreciated, neo-adjuvant therapies encompass therapies given as a first step to reduce the size of a tumor before the main treatment is given. As will further be appreciated, adjuvant therapies include additional cancer treatment given after the primary treatment to lower the risk that the cancer will come back. The presently disclosed invention comprises TILs treatments that are third, fourth or fifth-line therapies after the melanoma has not responded to or has progressed after at least two prior primary therapies. In further embodiments, the patient has been previously treated with one additional prior line of systemic therapy prior to receiving TILs treatments in accordance with the methods described herein.

In a preferred embodiment, the invention provides a method of treating a cancer, wherein the cancer is metastatic double-refractory melanoma refractory to at least two prior systemic therapies, not including neo-adjuvant or adjuvant therapies such as interferon-a, wherein prior systemic therapies containing multiple agents, such as ipilimumab and nivolumab, or concurrent administration of multiple approved or experimental therapies, are counted as a single prior systemic therapy. In other words, the two prior systemic therapies may include primary therapies of combination treatments involving two or more therapies that are considered to be a single therapy. As will be appreciated, these combination therapies may include combinations of the same type of therapies (such as two checkpoint inhibitors), or they may include different types of therapies that are often provided in conjunction as a single therapy (such as radiation and chemotherapeutics).

In a preferred embodiment, the invention provides a method of treating a cancer, wherein the cancer is metastatic double-refractory melanoma refractory to (1) a checkpoint inhibitor and (2) at least one other prior systemic therapy.

In a preferred embodiment, the invention provides a method of treating a cancer, wherein the cancer is metastatic double-refractory melanoma refractory to (1) a BRAF inhibitor and (2) at least one other prior systemic therapy. In a further embodiment, the at least one other prior systemic therapy is a checkpoint inhibitor, and in a still further embodiment, the checkpoint inhibitor is a PD-1 inhibitor.

In a preferred embodiment, the invention provides a method of treating a cancer, wherein the cancer is metastatic double-refractory melanoma refractory to (1) a checkpoint inhibitor and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) a PD-1 inhibitor and (2) at least one other prior systemic therapy. In a further embodiment, the patient received no more than 4 doses of PD-1 inhibitor prior to receiving treatment by TILs in accordance with the present invention. In a still further embodiment, the patient received no more than 10, 9, 8, 7, 6, 5, 4, 3, or 2 doses of PD-1 inhibitor receiving treatment by TILs in accordance with the present invention.

In a preferred embodiment, the invention provides a method of treating a cancer, wherein the cancer is metastatic double-refractory melanoma refractory to (1) a PD-L1 inhibitor and (2) at least one other prior systemic therapy.

In a preferred embodiment, the invention provides a method of treating a cancer, wherein the cancer is metastatic double-refractory melanoma refractory to (1) a CTLA-4 inhibitor and (2) at least one other prior systemic therapy.

In a preferred embodiment, the invention provides a method of treating a cancer, wherein the cancer is metastatic double-refractory melanoma refractory to (1) a PD-1 inhibitor and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) a PD-L1 inhibitor and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) a CTLA-4 inhibitor and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) a checkpoint inhibitor and (2) aldesleukin or a biosimilar or variant thereof, including pegylated IL-2.

In a preferred embodiment, the invention provides a method of treating a cancer, wherein the cancer is metastatic double-refractory melanoma refractory to at least two checkpoint inhibitors given as separate prior therapies.

In a preferred embodiment, the invention provides a method of treating a cancer, wherein the cancer is metastatic double-refractory melanoma refractory to (1) pembrolizumab, or a biosimilar or variant thereof, and (2) at least one other prior systemic therapy.

In a preferred embodiment, the invention provides a method of treating a cancer, wherein the cancer is metastatic double-refractory melanoma refractory to (1) nivolumab, or a biosimilar or variant thereof, and (2) at least one other prior systemic therapy.

In a preferred embodiment, the invention provides a method of treating a cancer, wherein the cancer is metastatic double-refractory melanoma refractory to (1) ipilimumab, or a biosimilar or variant thereof, and (2) at least one other prior systemic therapy.

In a preferred embodiment, the invention provides a method of treating a cancer, wherein the cancer is metastatic double-refractory melanoma refractory to (1) a combination of nivolumab and ipilimumab, or biosimilars or variants thereof, and (2) at least one other prior systemic therapy.

In a preferred embodiment, the invention provides a method of treating a cancer, wherein the cancer is metastatic double-refractory melanoma refractory to (1) a checkpoint inhibitor and (2) aldesleukin or a biosimilar or variant thereof, including pegylated IL-2.

In a preferred embodiment, the invention provides a method of treating a cancer, wherein the cancer is metastatic double-refractory melanoma refractory to (1) pembrolizumab, or a biosimilar or variant thereof, and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) nivolumab, or a biosimilar or variant thereof, and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) ipilimumab, or a biosimilar or variant thereof, and (2) at least one other prior systemic therapy, wherein the one other prior systemic therapy is a combination of therapies.

In a preferred embodiment, the invention provides a method of treating a cancer, wherein the cancer is metastatic double-refractory melanoma refractory to (1) a combination of nivolumab and ipilimumab, or biosimilars or variants thereof, and (2) at least one other prior systemic therapy, wherein the one other prior systemic therapy is a combination of therapies.

In any of the foregoing embodiments, the metastatic double-refractory melanoma may be a cutaneous metastatic double-refractory melanoma.

As is described in further detail herein, the therapeutic population of TILs used in any of the treatment methods of the invention may be cryopreserved or non-cryopreserved. Cryopreserved TILs are produced according to methods known in the art or as described in further detail herein.

In accordance with any of the above-described embodiments, the double-refractory metastatic melanoma may be refractory to PD-1 inhibitors that can include for example antibodies that target PD-1, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other PD-1 antibodies include those disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, may also be among the systemic therapies to which the double-refractory melanoma is refractory. For example, antibodies that target PD-L1 and are in clinical trials or are approved and are commercially available include avelumab (EMD Serono, Pfizer, Bavencio®), durvalumab (MEDI4736, AstraZeneca, Imfinzi®), BMS-936559 (Bristol-Myers Squibb) and atezolizumab (MPDL3280A, Genentech, Tecentriq®). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response may serve as therapies to which the melanoma treated in accordance with methods of the present invention are refractory.

Similarly, the melanoma treated in accordance with the methods described herein may be refractory to BRAF inhibitors, including without limitation inhibitors that affect the BRAF protein directly or inhibitors that affect MEK. BRAF inhibitors include without limitation Vemurafenib (Zelboraf®) and dabrafenib (Tafinlar®), as well as GDC-0879, PLX-4720, or sorafenib (Nexavar®). MEK inhibitors include without limitation trametinib (Mekinist®) and cobimetinib (Cotellic®).

In certain embodiments and in accordance with any of the embodiments described herein, patients treated in accordance with the described invention may possess genetic makeups (or have tumors that possess genetic makeups) that indicate susceptibility or resistance to certain types of treatments. For example, patients may show low PDL1 expression, or they may (or may not) possess mutations in the BRAF gene. In specific embodiments, the treatments for double-refractory melanoma described herein are insensitive/agnostic to the BRAF status (e.g., the presence or absence of mutations in the BRAF gene). In some embodiments, patients may exhibit melanoma resistant to PD-1 or PD-L1 inhibitors. Mechanisms of resistance to PD-1 and PD-L1 inhibitors are known in the art, including resistance based on mutations within genes encoding Janus kinase 1 and Janus kinase 2 proteins mutations and resistance based on mutations within genes encoding beta-2-microglobulin, as well as other mutations, which are described, e.g., in Zaretsky, et al., Mutations associated with acquired resistance to PD-1 blockade in melanoma, *N. Engl. J. Med.* 2016, 375, 819-29, the disclosure of which is incorporated by reference herein.

In accordance with any of the embodiments discussed above, the TILs therapy provided to patients with double-refractory melanoma may include treatment with therapeutic populations of TILs alone or may include a combination treatment including TILs and one or more other therapies. For example, in some embodiments, the TILs produced as described herein can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008, 449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials or are approved and are commercially available include avelumab (EMD Serono, Pfizer, Bavencio®), durvalumab (MEDI4736, AstraZeneca, Imfinzi®), BMS-936559 (Bristol-Myers Squibb) and atezolizumab (MPDL3280A, Genentech, Tecentriq®). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs. In some embodiments, the patient administered the combination of TILs is co administered with an anti-PD-1 antibody when the patient has progressed or had no response to treatment by anti-PD-1 antibody alone. Similarly, TILs therapy may be co-administered with other therapies, such as CTLA-4 inhibitors, BRAF inhibitors, and any other therapies known in the art to be useful for treatment of melanoma.

As will be appreciated and in accordance with any of the treatment methods described above, any of the additional treatment modalities described herein, including BRAF inhibitors, MEK inhibitors, PD-1 inhibitors, PD-L1 inhibitors, and CTLA-4 inhibitors, include any embodiments of such inhibitors as well as any pharmaceutically acceptable salt thereof.

In an embodiment, a patient treated with TIL therapies disclosed herein exhibits an improved response to the response expected from a historical control, wherein the improved response is determined as overall response rate. In an embodiment, a patient treated with TIL therapies disclosed herein exhibits an improved response to the response expected from a historical control, wherein the improved response is determined as overall response rate, wherein the improvement in overall response rate is at least 5%, at least 10%, at least 15%, at least 20%, at least 25%, or at least 50%. In an embodiment, a patient treated with TIL therapies disclosed herein exhibits an improved response to the response expected from a historical control, wherein the improved response is determined as duration of response. In an embodiment, a patient treated with TIL therapies disclosed herein exhibits an improved response to the response expected from a historical control, wherein the improved response is determined as duration of response, wherein the improvement in duration of response is at least 5%, at least 10%, at least 15%, at least 20%, at least 25%, or at least 50%.

Non-Myeloablative Lymphodepletion with Chemotherapy

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the TILs of the invention.

In an embodiment, the invention provides a method of treating double-refractory melanoma with a population of TILs, wherein a patient is pre-treated with non-myeloablative chemotherapy prior to an infusion of TILs. In an embodiment, the non-myeloablative chemotherapy includes one or more chemotherapeutic agents. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance. In further embodiments, the IL-2 is administered between 3 and 24 hours following TIL infusion. In yet further embodiments, the IL-2 is administered following 3-30, 5-25, 7-20, 9-15 hours following TIL infusion. In still further embodiments, the IL-2 is administered at 500,000; 550,000; 600,000; 650,000; 700,000; 750,000; 800,000 IU/kg every 8-12 hours to physiologic tolerance over 5 days following TIL infusion.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 pg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide are together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

Methods of Expanding Tumor Infiltrating Lymphocytes

Figure 19A:
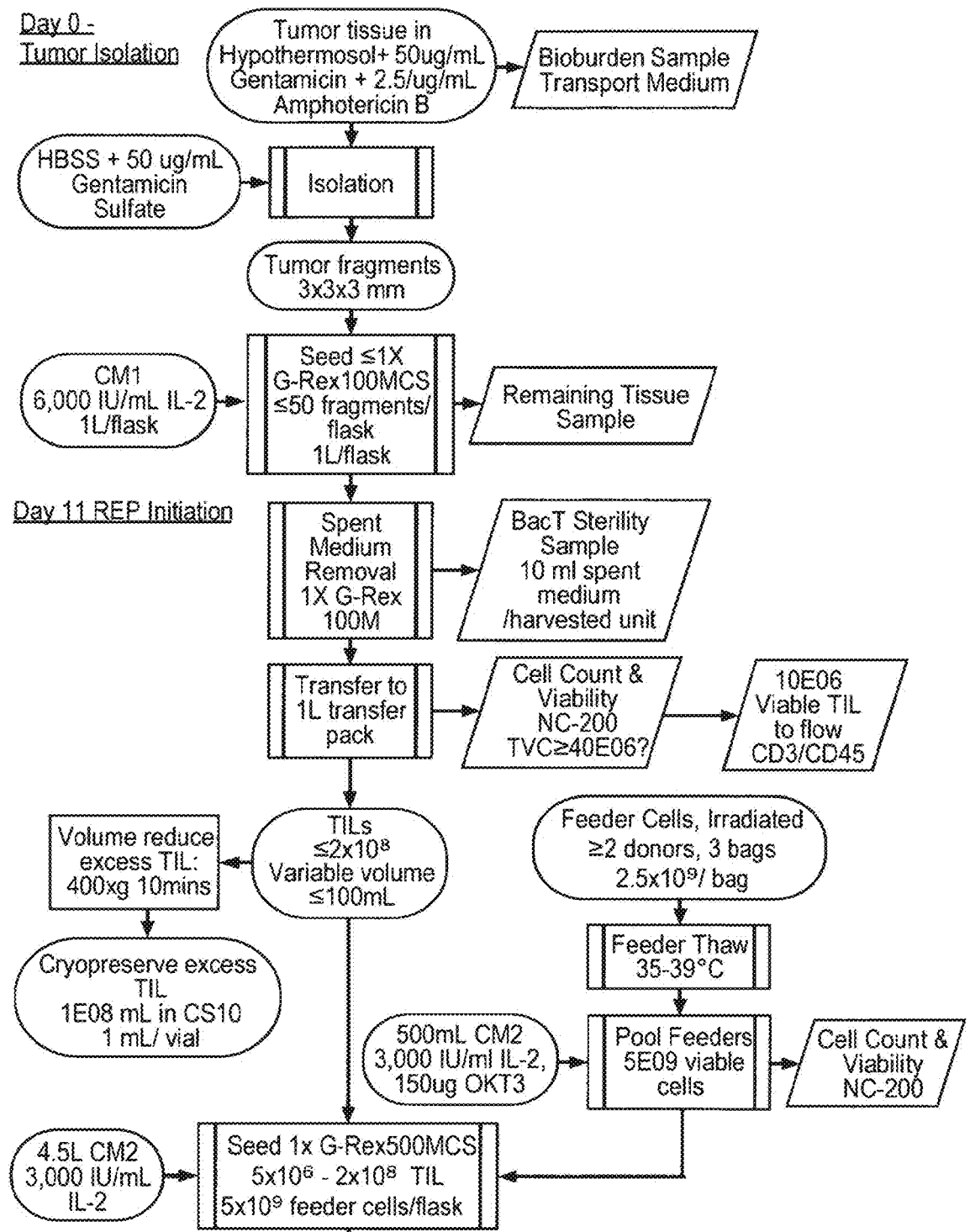
FIG. 19A-19C: Process Flow Chart of Process 2A.
Figure 19B:
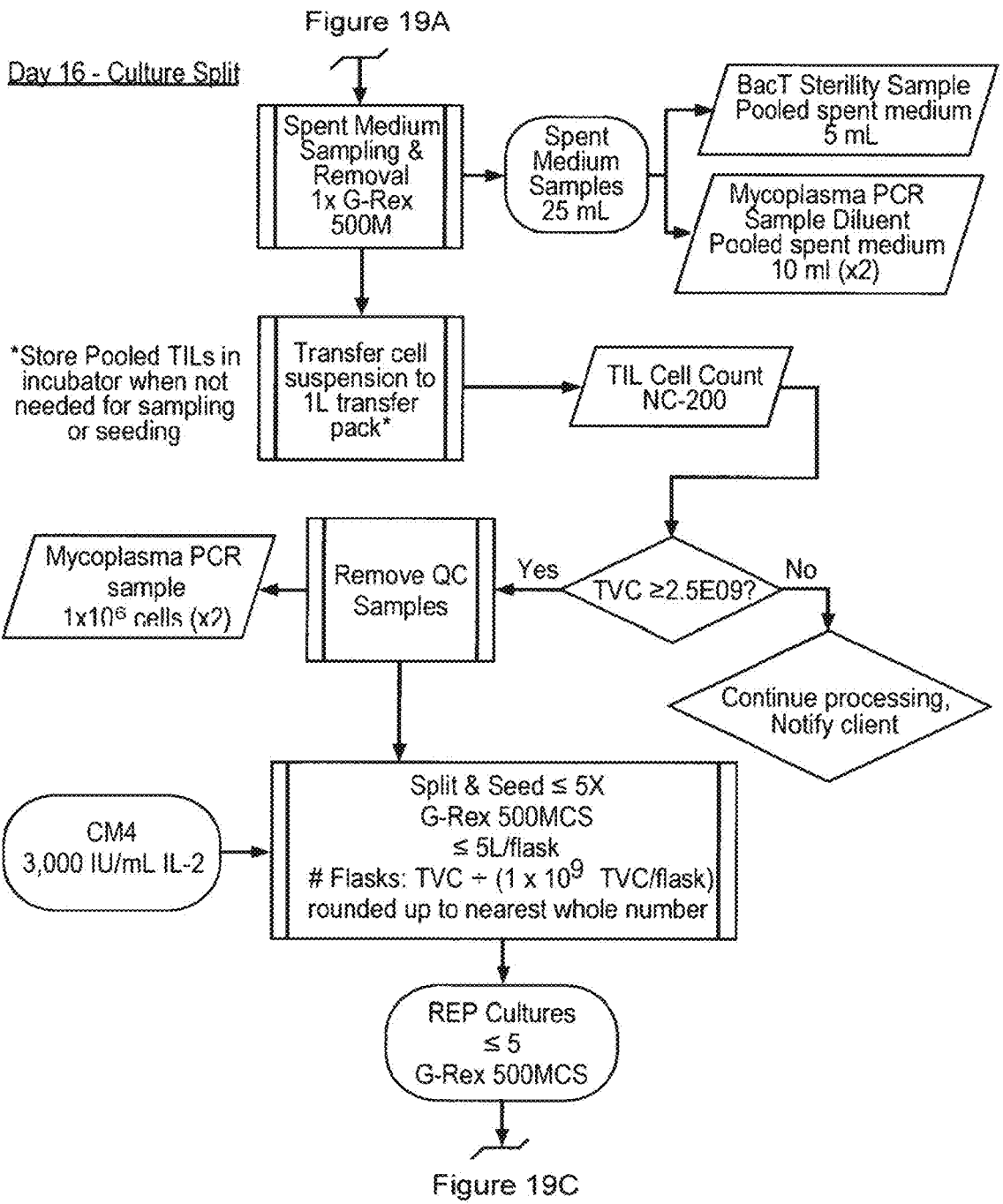
Figure 19C:
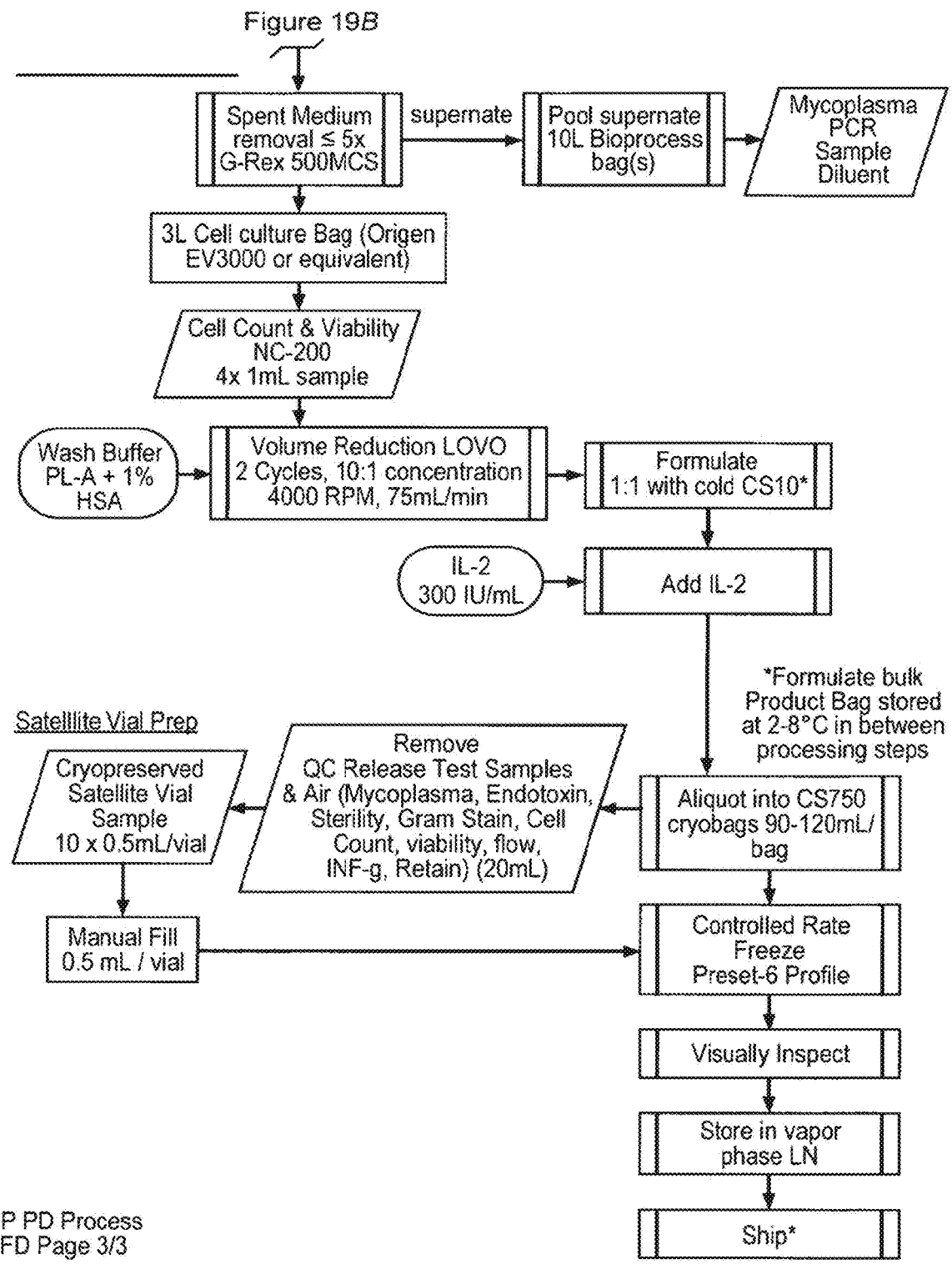
Figure 20:
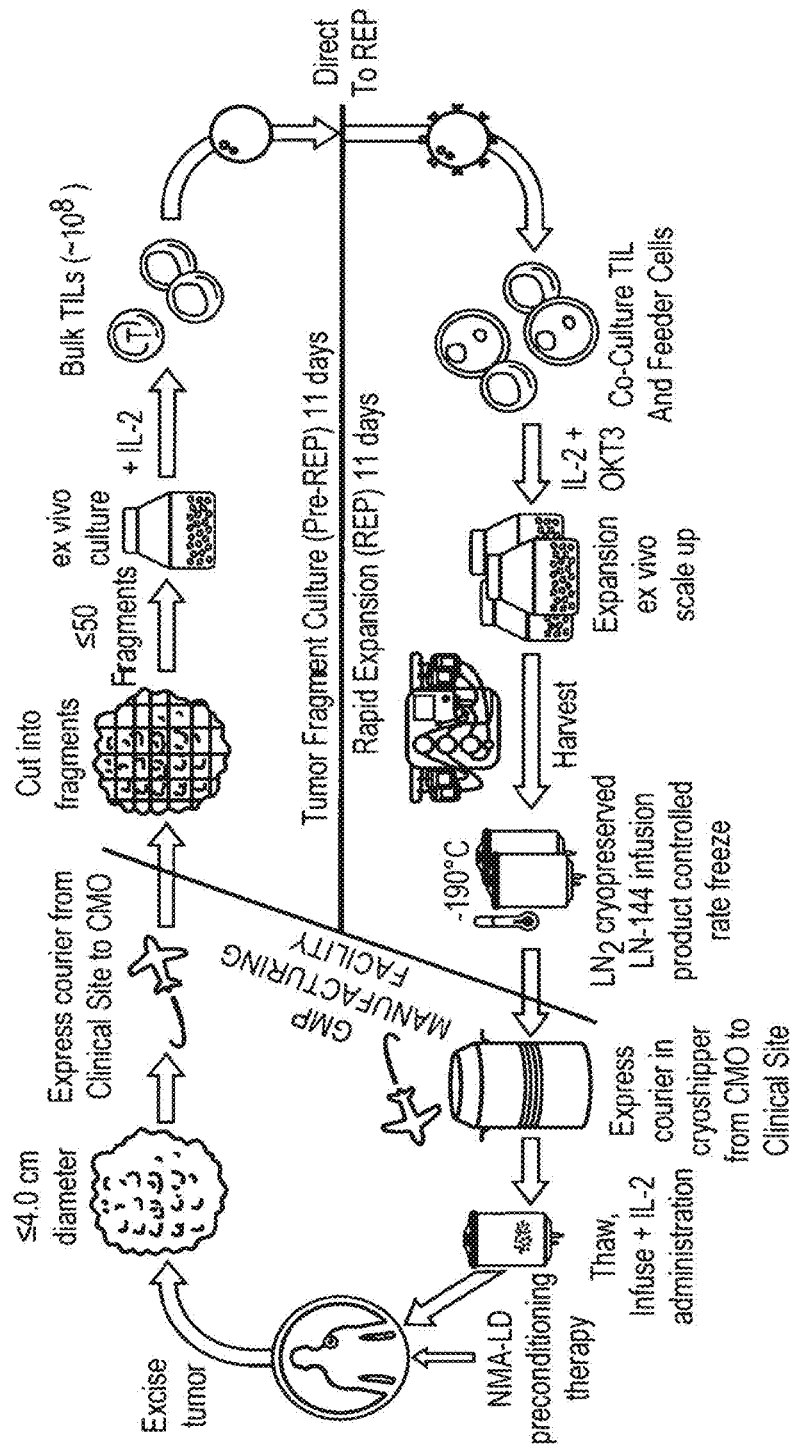
FIG. 20: Shows a diagram of an embodiment of a cryopreserved TIL exemplary manufacturing process (~22 days).
Figure 21:
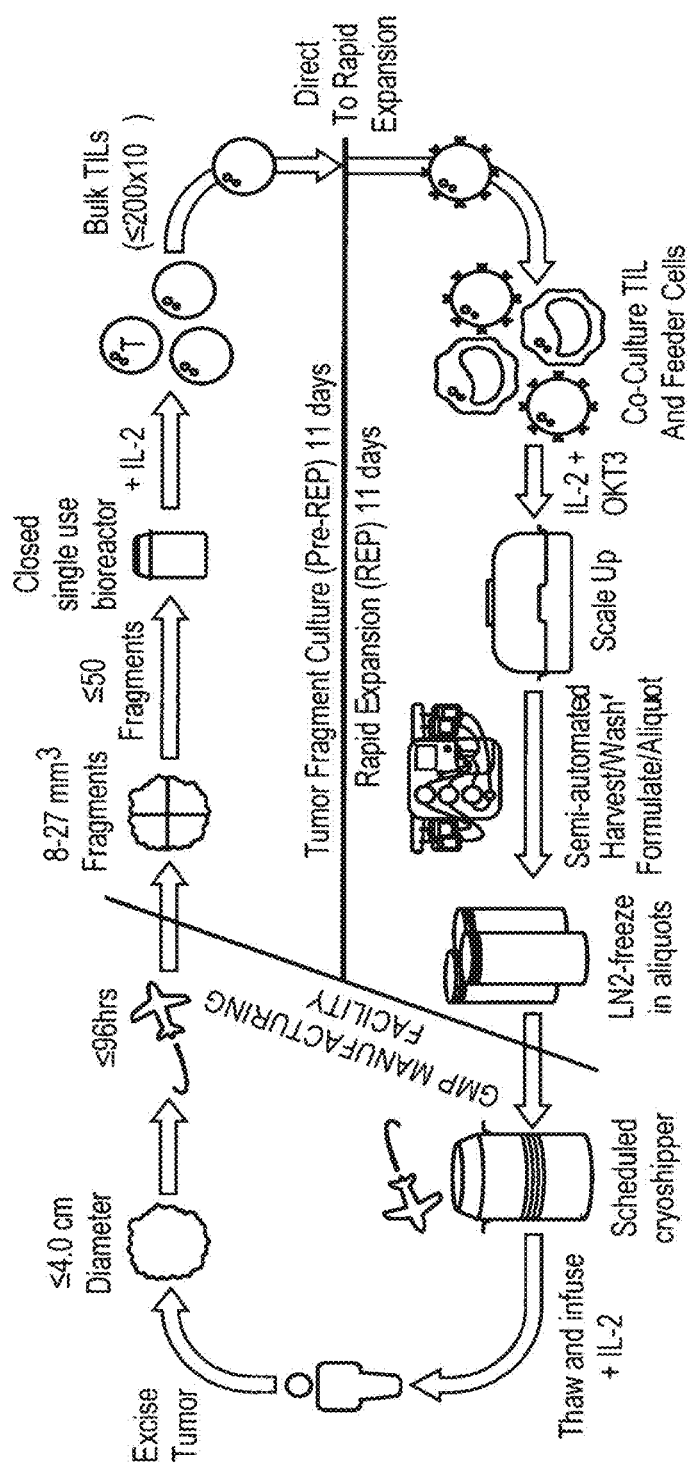
FIG. 21: Shows a diagram of an embodiment of process 2A, a 22-day process for TIL manufacturing.

An exemplary TIL process known as process 2A containing some of these features is depicted in FIG. 19, and some of the advantages of this embodiment of the present invention over process 1C are described in Figures F and G. An embodiment of process 2A is shown FIG. 18.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 18 as Step A) is shortened to 3 to 14 days and the second expansion (including processes referred to as the REP as well as processes shown in FIG. 18 as Step B) is shorted to 7 to 14 days, as discussed in detail below as well as in the examples and figures. In some embodiments, the first expansion (for example, an expansion described as Step B in FIG. 18) is shortened to 11 days and the second expansion (for example, an expansion as described in Step D in FIG. 18) is shortened to 11 days. In some embodiments, the combination of the first expansion and second expansion (for example, expansions described as Step B and Step D in FIG. 18) is shortened to 22 days, as discussed in detail below and in the examples and figures.

The "Step" Designations A, B, C, etc., below are in reference to FIG. 18 and in reference to certain embodiments described herein. The ordering of the Steps below and in FIG. 18 is exemplary and any combination or order of steps, as well as additional steps, repetition of steps, and/or omission of steps is contemplated by the present application and the methods disclosed herein.

Step A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 18). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 18.

Step B: First Expansion

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., Clin Cancer Res, 16:6122-6131 (2010); Huang et al., *J Immunother*, 28(3):258-267 (2005); Besser et al., *Clin Cancer Res*, 19(17): OF1-OF9 (2013); Besser et al., *J Immunother* 32:415-423 (2009); Robbins, et al., *J Immunol* 2004; 173: 7125-7130; Shen et al., J Immunother, 30:123-129 (2007); Zhou, et al., *J Immunother*, 28:53-62 (2005); and Tran, et al., J Immunother, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 18. In some embodiments, the TILs obtained by the present method exhibit an increase in the T-cell repertoire diversity as compared to freshly harvested TILs and/or TILs prepared using methods referred to as process 1C, as exemplified in FIG. 22 and/or FIG. 23. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 18, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 18, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40×10$^6$ viable tumor digest cells or 5-30 tumor fragments in 10-40 mL of CM with IL-2. Both the G-Rex10 and 24-well plates were incubated in a humidified incubator at 37° C. in 5% CO$_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of 20-30×10$^6$ IU/mg for a 1 mg vial. In some embodiments the IL-2 stock solution has a specific activity of 20×10$^6$ IU/mg for a 1 mg vial. In some embodiments the IL-2 stock solution has a specific activity of 25×10$^6$ IU/mg for a 1 mg vial. In some embodiments the IL-2 stock solution has a specific activity of 30×10$^6$ IU/mg for a 1 mg vial. In some embodiments, the IL-2 stock solution has a final concentration of 4-8×10$^6$ IU/mg of IL-2. In some embodiments, the IL-2 stock solution has a final concentration of 5-7×10$^6$ IU/mg of IL-2. In some embodiments, the IL-2 stock solution has a final concentration of 6×10$^6$ IU/mg of IL-2. In some embodiments, the IL-2 stock solution is prepare as described in Example 9. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-Rex10; Wilson Wolf Manufacturing, New Brighton, MN) (FIG. 1), each flask was loaded with 10-40× $10^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples. In some embodiments, the first expansion occurs in an initial cell culture medium or a first cell culture medium. In some embodiments, the initial cell culture medium or the first cell culture medium comprises IL-2.

In some embodiments, the first expansion (including processes such as for example those described in Step B of FIG. 18, which can include those sometimes referred to as the pre-REP) process is shortened to 3-14 days, as discussed in the examples and figures. In some embodiments, the first expansion (including processes such as for example those described in Step B of FIG. 18, which can include those sometimes referred to as the pre-REP) is shortened to 7 to 14 days, as discussed in the Examples and shown in FIGS. 4 and 5, as well as including for example, an expansion as described in Step B of FIG. 18. In some embodiments, the first expansion of Step B is shortened to 10-14 days. In some

TABLE 3

Amino acid sequences of muromonab (exemplary OKT-3 antibody)

| Identifier | Sequence (One-Letter Amino Acid Symbols) | |
| --- | --- | --- |
| SEQ ID NO: 1<br>Muromonab heavy<br>chain | QVQLQQSGAE LARPGASVKM SCKASGYTFT RYTMHWVKQR PGQGLEWIGY INPSRGYTNY<br>NQHFKDKATL TTDKSSSTAY MQLSSLTSED SAVYYCARYY DDHYCLDYWG QGTTLTVSSA<br>KTTAPSVYPL APVCGGTTGS SVTLGCLVKG YFPEPVTLTW NSGSLSSGVH TFPAVLQSDL<br>YTLSSSVTVT SSTWPSQSIT CNVAHPASST KVDKKIEPRP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 2<br>Muromonab light<br>chain | QIVLTQSPAI MSASPGEKVT MTCSASSSVS YMNWYQQKSG TSPKRWIYDT SKLASGVPAH<br>FRGSGSGTSY SLTISGMEAE DAATYYCQQW SSNPFTFGSG TKLEINRADT APTVSIFPPS<br>SEQLTSGGAS VVCFLNNFYP KDINVKWKID GSERQNGVLN SWTDQDSKDS TYSMSSTLTL<br>TKDEYERHNS YTCEATHKTS TSPIVKSFNR NEC | 60<br>120<br>180<br>213 | embodiments, the first expansion is shortened to 11 days, as discussed in, for example, an expansion as described in Step B of FIG. 18.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 18, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 18 and as described herein.

In some embodiments, the first expansion (including processes referred to as the pre-REP; for example, Step B according to FIG. 18) process is shortened to 3 to 14 days, as discussed in the examples and figures. In some embodiments, the first expansion of Step B is shortened to 7 to 14 days. In some embodiments, the first expansion of Step B is shortened to 10 to 14 days. In some embodiments, the first expansion is shortened to 11 days.

In some embodiments, the first expansion, for example, Step B according to FIG. 18, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Step C: First Expansion to Second Expansion Transition

In some cases, the bulk TIL population obtained from the first expansion, including for example the TIL population obtained from for example, Step B as indicated in FIG. 18, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 18) are stored until phenotyped for selection. In some embodiments, the TILs obtained from the first expansion (for example, from Step B as indicated in FIG. 18) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 18). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 18, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Cytokines

The expansion methods described herein generally use culture media with high doses of a cytokine, in particular IL-2, as is known in the art.

Alternatively, using combinations of cytokines for the rapid expansion and/or second expansion of TILS is additionally possible, with combinations of two or more of IL-2, IL-15 and IL-21 as is generally outlined in International Publication No. WO 2015/189356 and International Publication No. WO 2015/189357, hereby expressly incorporated by reference in their entirety for all purposes and in particular for all teachings related to use of cytokines in cell expansion methods. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

TABLE 4

Amino acid sequences of interleukins.

| Identifier | Sequence (One-Letter Amino Acid Symbols) | | | | | |
|---|---|---|---|---|---|---|
| SEQ ID NO: 3 recombinant human IL-2 (rhIL-2) | MAPTSSSTKK EEELKPLEEV RWITFCQSII | TQLQLEHLLL LNLAQSKNFH STLT | DLQMILNGIN LRPRDLISNI | NYKNPKLTRM NVIVLELKGS | LTFKFYMPKK ETTFMCEYAD | ATELKHLQCL ETATIVEFLN | 60 120 134 |
| SEQ ID NO: 4 Aldesleukin | PTSSSTKKTQ ELKPLEEVLN ITFSQSIIST | LQLEHLLLDL LAQSKNFHLR LT | QMILNGINNY PRDLISNINV | KNPKLTRMLT IVLELKGSET | FKFYMPKKAT TFMCEYADET | ELKHLQCLEE ATIVEFLNRW | 60 120 132 |
| SEQ ID NO: 5 recombinant human IL-4 (rhIL-4) | MHKCDITLQE EKDTRCLGAT MREKYSKCSS | IIKTLNSLTE AQQFHRHKQL | QKTLCTELTV IRFLKRLDRN | TDIFAASKNT LWGLAGLNSC | TEKETFCRAA PVKEANQSTL | TVLRQFYSHH ENFLERLKTI | 60 120 130 |
| SEQ ID NO: 6 recombinant human IL-7 (rhIL-7) | MDCDIEGKDG ARKLRQFLKM KEQKKLNDLC | KQYESVLMVS NSTGDFDLHL FLKRLLQEIK | IDQLLDSMKE LKVSEGTTIL TCWNKILMGT | IGSNCLNNEF LNCTGQVKGR KEH | NFFKRHICDA KPAALGEAQP | NKEGMFLFRA TKSLEENKSL | 60 120 153 |
| SEQ ID NO: 7 recombinant human IL-15 (rhIL-15) | MNWVNVISDL HDTVENLIIL | KKIEDLIQSM ANNSLSSNGN | HIDATLYTES VTESGCKECE | DVHPSCKVTA ELEEKNIKEF | MKCFLLELQV LQSFVHIVQM | ISLESGDASI FINTS | 60 115 |

TABLE 4-continued

Amino acid sequences of interleukins.

| Identifier | Sequence (One-Letter Amino Acid Symbols) | |
|---|---|---|
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

Step D: Second Expansion

In some embodiments, the TIL cell population is expanded in number after harvest and initial bulk processing for example, after Step A and Step B, and the transition referred to as Step C, as indicated in FIG. 18). This further expansion is referred to herein as the second expansion, which can include expansion processes generally referred to in the art as a rapid expansion process (REP; as well as processes as indicated in Step D of FIG. 18). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 18) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 18). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium for the second expansion step further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 18, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 18 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about $1\times10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0\times10^6$ cells/mL.

In an embodiment, the second expansion (which can include expansions referred to as REP, as well as those referred to in Step D of FIG. 18) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILS being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA).

In some embodiments, the second expansion (including expansions referred to as REP) of TIL can be performed using T-175 flasks and gas-permeable bags as previously described (Tran K Q, Zhou J, Durflinger K H, et al., 2008, J Immunother., 31:742-751, and Dudley M E, Wunderlich J R, Shelton T E, et al. 2003, J Immunother., 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 $cm^2$ gas-permeable silicon bottoms (G-Rex 100, Wilson Wolf) (FIG. 1), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 18, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Feeder Cells and Antigen Presenting Cells

In an embodiment, the second expansion procedures described herein (for example including expansion such as those described in Step D from FIG. 18, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$, feeder cells to about $100 \times 10^6$ TILs. In another embodiment, the second expansion procedures described herein require a ratio of about $2.5 \times 10^9$, feeder cells to about $50 \times 10^6$ TILs. In yet another embodiment, the second expansion procedures described herein require about $2.5 \times 10^9$, feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the second expansion as a replacement for, or in combination with, PBMCs.

Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

Step E: Harvest TILS

After the second expansion step, cells can be harvested. In some embodiments the TILs are harvested after one, two, three, four or more expansion steps, for example as provided in FIG. 18. In some embodiments the TILs are harvested after two expansion steps, for example as provided in FIG. 18.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 18, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-Mc-Neil, Raritan, NJ or Miltenyi Biotech, Auburn, CA).

TABLE 5

| Amino acid sequences of muromonab (exemplary OKT-3 antibody) | | | | | | |
|---|---|---|---|---|---|---|
| Identifier | Sequence (One-Letter Amino Acid Symbols) | | | | | |
| SEQ ID NO: 1 Muromonab heavy chain | QVQLQQSGAE NQKFKDKATL KTTAPSVYPL YTLSSSVTVT PSVFLFPPKP STYRVVSVLT LTKNQVSLTC QQGNVFSCSV | LARPGASVKM TTDKSSSTAY APVCGGTTGS SSTWPSQSIT KDTLMISRTP VLHQDWLNGK LVKGFYPSDI MHEALHNHYT | SCKASGYTFT MQLSSLTSED SVTLGCLVKG CNVAHPASST EVTCVVVDVS EYKCKVSNKA AVEWESNGQP QKSLSLSPGK | RYTMHWVKQR SAVYYCARYY YFPEPVTLTW KVDKKIEPRP HEDPEVKFNW LPAPIEKTIS ENNYKTTPPV | PGQGLEWIGY DDHYCLDYWG NSGSLSSGVH KSCDKTHTCP YVDGVEVHNA KAKGQPREPQ LDSDGSFFLY | INPSRGYTNY QGTTLTVSSA TFPAVLQSDL PCPAPELLGG KTKPREEQYN VYTLPPSRDE SKLTVDKSRW | 60 120 180 240 300 360 420 450 |
| SEQ ID NO: 2 Muromonab light chain | QIVLTQSPAI FRGSGSGTSY SEQLTSGGAS TKDEYERHNS | MSASPGEKVT SLTISGMEAE VVCFLNNFYP YTCEATHKTS | MTCSASSSVS DAATYYCQQW KDINVKWKID TSPIVKSFNR | YMNWYQQKSG SSNPFTFGSG GSERQNGVLN NEC | TSPKRWIYDT TKLEINRADT SWTDQDSKDS | SKLASGVPAH APTVSIFPPS TYSMSSTLTL | 60 120 180 213 |

In some embodiments, Step E according to FIG. 18, is performed according to the processes described in Example 7. In some embodiments, the closed system is accessed via syringes under sterile conditions in order to maintain the sterility and closed nature of the system. In some embodiments, a closed system as described in Example 7 is employed.

In some embodiments, TILs are harvested according to the methods described in the Examples.

Step F: Final Formulation/Transfer to Infusion Bag

After Steps A through E as provided in an exemplary order in FIG. 18 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

Optional Cell Medium Components

1. Anti-CD3 Antibodies

In some embodiments, the culture media used in expansion methods described herein (including those referred to as REP, see for example, FIG. 18) also includes an anti-CD3 antibody. An anti-CD3 antibody in combination with IL-2

2. 4-1BB (CD137) Agonists

In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG 1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in TABLE 6.

TABLE 6

Amino acid sequences of 4-1BB antigens.

| Identifier | Sequence (One-Letter Amino Acid Symbols) | | | | | |
|---|---|---|---|---|---|---|
| SEQ ID NO: 9 human 4-1BB, Tumor necrosis factor receptor superfamily, member 9 (*Homo sapiens*) | MGNSCYNIVA TCDICRQCKG CFGTFNDQKR PGHSPQIISF CSCRFPEEEE | TLLLVLNFER VFRTRKECSS GICRPWTNCS FLALTSTALL GGCEL | TRSLQDPCSN TSNAECDCTP LDGKSVLVNG FLLFFLTLRF | CPAGTFCDNN GFHCLGAGCS TKERDVVCGP SVVKRGRKKL | RNQICSPCPP MCEQDCKQGQ SPADLSPGAS LYIFKQPFMR | NSFSSAGGQR ELTKKGCKDC SVTPPAPARE PVQTTQEEDG | 60 120 180 240 255 |
| SEQ ID NO: 10 murine 4-1BB, Tumor necrosis factor receptor superfamily, member 9 (*Mus musculus*) | MGNNCYNVVV CNICRVCAGY LGTFNDQNGT GHSLQVLTLF CRCPQEEEGG | IVLLLVGCEK FRFKKFCSST GVCRPWTNCS LALTSALLLA GGGYEL | VGAVQNSCDN HNAECECIEG LDGRSVLKTG LIFITLLFSV | CQPGTFCRKY FHCLGPQCTR TTEKDVVCGP LKWIRKKFPH | NPVCKSCPPS CEKDCRPGQE PVVSFSPSTT IFKQPFKKTT | TFSSIGGQPN LTKQGCKTCS ISVTPEGGPG GAAQEEDACS | 60 120 180 240 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5\times10^5$ 1/M·s or faster, binds to human or murine 4-1BB with a $k_{assoc}$ of about $7.5\times10^5$ 1/M·s or faster, binds to human or murine 4-1BB with a $k_{assoc}$ of about $8\times10^5$ 1/M·s or faster, binds to human or murine 4-1BB with a $k_{assoc}$ of about $8.5\times10^5$ 1/M·s or faster, binds to human or murine 4-1BB with a $k_{assoc}$ of about $9\times10^5$ 1/M·s or faster, binds to human or murine 4-1BB with a $k_{assoc}$ of about $9.5\times10^5$ 1/M·s or faster, or binds to human or murine 4-1BB with a $k_{assoc}$ of about $1\times10^6$ 1/M·s or faster.

In some embodiments, the compositions, processes and methods described include a 4-1BB agonist that binds to human or murine 4-1BB with a $k_{dissoc}$ of about $2\times10^{-5}$ 1/s or slower, binds to human or murine 4-1BB with a $k_{dissoc}$ of about $2.1\times10^{-5}$ 1/s or slower, binds to human or murine 4-1BB with a $k_{dissoc}$ of about $2.2\times10^{-5}$ 1/s or slower, binds to human or murine 4-1BB with a $k_{dissoc}$ of about $2.3\times10^{-5}$ 1/s or slower, binds to human or murine 4-1BB with a $k_{dissoc}$ of about $2.4\times10^{-5}$ 1/s or slower, binds to human or murine 4-1BB with a $k_{dissoc}$ of about $2.5\times10^{-5}$ 1/s or slower, binds to human or murine 4-1BB with a $k_{dissoc}$ of about $2.6\times10^{-5}$ 1/s or slower or binds to human or murine 4-1BB with a $k_{dissoc}$ of about $2.7\times10^{-5}$ 1/s or slower, binds to human or murine 4-1BB with a $k_{dissoc}$ of about $2.8\times10^{-5}$ 1/s or slower, binds to human or murine 4-1BB with a $k_{dissoc}$ of about $2.9\times10^{-5}$ 1/s or slower, or binds to human or murine 4-1BB with a $k_{dissoc}$ of about $3\times10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[Homo sapiens TNFRSF9 (tumor necrosis factor receptor (TNFR) superfamily member 9, 4-1BB, T cell antigen ILA, CD137)], Homo sapiens (fully human) monoclonal antibody. The amino acid sequences of utomilumab are set forth in Table 7. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., Cancer Immunolog. & Immunother. 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises VH and VL regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

tions 23'-88' ($V_H$-$V_L$) and 136'-196' ($C_H$1-$C_L$) (and at positions 23'''-88''' and 136'''-196'''); interchain heavy chain-heavy chain disulfide bridges at positions 227-227'' and 230-230''; and interchain heavy chain-light chain disulfide bridges at 135-216' and 135''-216'''. The preparation and properties of urelumab and its variants and fragments are

TABLE 7

Amino acid sequences for 4-1BB agonist antibodies related to utomilumab.

| Identifier | Sequence (One-Letter Amino Acid Symbols) | | | | | |
|---|---|---|---|---|---|---|
| SEQ ID NO: 11 heavy chain for utomilumab | EVQLVQSGAE SPSFQGQVTI GPSVFPLAPC LSSVVTVPSS KPKDTLMISR LTVVHQDWLN TCLVKGFYPS SVMHEALHNH | VKKPGESLRI SADKSISTAY SRSTSESTAA NFGTQTYTCN TPEVTCVVVD GKEYKCKVSN DIAVEWESNG YTQKSLSLSP | SCKGSGYSFS LQWSSLKASD LGCLVKDYFP VDHKPSNTKV VSHEDPEVQF KGLPAPIEKT QPENNYKTTP G | TYWISWVRQM TAMYYCARGY EPVTVSWNSG DKTVERKCCV NWYVDGVEVH ISKTKGQPRE PMLDSDGSFF | PGKGLEWMGK GIFDYWGQGT ALTSGVHTFP ECPPCPAPPV NAKTKPREEQ PQVYTLPPSR LYSKLTVDKS | IYPGDSYTNY LVTVSSASTK AVLQSSGLYS AGPSVFLFPP FNSTFRVVSV EEMTKNQVSL RWQQGNVFSC | 60 120 180 240 300 360 420 441 |
| SEQ ID NO: 12 light chain for utomilumab | SYELTQPPSV FSGSNSGNTA PPSSEELQAN SLTPEQWKSH | SVSPGQTASI TLTISGTQAM KATLVCLISD RSYSCQVTHE | TCSGDNIGDQ DEADYYCATY FYPGAVTVAW GSTVEKTVAP | YAHWYQQKPG TGFGSLAVFG KADSSPVKAG TECS | QSPVLVIYQD GGTKLTVLGQ VETTTPSKQS | KNRPSGIPER PKAAPSVTLF NNKYAASSYL | 60 120 180 214 |
| SEQ ID NO: 13 heavy chain variable region for utomilumab | EVQLVQSGAE YSPSFQGQVT | VKKPGESLRI ISADKSISTA | SCKGSGYSFS YLQWSSLKAS | TYWISWVRQM DTAMYYCARG | PGKGLEWMG YGIFDYWGQ | KIYPGDSYTN GTLVTVSS | 60 118 |
| SEQ ID NO: 14 light chain variable region for utomilumab | SYELTQPPSV FSGSNSGNTA | SVSPGQTASI TLTISGTQAM | TCSGDNIGDQ DEADYYCATY | YAHWYQQKPG TGFGSLAVFG | QSPVLVIYQD GGTKLTVL | KNRPSGIPER | 60 108 |
| SEQ ID NO: 15 heavy chain CDR1 for utomilumab | STYWIS | | | | | | 6 |
| SEQ ID NO: 16 heavy chain CDR2 for utomilumab | KIYPGDSYTN YSPSFQG | | | | | | 17 |
| SEQ ID NO: 17 heavy chain CDR3 for utomilumab | RGYGIFDY | | | | | | 8 |
| SEQ ID NO: 18 light chain CDR1 for utomilumab | SGDNIGDQYA H | | | | | | 11 |
| SEQ ID NO: 19 light chain CDR2 for utomilumab | QDKNRPS | | | | | | 7 |
| SEQ ID NO: 20 light chain CDR3 for utomilumab | ATYTGFGSLA V | | | | | | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 7. Urelumab comprises N-glycosylation sites at positions 298 (and 298''); heavy chain intrachain disulfide bridges at positions 22-95 ($V_H$-$V_L$), 148-204 ($C_H$1-$C_L$), 262-322 ($C_H$2) and 368-426 ($C_H$3) (and at positions 22''-95'', 148''-204'', 262''-322'', and 368''-426''); light chain intrachain disulfide bridges at positions described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http:/dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 8

Amino acid sequences for 4-1BB agonist antibodies related to urelumab.

| Identifier | Sequence (One-Letter Amino Acid Symbols) | | | | | | |
|---|---|---|---|---|---|---|---|
| SEQ ID NO: 21 heavy chain for urelumab | QVQLQQWGAG | LLKPSETLSL | TCAVYGGSFS | GYYWSWIRQS | PEKGLEWIGE | INHGGYVTYN | 60 |
| | PSLESRVTIS | VDTSKNQFSL | KLSSVTAADT | AVYYCARDYG | PGNYDWYFDL | WGRGTLVTVS | 120 |
| | SASTKGPSVF | PLAPCSRSTS | ESTAALGCLV | KDYFPEPVTV | SWNSGALTSG | VHTFPAVLQS | 180 |
| | SGLYSLSSVV | TVPSSSLGTK | TYTCNVDHKP | SNTKVDKRVE | SKYGPPCPPC | PAPEFLGGPS | 240 |
| | VFLFPPKPKD | TLMISRTPEV | TCVVVDVSQE | DPEVQFNWYV | DGVEVHNAKT | KPREEQFNST | 300 |
| | YRVVSVLTVL | HQDWLNGKEY | KCKVSNKGLP | SSIEKTISKA | KGQPREPQVY | TLPPSQEEMT | 360 |
| | KNQVSLTCLV | KGFYPSDIAV | EWESNGQPEN | NYKTTPPVLD | SDGSFFLYSR | LTVDKSRWQE | 420 |
| | GNVFSCSVMH | EALHNHYTQK | SLSLSLGK | | | | 448 |
| SEQ ID NO: 22 light chain for urelumab | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPPALTF | CGGTKVEIKR | TVAAPSVFIF | 120 |
| | PPSDEQLKSG | TASVVCLLNN | FYPREAKVQW | KVDNALQSGN | SQESVTEQDS | KDSTYSLSST | 180 |
| | LTLSKADYEK | HKVYACEVTH | QGLSSPVTKS | FNRGEC | | | 216 |
| SEQ ID NO: 23 variable heavy chain for urelumab | MKHLWFFLLL | VAAPRWVLSQ | VQLQQWGAGL | LKPSETLSLT | CAVYGGSFSG | YYWSWIRQSP | 60 |
| | EKGLEWIGEI | NHGGYVTYNP | SLESRVTISV | DTSKNQFSLK | LSSVTAADTA | VYYCARDYGP | 120 |

TABLE 8-continued

Amino acid sequences for 4-1BB agonist antibodies related to urelumab.

| Identifier | Sequence (One-Letter Amino Acid Symbols) | |
|---|---|---|
| SEQ ID NO: 24 variable light chain for urelumab | MEAPAQLLFL LLLWLPDTTG EIVLTQSPAT LSLSPGERAT LSCRASQSVS SYLAWYQQKP<br>GQAPRLLIYD ASNRATGIPA RFSGSGSGTD FTLTISSLEP EDFAVYYCQQ | 60<br>110 |
| SEQ ID NO: 25 heavy chain CDR1 for urelumab | GYYWS | 5 |
| SEQ ID NO: 26 heavy chain CDR2 for urelumab | EINHGGYVTY NPSLES | 16 |
| SEQ ID NO: 27 heavy chain CDR3 for urelumab | DYGPGNYDWY FDL | 13 |
| SEQ ID NO: 28 light chain CDR1 for urelumab | RASQSVSSYL A | 11 |
| SEQ ID NO: 29 light chain CDR2 for urelumab | DASNRAT | 7 |
| SEQ ID NO: 30 light chain CDR3 for urelumab | QQRSDWPPAL T | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20114.9-IgG1 (BMS-663031)), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3113 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof:

In structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second triavelent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., Antibodies, 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 9

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31 Fc domain | KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 60 120 180 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SEQ ID NO:43 to SEQ ID NO:45.

TABLE 10

Amino acid sequences for TNFRSF fusion proteins, including 4-1BB fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG | 60 120 180 240 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 9, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 11, wherein the $V_H$ and $V_L$ domains are connected by a linker.

TABLE 11

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46<br>4-1BBL | MEYASDASLD PEAPWPPAPR ARACRVLPWA LVAGLLLLLL LAAACAVFLA CPWAVSGARA<br>SPGSAASPRL REGPELSPDD PAGLLDLRQG MFAQLVAQNV LLIDGPLSWY SDPGLAGVSL<br>TGGLSYKEDT KELVVAKAGV YYVFFQLELR RVVAGEGSGS VSLALHLQPL RSAAGAAALA<br>LTVDLPPASS EARNSAFGFQ GRLLHLSAGQ RLGVHLHTEA RARHAWQLTQ GATVLGLFRV<br>TPEIPAGLPS PRSE | 60<br>120<br>180<br>240<br>254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ<br>LELRRVVAGE GSGSVSLALH LQPLRSAAGA AALALTVDLP PASSEARNSA FGFQGRLLHL<br>SAGQRLGVHL HTEARARHAW QLTQGATVLG LFRVTPEIPA GLPSPRSE | 60<br>120<br>168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVS | 60<br>118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIK | 60<br>107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVSA | 60<br>119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIKR | 60<br>108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP<br>GKGLEWVADI KNDGSYTNYA PSLTNRFTIS RDNAKNSLYL QMNSLRAEDT AVYYCARELT | 60<br>120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL<br>WYQQKPGQPP KLLIYYASTR QSGVPDRFSG SGSGTDFTLT ISSLQAEDVA | 60<br>110 | structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 12.

TABLE 12

Amino acid sequences of OX40 antigens.

| Identifier | Sequence (One-Letter Amino Acid Symbols) | |
|---|---|---|
| SEQ ID NO: 54 human OX40 (Homo sapiens) | MCVGARRLGR GPCAALLLLG LGLSTVTGLH CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPSTRPVEVP GGRAVAAILG LGLVLGLLGP LAILLALYLL RRDQRLPPDA HKPPGGGSFR TPIQEEQADA HSTLAKI | 60 120 180 240 277 |

TABLE 12-continued

Amino acid sequences of OX40 antigens.

| Identifier | Sequence (One-Letter Amino Acid Symbols) | |
|---|---|---|
| SEQ ID NO: 55<br>murine OX40<br>(Mus musculus) | MYVWVQQPTA LLLLGLTLGV TARRLNCVKH TYPSGHKCCR ECQPGHGMVS RCDHTRDTLC<br>HPCETGFYNE AVNYDTCKQC TQCNHRSGSE LKQNCTPTQD TVCRCRPGTQ PRQDSGYKLG<br>VDCVPCPPGH FSPGNNQACK PWTNCTLSGK QTRHPASDSL DAVCEDRSLL ATLLWETQRP<br>TFRPTTVQST TVWPRTSELP SPPTLVTPEG PAFAVLLGLG LGLLAPLTVL LALYLLRKAW<br>RLPNTPKPCW GNSFRTPIQE EHTDAHFTLA KI | 60<br>120<br>180<br>240<br>272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[Homo sapiens TNFRSF4 (tumor necrosis factor receptor (TNFR) superfamily member 4, OX40, CD134)], humanized and chimeric monoclonal antibody. The amino acid sequences of tavolixizumab are set forth in Table 13. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'''-88''' and 134'''-194'''); interchain heavy chain-heavy chain disulfide bridges at positions 230-230" and 233-233"; and interchain heavy chain-light chain disulfide bridges at 224-214' and 224"-214'''. Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 13

Amino acid sequences for OX40 agonist antibodies related to tavolixizumab.

| Identifier | Sequence (One-Letter Amino Acid Symbols) | |
|---|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRE | 360 |
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 57 light chain for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQP EDFATYYCQQ GSALPWTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVT | 118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQP EDFATYYCQQ GSALPWTFGQ GTKVEIKR | 108 |
| SEQ ID NO: 60 heavy chain CDR1 for tavolixizumab | GSFSSGYWN | 9 |
| SEQ ID NO: 61 heavy chain CDR2 for tavolixizumab | YIGYISYNGI TYH | 13 |

TABLE 13-continued

Amino acid sequences for OX40 agonist antibodies related to tavolixizumab.

| Identifier | Sequence (One-Letter Amino Acid Symbols) | |
|---|---|---|
| SEQ ID NO: 62<br>heavy chain CDR3<br>for<br>tavolixizumab | RYKYDYDGGH AMDY | 14 |
| SEQ ID NO: 63<br>light chain CDR1<br>for<br>tavolixizumab | QDISNYLN | 8 |
| SEQ ID NO: 64<br>light chain CDR2<br>for<br>tavolixizumab | LLIYYTSKLH S | 11 |
| SEQ ID NO: 65<br>light chain CDR3<br>for<br>tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 14.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to

TABLE 14

Amino acid sequences for OX40 agonist antibodies related to 11D4.

| Identifier | Sequence (One-Letter Amino Acid Symbols) | |
|---|---|---|
| SEQ ID NO: 66 heavy chain for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSSAS<br>TKGPSVFPLA PCSRSTSEST AALGCLVKDY FPEPVTVSWN SGALTSGVHT FPAVLQSSGL<br>YSLSSVVTVP SSNFGTQTYT CNVDHKPSNT KVDKTVERKC CVECPPCPAP PVAGPSVFLF<br>PPKPKDTLMI SRTPEVTCVV VDVSHEDPEV QFNWYVDGVE VHNAKTKPRE EQFNSTFRVV<br>SVLTVVHQDW LNGKEYKCKV SNKGLPAPIE KTISKTKGQP REPQVYTLPP SREEMTKNQV<br>SLTCLVKGFY PSDIAVEWES NGQPENNYKT TPPMLDSDGS FFLYSKLTVD KSRWQQGNVF<br>SCSVMHEALH NHYTQKSLSL SPGK | 60<br>120<br>180<br>240<br>300<br>360<br>420<br>444 |
| SEQ ID NO: 67 light chain for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSS | 60<br>118 |
| SEQ ID NO: 69 light chain variable region for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70 heavy chain CDR1 for 11D4 | SYSMN | 5 |
| SEQ ID NO: 71 heavy chain CDR2 for 11D4 | YISSSSSTID YADSVKG | 17 |
| SEQ ID NO: 72 heavy chain CDR3 for 11D4 | ESGWYLFDY | 9 |
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 15.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region (V$_L$) comprises the sequence shown in SEQ ID NO:79, and conservative amino acid substitutions thereof. In an embodiment, a OX40 agonist comprises V$_H$ and V$_L$ regions that are each at least 99% identical to the sequences shown in SEQ ID NO:78 and SEQ ID NO:79, respectively. In an embodiment, a OX40 agonist comprises V$_H$ and V$_L$ regions that are each at least 98% identical to the sequences shown in SEQ ID NO:78 and SEQ ID NO:79, respectively. In an embodiment, a OX40 agonist comprises V$_H$ and V$_L$ regions that are each at least 97% identical to the sequences shown in SEQ ID NO:78 and SEQ ID NO:79, respectively. In an embodiment, a OX40 agonist comprises V$_H$ and V$_L$ regions that are each at least 96% identical to the sequences shown in SEQ ID NO:78 and SEQ ID NO:79, respectively. In an embodiment, a OX40 agonist comprises V$_H$ and V$_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 15

Amino acid sequences for OX40 agonist antibodies related to 18D8.

| Identifier | Sequence (One-Letter Amino Acid Symbols) | |
|---|---|---|
| SEQ ID NO: 76 heavy chain for 18D8 | EVQLVESGGG LVQPGRSLRL SCAASGFTFD DYAMHWVRQA PGKGLEWVSG ISWNSGSIGY | 60 |
| | ADSVKGRFTI SRDNAKNSLY LQMNSLRAED TALYYCAKDQ STADYYFYYG MDVWGQGTTV | 120 |
| | TVSSASTKGP SVFPLAPCSR STSESTAALG CLVKDYFPEP VTVSWNSGAL TSGVHTFPAV | 180 |
| | LQSSGLYSLS SVVTVPSSNF GTQTYTCNVD HKPSNTKVDK TVERKCCVEC PPCPAPPVAG | 240 |
| | PSVFLFPPKP KDTLMISRTP EVTCVVVDVS HEDPEVQFNW YVDGVEVHNA KTKPREEQFN | 300 |
| | STFRVVSVLT VVHQDWLNGK EYKCKVSNKG LPAPIEKTIS KTKGQPREPQ VYTLPPSREE | 360 |
| | MTKNQVSLTC LVKGFYPSDI AVEWESNGQP ENNYKTTPPM LDSDGSFFLY SKLTVDKSRW | 420 |
| | QQGNVFSCSV MHEALHNHYT QKSLSLSPGK | 450 |
| SEQ ID NO: 77 light chain for 18D8 | EIVVTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPTFGQG TKVEIKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |
| SEQ ID NO: 78 heavy chain variable region for 18D8 | EVQLVESGGG LVQPGRSLRL SCAASGFTFD DYAMHWVRQA PGKGLEWVSG ISWNSGSIGY | 60 |
| | ADSVKGRFTI SRDNAKNSLY LQMNSLRAED TALYYCAKDQ STADYYFYYG MDVWGQGTTV | 120 |
| | TVSS | 124 |
| SEQ ID NO: 79 light chain variable region for 18D8 | EIVVTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPTFGQG TKVEIK | 106 |
| SEQ ID NO: 80 heavy chain CDR1 for 18D8 | DYAMH | 5 |
| SEQ ID NO: 81 heavy chain CDR2 for 18D8 | GISWNSGSIG YADSVKG | 17 |
| SEQ ID NO: 82 heavy chain CDR3 for 18D8 | DQSTADYYFY YGMDV | 15 |

TABLE 15-continued

Amino acid sequences for OX40 agonist antibodies related to 18D8.

| Identifier | Sequence (One-Letter Amino Acid Symbols) | |
|---|---|---|
| SEQ ID NO: 83<br>light chain CDR1<br>for 18D8 | RASQSVSSYL A | 11 |
| SEQ ID NO: 84<br>light chain CDR2<br>for 18D8 | DASNRAT | 7 |
| SEQ ID NO: 85<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 16.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 16

Amino acid sequences for OX40 agonist antibodies related to Hu119-122.

| Identifier | Sequence (One-Letter Amino Acid Symbols) | |
|---|---|---|
| SEQ ID NO: 86<br>heavy chain<br>variable region<br>for Hu119-122 | EVQLVESGGG LVQPGGSLRL SCAASEYEFP SHDMSWVRQA PKGKLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 87<br>light chain<br>variable region<br>for Hu119-122 | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |

TABLE 16-continued

Amino acid sequences for OX40 agonist antibodies related to Hu119-122.

| Identifier | Sequence (One-Letter Amino Acid Symbols) | |
|---|---|---|
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline PLC. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 17.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 17

Amino acid sequences for OX40 agonist antibodies related to Hu106-222.

| Identifier | Sequence (One-Letter Amino Acid Symbols) | |
|---|---|---|
| SEQ ID NO: 94 heavy chain variable region for Hu106-222 | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 95 light chain variable region for Hu106-222 | DIQMTQSPSS LSASVGDRVT ITCKASQDVS TAVAWYQQKP GKAPKLLIYS ASYLYTGVPS<br>RFSGSGSGTD FTFTISSLQP EDIATYYCQQ HYSTPRTFGQ GTKLEIK | 60<br>107 |
| SEQ ID NO: 96 heavy chain CDR1 for Hu106-222 | DYSMH | 5 |
| SEQ ID NO: 97 heavy chain CDR2 for Hu106-222 | WINTETGEPT YADDFKG | 17 |
| SEQ ID NO: 98 heavy chain CDR3 for Hu106-222 | PYYDYVSYYA MDY | 13 |
| SEQ ID NO: 99 light chain CDR1 for Hu106-222 | KASQDVSTAV A | 11 |
| SEQ ID NO: 100 light chain CDR2 for Hu106-222 | SASYLYT | 7 |
| SEQ ID NO: 101 light chain CDR3 for Hu106-222 | QQHYSTPRT | 9 |

In some embodiments, the OX40 agonist antibody is MEDI6469 (also referred to as 9B12). MEDI6469 is a murine monoclonal antibody. Weinberg, et al., *J Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety for all purposes and in particular for all teachings related to OX40 agonists and their use.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 18, wherein the $V_H$ and $V_L$ domains are connected by a linker.

TABLE 18

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 102 OX40L | MERVQPLEEN VGNAARPRFE RNKLLLVASV IQGLGLLLCF TYICLHFSAL QVSHRYPRIQ SIKVQFTEYK KEKGFILTSQ KEDEIMKVQN NSVIINCDGF YLISLKGYFS QEVNISLHYQ KDEEPLFQLK KVRSVNSLMV ASLTYKDKVY LNVTTDNTSL DDFHVNGGEL ILIHQNPGEF CVL | 60 120 180 183 |
| SEQ ID NO: 103 OX40L soluble domain | SHRYPRIQSI KVQFTEYKKE KGFILTSQKE DEIMKVQNNS VIINCDGFYL ISLKGYFSQE VNISLHYQKD EEPLFQLKKV RSVNSLMVAS LTYKDKVYLN VTTDNTSLDD FHVNGGELIL IHQNPGEFCV L | 60 120 131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI SLHYQKDEEP LFQLKKVRSV NSLMVASLTY KDKVYLNVTT DNTSLDDFHV NGGELILIHQ NPGEFCVL | 60 120 128 |
| SEQ ID NO: 105 variable heavy chain for 008 | EVQLVESGGG LVQPGGSLRL SCAASGFTFS NYTMNWVRQA PGKGLEWVSA ISGSGGSTYY ADSVKGRFTI SRDNSKNTLY LQMNSLRAED TAVYYCAKDR YSQVHYALDY WGQGTLVTVS | 60 120 |
| SEQ ID NO: 106 variable light chain for 008 | DIVMTQSPDS LPVTPGEPAS ISCRSSQSLL HSNGYNYLDW YLQKAGQSPQ LLIYLGSNRA SGVPDRFSGS GSGTDFTLKI SRVEAEDVGV YYCQQYYNHP TTFGQGTK | 60 108 |
| SEQ ID NO: 107 variable heavy chain for 011 | EVQLVESGGG VVQPGRSLRL SCAASGFTFS DYTMNWVRQA PGKGLEWVSS ISGGSTYYAD SRKGRFTISR DNSKNTLYLQ MNNLRAEDTA VYYCARDRYF RQQNAFDYWG QGTLVTVSSA | 60 120 |
| SEQ ID NO: 108 variable light chain for 011 | DIVMTQSPDS LPVTPGEPAS ISCRSSQSLL HSNGYNYLDW YLQKAGQSPQ LLIYLGSNRA SGVPDRFSGS GSGTDFTLKI SRVEAEDVGV YYCQQYYNHP TTFGQGTK | 60 108 |

TABLE 18-continued

Additional polypeptide domains useful as OX40 binding domains in fusion proteins
(e.g., structures I-A and I-B) or as scFv OX40 agonist antibodies.

| Identifier | Sequence (One-Letter Amino Acid Symbols) | |
|---|---|---|
| SEQ ID NO: 109 variable heavy chain for 021 | EVQLVESGGG LVQPRGSLRL SCAASGFTFS SYAMNWVRQA PGKGLEWVAV ISYDGSNKYY ADSVKGRFTI SRDNSKNTLY LQMNSLRAED TAVYYCAKDR YITLPNALDY WGQGTLVTVS | 60 120 |
| SEQ ID NO: 110 variable light chain for 021 | DIQMTQSPVS LPVTPGEPAS ISCRSSQSLL HSNGYNYLDW YLQKPGQSPQ LLIYLGSNRA SGVPDRFSGS GSGTDFTLKI SRVEAEDVGV YYCQQYKSNP PTFGQGTK | 60 108 |
| SEQ ID NO: 111 variable heavy chain for 023 | EVQLVESGGG LVHPGGSLRL SCAGSGFTFS SYAMHWVRQA PGKGLEWVSA IGTGGGTYYA DSVMGRFTIS RDNSKNTLYL QMNSLRAEDT AVYYCARYDN VMGLYWFDYW GQGTLVTVSS | 60 120 |
| SEQ ID NO: 112 variable light chain for 023 | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPPAFGG GTKVEIKR | 60 108 |
| SEQ ID NO: 113 heavy chain variable region | EVQLQQSGPE LVKPGASVKM SCKASGYTFT SYVMHWVKQK PGQGLEWIGY INPYNDGTKY NEKFKGKATL TSDKSSSTAY MELSSLTSED SAVYYCANYY GSSLSMDYWG QGTSVTVSS | 60 119 |
| SEQ ID NO: 114 light chain variable region | DIQMTQTTSS LSASLGDRVT ISCRASQDIS NYLNWYQQKP DGTVKLLIYY TSRLHSGVPS RFSGSGSGTD YSLTISNLEQ EDIATYFCQQ GNTLPWTFGG GTKLEIKR | 60 108 |
| SEQ ID NO: 115 heavy chain variable region | EVQLQQSGPE LVKPGASVKI SCKTSGYTFK DYTMHWVKQS HGKSLEWIGG IYPNNGGSTY NQNFKDKATL TVDKSSSTAY MEFRSLTSED SAVYYCARMG YHGPHLDFDV WGAGTTVTVS P | 60 120 121 |
| SEQ ID NO: 116 light chain variable region | DIVMTQSHKF MSTSLGDRVS ITCKASQDVG AAVAWYQQKP GQSPKLLIYW ASTRHTGVPD RFTGGGSGTD FTLTISNVQS EDLTDYFCQQ YINYPLTFGG GTKLEIKR | 60 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY ADDFKGRFAF SLETSASTAY LQINNLKNED TATYFCANPY YDYVSYYAMD YWGHGTSVTV SS | 60 120 122 |
| SEQ ID NO: 118 heavy chain variable region of humanized antibody | QVQLVQSGSE LKKPGASVKV SCKASGYTFT DYSMHWVRQA PGQGLKWMGW INTETGEPTY ADDFKGRFVF SLDTSVSTAY LQISSLKAED TAVYYCANPY YDYVSYYAMD YWGQGTTVTV SS | 60 120 122 |
| SEQ ID NO: 119 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 121 heavy chain variable region of humanized antibody | EVQLVESGGG LVQPGESLKL SCESNEYEFP SHDMSWVRKT PEKRLELVAA INSDGGSTYY PDTMERRFII SRDNTKKTLY LQMSSLRSED TALYYCARHY DDYYAWFAYW GQGTLVTVSA | 60 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 123 light chain variable region of humanized antibody | DIVLTQSPAS LAVSLGQRAT ISCRASKSVS TSGYSYMHWY QQKPGQPPKL LIYLASNLES GVPARFSGSG SGTDFTLNIH PVEEEDAATY YCQHSRELPL TFGAGTKLEL K | 60 111 |

TABLE 18-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 124 light chain variable region of humanized antibody | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 125 heavy chain variable region | MYLGLNYVFI VFLLNGVQSE VKLEESGGGL VQPGGSMKLS CAASGFTFSD AWMDWVRQSP EKGLEWVAEI RSKANNHATY YAESVNGRFT ISRDDSKSSV YLQMNSLRAE DTGIYYCTWG EVFYFDYWGQ GTTLTVSS | 60 120 138 |
| SEQ ID NO: 126 light chain variable region | MRPSIQFLGL LLFWLHGAQC DIQMTQSPSS LSASLGGKVT ITCKSSQDIN KYIAWYQHKP GKGPRLLIHY TSTLQPGIPS RFSGSGSGRD YSFSISNLEP EDIATYYCLQ YDNLLTFGAG TKLELK | 60 120 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

Optional Cell Viability Analyses

Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

According to the present disclosure, a method for assaying TILs for viability and/or further use in administration to a subject. In some embodiments, the method for assay tumor infiltrating lymphocytes (TILs) comprises:
(i) obtaining a first population of TILs;
(ii) performing a first expansion by culturing the first population of TILs in a cell culture medium comprising IL-2, and optionally OKT-3, to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
(iv) harvesting, washing, and cryopreserving the third population of TILs;

(v) storing the cryopreserved TILs at a cryogenic temperature;
(vi) thawing the third population of TILs to provide a thawed third population of TILs; and
(vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;
(viii) determining based on the ratio in step (vii) whether the thawed population of TILs is suitable for administration to a patient;
(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the TILs are assayed for viability after step (vii).

The present disclosure also provides further methods for assaying TILs. In some embodiments, the disclosure provides a method for assaying TILs comprising:
(i) obtaining a portion of a first population of cryopreserved TILs;
(ii) thawing the portion of the first population of cryopreserved TILs;
(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
(iv) determining based on the ratio in step (iii) whether the first population of TILs is suitable for use in therapeutic administration to a patient;
(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

2. Cell Cultures

In an embodiment, a method for expanding TILs, including those discussed above as well as exemplified in FIG. 18, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A 1, the disclosures of which are incorporated herein by reference. Such processes are also described in Jin et al., *J. Immunotherapy*, 2012, 35:283-292.

Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

Optional Cryopreservation of TILs

As discussed above, and exemplified in Steps A through E as provided in FIG. 18, cryopreservation can occur at numerous points throughout the TIL expansion process. In some embodiments, the expanded population of TILs after the second expansion (as provided for example, according to Step D of FIG. 18) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example 10.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

Sterile connecting devices (STCDs) produce sterile welds between two pieces of compatible tubing. This procedure permits sterile connection of a variety of containers and tube diameters. In some embodiments, the closed systems include luer lock and heat sealed systems. In some embodiments, the closed system is accessed via syringes under sterile conditions in order to maintain the sterility and closed nature of the system. In some embodiments, a closed system as described in the Examples is employed. In some embodiments, the TILs are formulated into a final product formulation container according to the method described in the Examples.

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

Optional Cryopreservation of TILs

Either the bulk TIL population or the expanded population of TILs can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 18. In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at $-80°$ C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at $-80°$ C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times.

In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILS are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$, to $5\times10^9$, $5\times10^9$, to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

CERTAIN EXEMPLARY EMBODIMENTS

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein the cancer is double-refractory metastatic melanoma.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein the cancer is double-refractory metastatic melanoma, wherein the double-refractory metastatic melanoma is a cutaneous double-refractory metastatic melanoma.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein the cancer is double-refractory metastatic melanoma, wherein the double-refractory metastatic melanoma is refractory to at least two prior systemic treatment courses, not including neo-adjuvant or adjuvant therapies.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the double-refractory metastatic melanoma is refractory to aldesleukin or a biosimilar thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the double-refractory metastatic melanoma is refractory to pembrolizumab or a biosimilar thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the double-refractory metastatic melanoma is refractory to nivolumab or a biosimilar thereof
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the In an embodiment, the invention provides a method of treating a cancer with a population of tumor infiltrating lymphocytes (TILs) comprising the steps of:
first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the double-refractory metastatic melanoma is refractory to ipilimumab or a biosimilar thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and
(g) administering a therapeutically effective portion of the third population of TILs to a patient with the cancer;

wherein the cancer is double-refractory metastatic melanoma, wherein the double-refractory metastatic melanoma is refractory to ipilimumab or a biosimilar thereof and pembrolizumab or a biosimilar thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;

wherein the cancer is double-refractory metastatic melanoma, wherein the double-refractory metastatic melanoma is refractory to ipilimumab or a biosimilar thereof and nivolumab or a biosimilar thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;

wherein the cancer is double-refractory metastatic melanoma, wherein the initial expansion is performed over a period of 21 days or less.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;

wherein the cancer is double-refractory metastatic melanoma, wherein the initial expansion is performed over a period of 11 days or less.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;

wherein the cancer is double-refractory metastatic melanoma, wherein the IL-2 is present at an initial concentration of between 1000 IU/mL and 6000 IU/mL in the first cell culture medium.

In an embodiment, the invention provides a method of treating a cancer with a population of tumor infiltrating lymphocytes (TILs) comprising the steps of:

(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the IL-2 is present at an initial concentration of between 1000 IU/mL and 6000 IU/mL and the OKT-3 antibody is present at an initial concentration of about 30 ng/mL in the second cell culture medium.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the initial expansion is performed using a gas permeable container.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the rapid expansion is performed using a gas permeable container.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein the cancer is double-refractory metastatic melanoma, wherein the first cell culture medium further comprises a cytokine selected from the group consisting of IL-4, IL-7, IL-15, IL-21, and combinations thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
wherein the cancer is double-refractory metastatic melanoma, wherein the second cell culture medium further comprises a cytokine selected from the group consisting of IL-4, IL-7, IL-15, IL-21, and combinations thereof.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
wherein the cancer is double-refractory metastatic melanoma, further comprising the step of treating the patient with a non-myeloablative lymphodepletion regimen prior to administering the third population of TILs to the patient.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
wherein the cancer is double-refractory metastatic melanoma, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
wherein the cancer is double-refractory metastatic melanoma, further comprising the step of treating the patient with an IL-2 regimen starting on the day after administration of the third population of TILs to the patient.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein the cancer is double-refractory metastatic melanoma, wherein the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Processes for the Manufacture of TILs Suitable for Therapy

Figure 2:
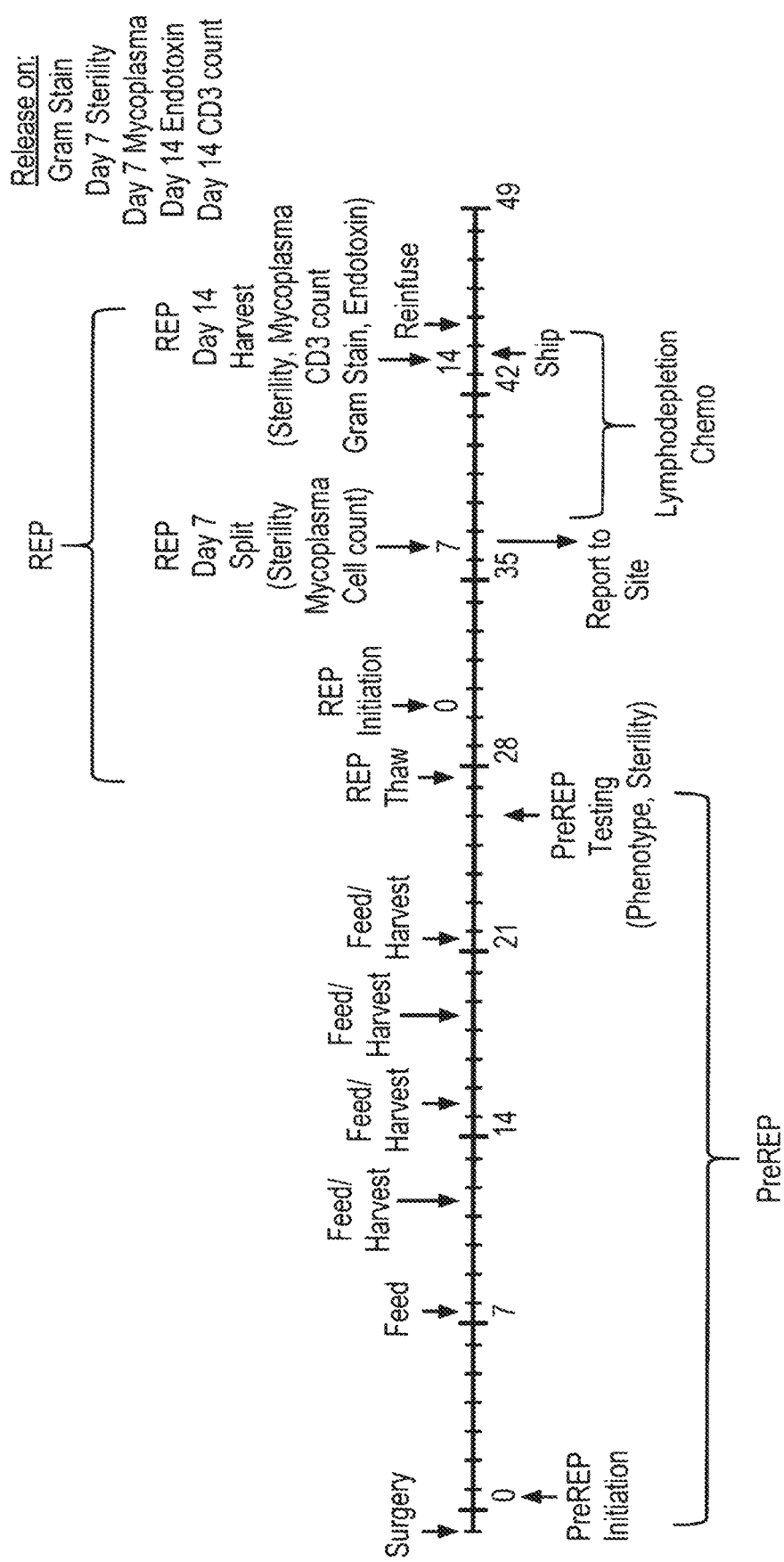
FIG. 2 illustrates a treatment and manufacturing timeline for use with TILs prepared according to the present disclosure and the process of FIG. 1. Surgery (and tumor resection) occurs at the start, and lymphodepletion chemo refers to non-myeloablative lymphodepletion with chemotherapy as described elsewhere herein.

TILs may be manufactured using methods known in the art and any method described herein. For example, an exemplary method for expanding TILs is depicted in FIG. 1. An exemplary timeline for manufacturing TILs and treating a cancer patient with expanded TILs according to the process of FIG. 1 is shown in FIG. 2. Surgery (and tumor resection) occurs at the start, and lymphodepletion chemo refers to non-myeloablative lymphodepletion with chemotherapy as described elsewhere herein.

Figure 3:
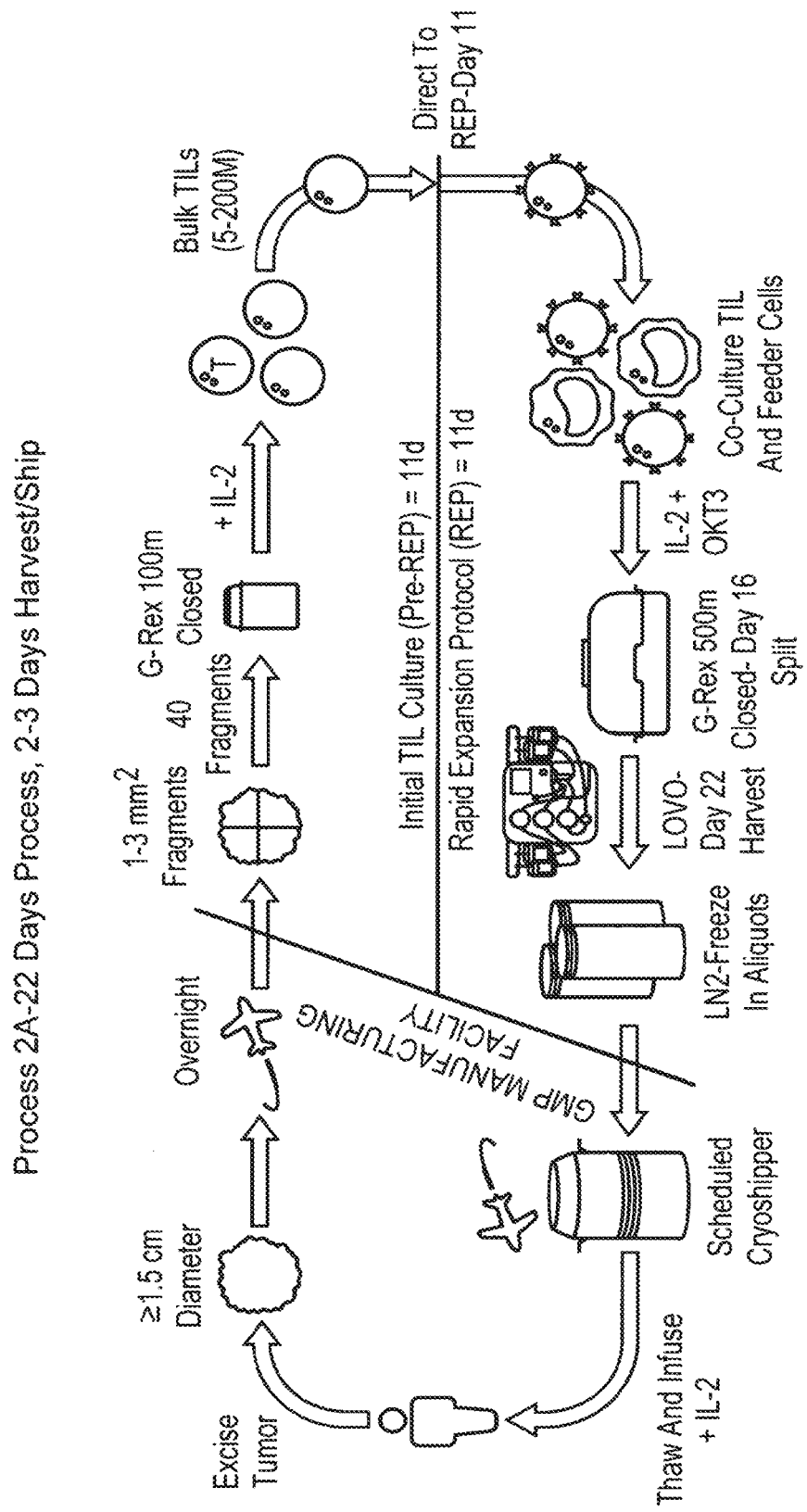
FIG. 3 illustrates a TIL expansion and therapeutic treatment process, including a "direct to REP" step wherein pre-REP TILs are placed directly into a REP process. The total process time is approximately 22 days, at which point TILs may be infused into a patient.
Figure 4:
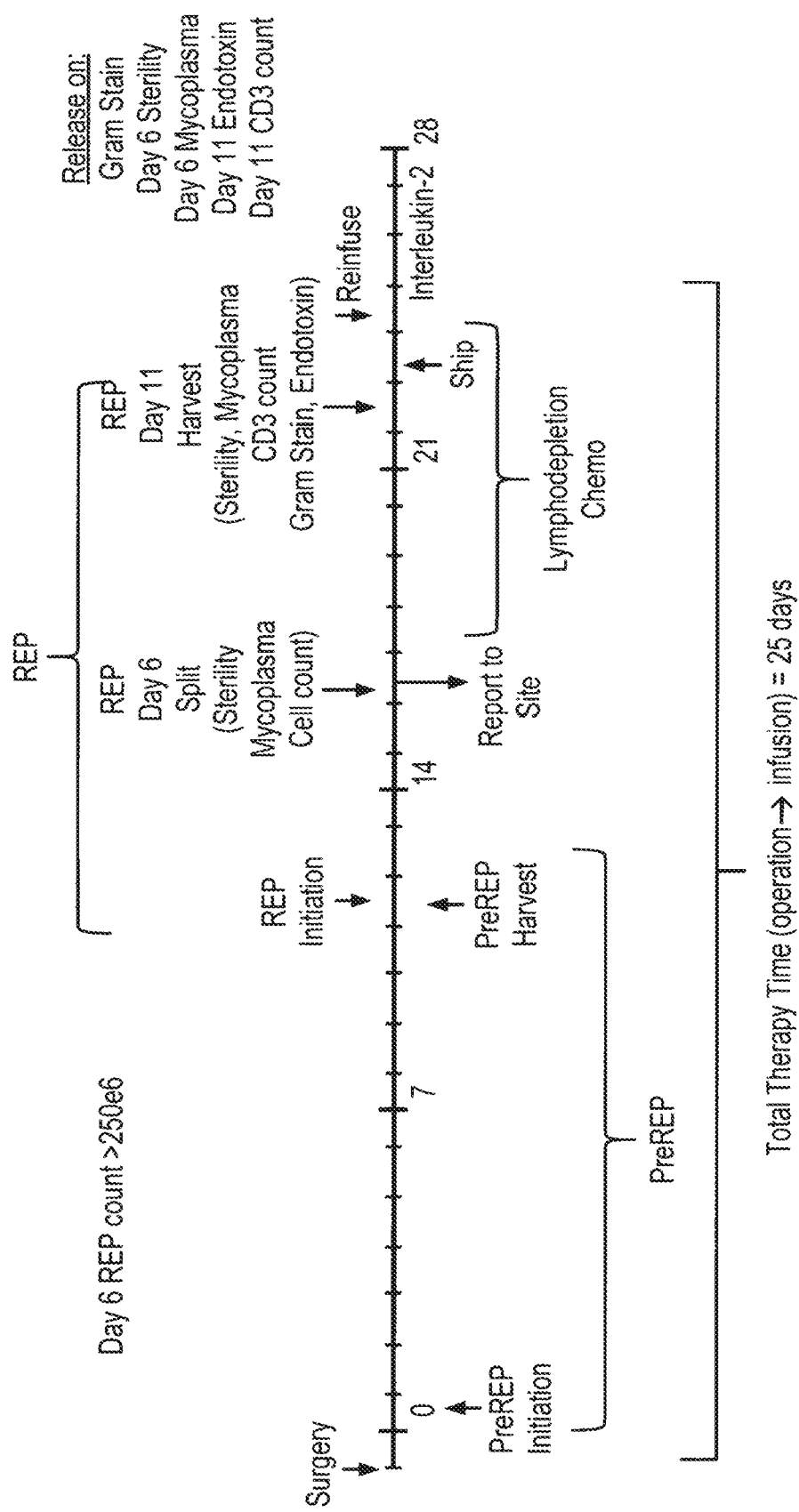
FIG. 4 illustrates a treatment and manufacturing timeline for use with TILs prepared according to the present disclosure and the process of FIG. 3, when the cell count at day 6 is greater than $250 \times 10^6$.
Figure 5:
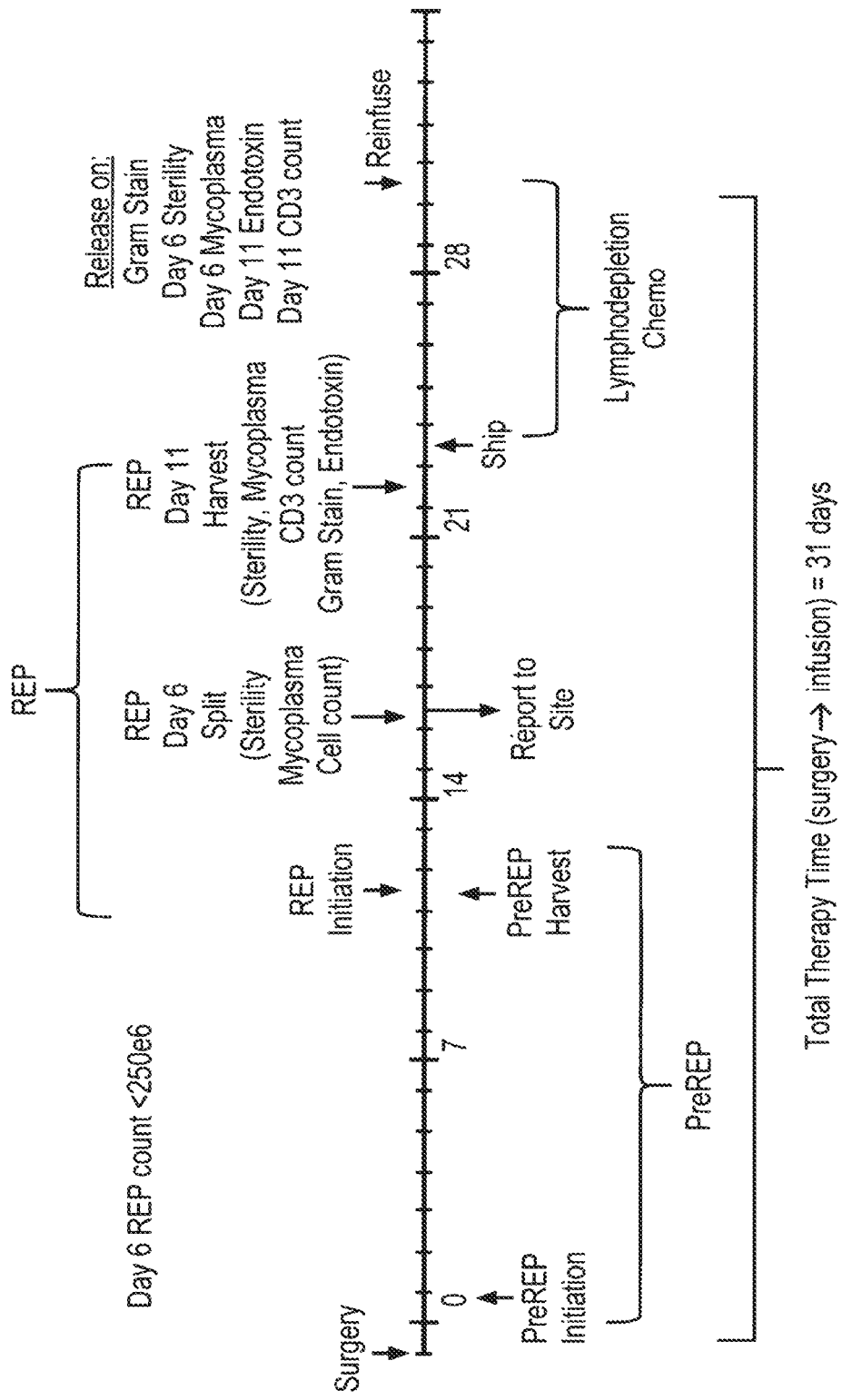
FIG. 5 illustrates a treatment and manufacturing timeline for use with TILs prepared according to the present disclosure and the process of FIG. 3, when the cell count at day 6 is less than $250 \times 10^6$, and wherein lymphodepletion is begun later so as to allow for an assessment of the viability of the TIL product before lymphodepleting the patient.
Figure 6:
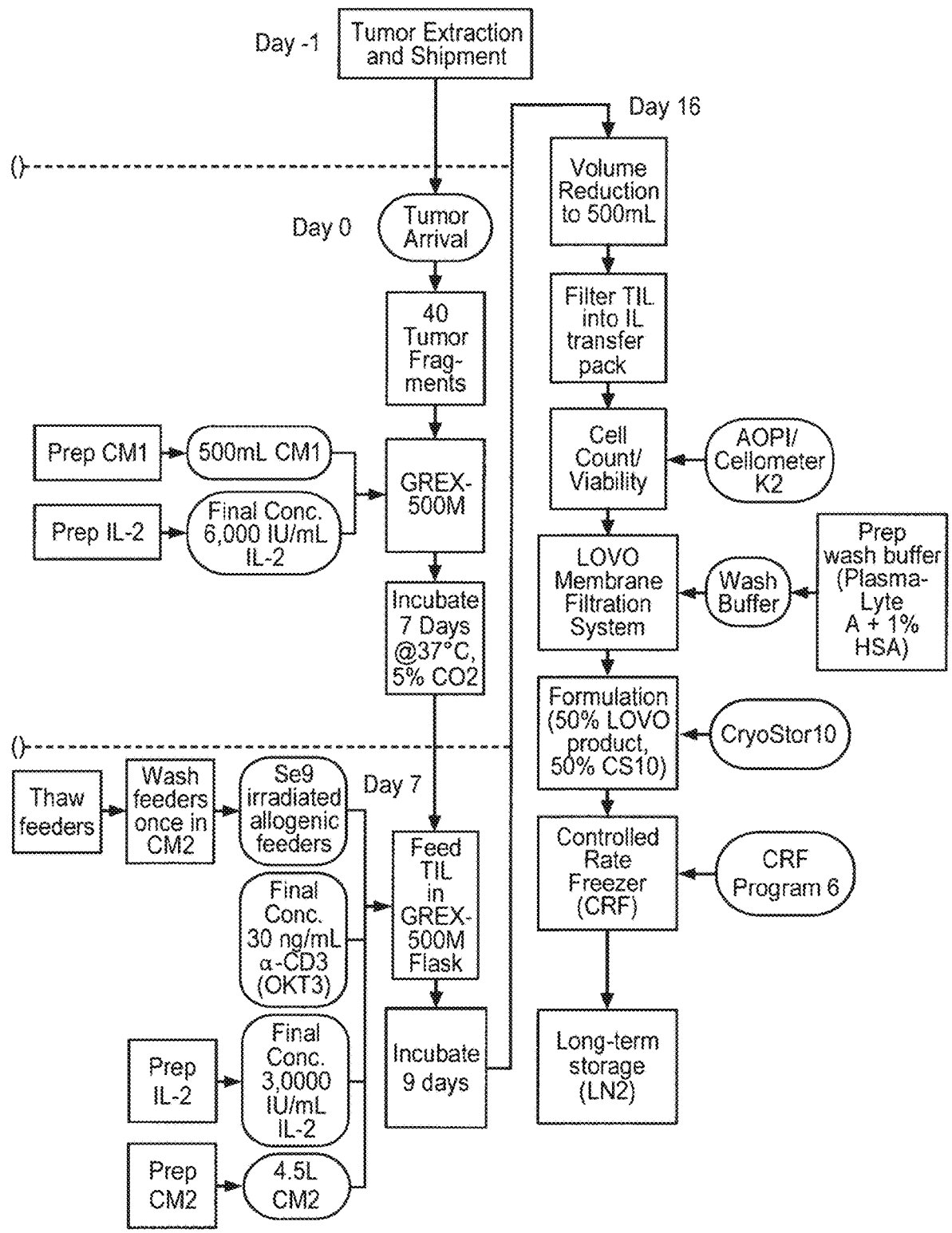
FIG. 6 shows a detailed schematic of a TIL manufacturing process according to FIG. 3.

FIG. 3 illustrates a TIL expansion and therapeutic treatment process, including a "direct to REP" step wherein pre-REP TILs are placed directly into a REP process. The total process time is approximately 22 days, at which point TILs may be infused into a patient. FIG. 4 illustrates a treatment and manufacturing timeline for use with TILs prepared according to the present disclosure and the process of FIG. 3, when the cell count at day 6 is greater than 250×10$^6$. In this situation, the TIL product is considered to be very likely to succeed, and the risk of lymphodepleting the patient in anticipation of obtaining suitable final TIL product is warranted. FIG. 5 illustrates a treatment and manufacturing timeline for use with TILs prepared according to the present disclosure and the process of FIG. 3, when the cell count at day 6 is less than 250×10$^6$, and wherein lymphodepletion is begun later so as to allow for an assessment of the viability of the TIL product before the decision is made to lymphodeplete the patient. FIG. 6 shows a detailed schematic of a TIL manufacturing process according to FIG. 3.

Example 2: Clinical Study 1 of TIL Therapy in Double-Refractory Melanoma

Figure 7:
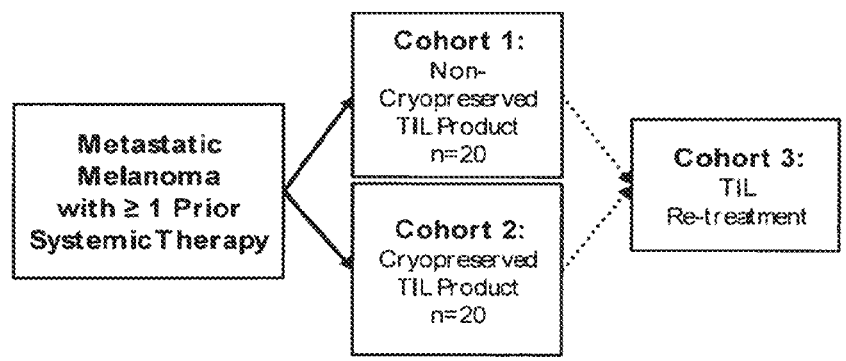
FIG. 7 depicts the design of a clinical study using TIL therapies prepared by different methods in double-refractory melanoma.

This Phase 2, multicenter, three-cohort study is designed to assess the safety and efficacy of a TIL therapy manufactured according to FIG. 1 for treatment of patients with metastatic melanoma. Cohorts one and two will enroll up to 30 patients each and cohort three is a re-treatment cohort for a second TIL infusion in up to ten patients. The first two cohorts are evaluating two different manufacturing processes for (FIG. 1 and FIG. 3, respectively). Patients in cohort one receive fresh, non-cryopreserved TIL (FIG. 1) and cohort two patients receive product manufactured through a more streamlined and rapid three-week procedure (FIG. 3) yielding a cryopreserved product. The study design is shown in FIG. 7. The study is a Phase 2, multicenter, three cohort study to assess the safety and efficacy of autologous TILs for treatment of subpopulations of patients with metastatic melanoma. Key inclusion criteria include: measurable metastatic melanoma and ≥1 lesion resectable for TIL generation; at least one prior line of systemic therapy; age ≥18; and ECOG performance status of 0-1. Treatment cohorts include non-cryopreserved TIL product (prepared using the process of FIG. 1), cryopreserved TIL product (prepared using the process of FIG. 3), and retreatment with TIL product for patients without response or who progress after initial response. The primary endpoint is safety and the secondary endpoint is efficacy, defined as objective response rate (ORR), complete remission rate (CRR), progression free survival (PFS), duration of response (DOR), and overall survival (OS).

Data from 16 patients in cohort one is presented here. These advanced metastatic melanoma patients were a median age of 55 and were highly refractory to multiple prior lines of therapy with significant tumor burden at baseline. All had prior anti-PD-1 therapy, 88% had anti-CTLA4 therapy and 64% had received three or more prior therapies. The results showed that, of the evaluable patients, a 29% objective response rate was reported including one complete response (CR) continuing beyond 15 months post-administration of a single TIL treatment. Furthermore, 77% of patients had reduction in target tumor size. The mean time to first response was 1.6 months, with the CR developing at 6 months. Responses were observed in patients with tumors carrying wild type or BRAF mutations. The protocol allows for administration of up to 6 doses of aldesleukin. The median number of aldesleukin administrations was six.

Patient characteristics are shown in FIG. 8 and FIG. 9. The median number of prior therapies was 3 (range: 1-6). The median sum of diameter for target lesions at baseline was 10.2 cm. 81% of patients had Stage IV disease. The patient population was highly refractory to multiple prior lines of therapy, with significant tumor burden at baseline, and had progressed after at least one checkpoint inhibitor.

Figure 12:
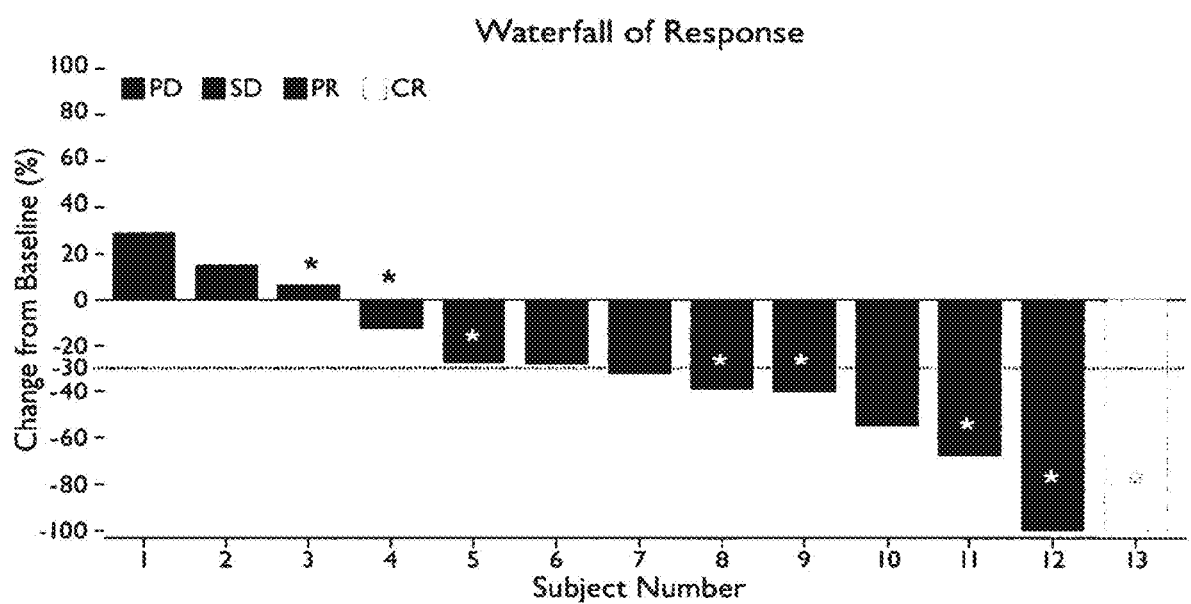
FIG. 12 illustrates a waterfall of response plot showing efficacy in the clinical study. Responses are independent of BRAF mutational status.
Figure 13:
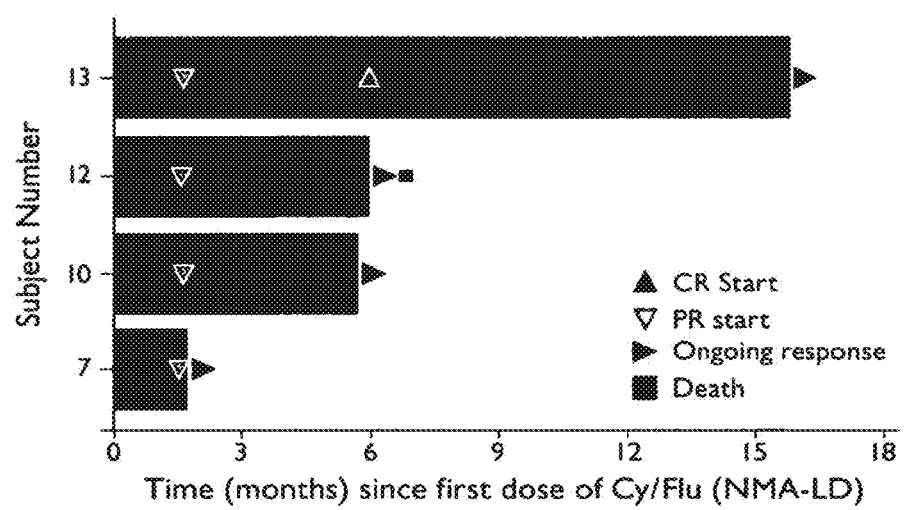
FIG. 13 illustrates time to best response and duration in the clinical study.
Figure 14:
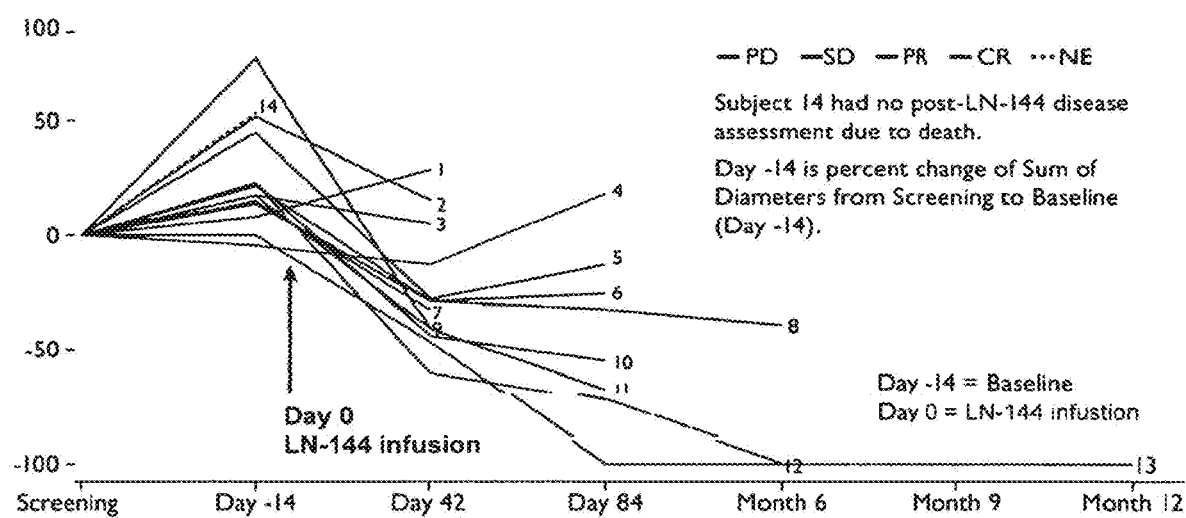
FIG. 14 illustrates percentage change in sum of diameters in the clinical study.
Figure 15:
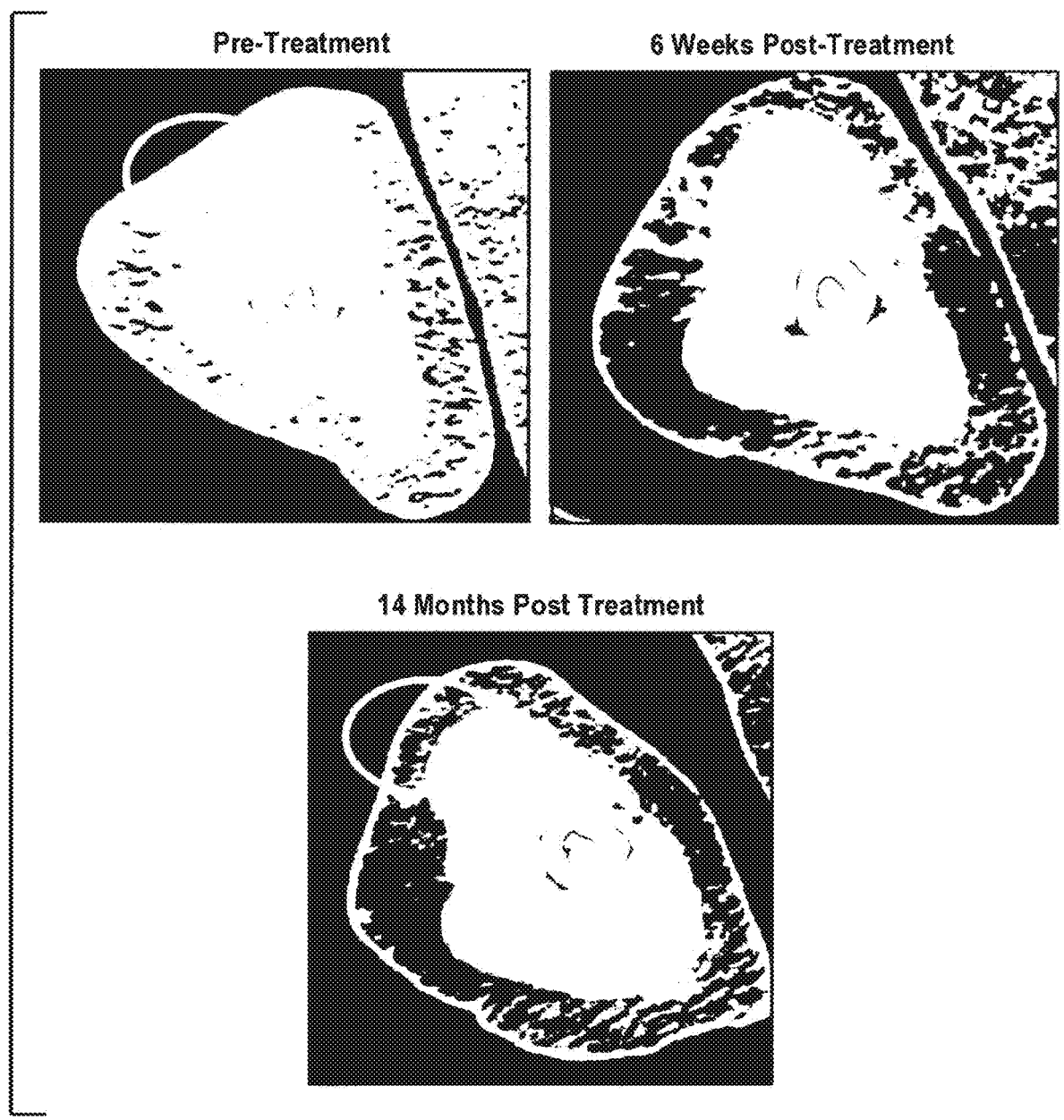
FIG. 15 illustrates scans from a patient in complete remission.

Treatment emergent serious adverse events are summarized in FIG. 10, and efficacy results are summarized in FIG. 11. One of 14 patients was not evaluable due to melanoma-related death prior to first tumor assessment. All patients entering the study had received an anti-PD-1 checkpoint inhibitor. A waterfall of response plot is shown in FIG. 12. The ORR is 29%. Tumor reduction was seen in 77% of patients representing those who had tumor reduction in the target lesions. Responses were noted regardless of BRAF mutational status including one long lasting CR (15+ months). FIG. 13 illustrates time to best response and duration in the clinical study. Mean time to first response was 1.6 months. Median follow up for the data shown in FIG. 13 was 4.1 months. FIG. 14 illustrates percentage change in sum of diameters in the clinical study. FIG. 15 illustrates scans from a patient in complete remission, showing the reduction in tumor size.

Additionally, the protocol for this study was amended to both increase the sample size for the study as well as further define the patient population to patients with unresectable or metastatic melanoma who have progressed after immune checkpoint inhibition therapy (e.g., anti-PD-1), and if BRAF mutation-positive, after BRAF targeted therapy.

Figure 16:
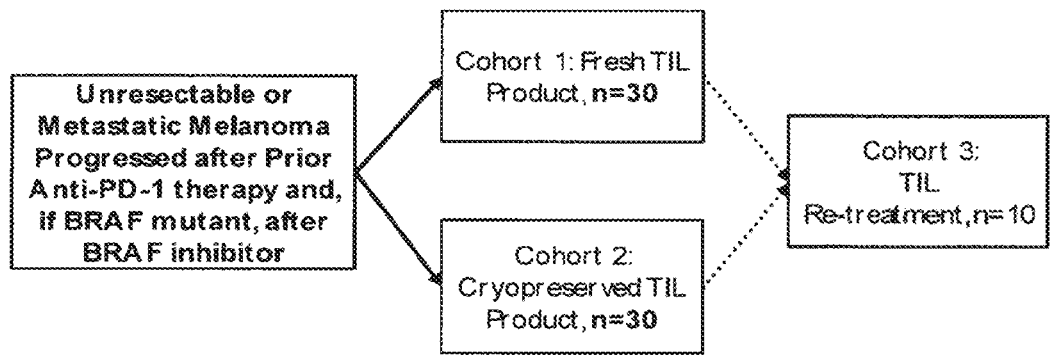
FIG. 16 illustrates the design of a clinical study using TIL therapies.

Based on these results, which illustrate the ability of the TIL therapies of the present disclosure to treat double-refractory metastatic melanoma, the clinical study has been modified as shown in FIG. 16, and furthermore, the primary endpoint has been changed to ORR, with the secondary endpoints changed to CRR, DCR, PFS, DOR, OR, OS, and safety.

Example 3: Clinical Study 2 of TIL Therapy in Double-Refractory Melanoma

Alternative processes for TIL production may also be employed in some embodiments, such as the process described in Radvanyi, et al., *Clin. Cancer Res.* 2012, 18, 6758-70 (including the supporting information), the disclosure of which is incorporated by reference herein. The results from the use of TILs produced by this method in the treatment of patients refractory to both an anti-PD-1 (pembrolizumab or nivolumab) and ipilimumab are shown in FIG. 17.

Example 4: Retrospective Clinical Study

A retrospective study is performed in unresectable, metastatic melanoma patients assessing efficacy data following ≥2 systemic therapies for their disease. This is a retrospective chart review study. The study includes acquisition of retrospective data on disease response in patients who are relapsed/refractory unresectable metastatic melanoma who progressed after receiving ≥2 lines of systemic therapies, where the systemic therapies must include at least one line of PD-1 and BRAF inhibitors for patients with confirmed BRAF mutation positive disease. Selection of patient population is based on prospectively determined inclusion criteria followed by retrospective chart review.

The primary objective of this retrospective study is to evaluate the objective response rate (ORR) assessed by the local evaluation following Response Evaluation Criteria in Solid Tumors (RECIST) 1.1. Secondary objectives of the study include (i) evaluating the efficacy endpoints by the local evaluation for duration of response (DOR), and disease control rate (DCR), assessed by RECIST 1.1; (ii) to evaluate overall survival (OS) based on retrospective data of the study population. An exploratory objective further includes evaluating the treatment pattern of this study population.

Dose and treatment are based on individual institutional data, with the requirement to have been on a treatment in the second or later line of treatment for the unresectable, metastatic melanoma.

Retrospective data will be collected from up to 3 large medical data bases (e.g., from hospitals, academic institutions, oncological cooperative groups) in the United States.

No patients will be actively treated in this retrospective data evaluation study. A minimum of about 100 patients will be assessed for eligibility for the retrospective data review, based on the available institutional data.

Patients will have relapsed/refractory unresectable, metastatic melanoma following ≥2 lines of systemic that must include at least one line of anti-PD-1 and BRAF inhibitors for patients with confirmed BRAF mutation positive disease. Patients will be ≥18 years of age at the time of consent, and will have an Eastern Cooperative Oncology Group (ECOG) performance status of 0 or 1.

Further criteria for inclusion include; patients must have adequate hematopoietic and organ function; patients have provided written authorization for use and disclosure of protected health information, or there is institutional regulation allowing use of clinical data, in compliance with GCP and local ethical standards.

Patients meeting the following criteria will be excluded from the study: patients with melanoma of uveal/ocular origin; patients with symptomatic and/or untreated brain metastases (of any size and any number); patients who have had another primary malignancy within the previous 3 years (with the exception of carcinoma in situ of the breast, cervix, or bladder, localized prostate cancer and nonmelanoma skin cancer that has been adequately treated); patients who have been shown to be BRAF mutation positive (V600), but have not received prior systemic therapy with a BRAF-directed kinase inhibitor.

Efficacy will be assessed based on the application of RECIST 1.1 to the data available in the medical charts of the patients identified according to the inclusion/exclusion criteria. The following parameters will be calculated: ORR, DOR, DCR. Data will be reported by individual institutional data and as aggregate, if feasible.

OS summary will be also assessed pending available individual institutional data. If feasible, aggregate OS data will be reported.

The primary statistical analysis is based on the efficacy parameters obtained from the retrospective data from each institution and it will be performed by individual set of retrospective data per institution.

Statistical comparison among retrospective data sets may or may not be performed.

Patients meeting RECIST 1.1 criteria for a confirmed complete (CR) or partial (PR) response will be classified as responders in the analysis of the ORR.

All time-to-event efficacy endpoints will use the Kaplan-Meier method to summarize the data. The time origin for all such analyses (except for response duration) will be the date on which patients began treatment with the study therapy.

There may or may not be formal comparisons among individual retrospective data sets.

Example 5: Preparation of Media for Pre-REP and REP Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HNSCC), ovarian carcinoma, triple-negative breast carcinoma, and lung adenocarcinoma. This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 19 below by adding each of the ingredients into the top section of a 0.2 μm filter unit appropriate to the volume to be filtered. Store at 4° C.

TABLE 19

| | Preparation of CM1 | | |
|---|---|---|---|
| Ingredient | Final concentration | Final Volume 500 ml | Final Volume 1L |
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 µM | 0.5 ml | 1 ml |
| 50 mg/ml gentamicin sulfate | 50 µg/ml | 0.5 ml | 1 ml |

On the day of use, prewarmed required amount of CM1 in 37° C. water bath and add 6000 IU/ml IL-2.

Additional supplementation—as needed according to Table 20.

TABLE 20

| | Additional supplementation of CM1, as needed. | | |
|---|---|---|---|
| Supplement | Stock concentration | Dilution | Final concentration |
| GlutaMAXTm | 200 mM | 1:100 | 2 mM |
| Penicillin/streptomycin | 10,000 U/ml penicillin 10,000 µg/ml streptomycin | 1:100 | 100 U/ml penicillin 100 µg/ml streptomycin |
| Amphotericin B | 250 µg/ml | 1:100 | 2.5 µg/ml |

Preparation of CM2

Removed prepared CM1 from refrigerator or prepare fresh CM1 as per Section 7.3 above. Removed AIM-V® from refrigerator and prepared the amount of CM2 needed by mixing prepared CM1 with an equal volume of AIM-V® in a sterile media bottle. Added 3000 IU/ml IL-2 to CM2 medium on the day of usage. Made sufficient amount of CM2 with 3000 IU/ml IL-2 on the day of usage. Labeled the CM2 media bottle with its name, the initials of the preparer, the date it was filtered/prepared, the two-week expiration date and store at 4° C. until needed for tissue culture.

Preparation of CM3

Prepared CM3 on the day it was required for use. CM3 was the same as AIM-V® medium, supplemented with 3000 IU/ml IL-2 on the day of use. Prepared an amount of CM3 sufficient to experimental needs by adding IL-2 stock solution directly to the bottle or bag of AIM-V. Mixed well by gentle shaking. Label bottle with "3000 IU/ml IL-2" immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1 L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with "3000 IU/nil IL-2 and GlutaMAX" immediately after adding to the AIM-V. If there was excess CM4, stored it in bottles at 4° C. labeled with the media name, "GlutaMAX", and its expiration date (7 days after preparation). Discarded media supplemented with IL-2 after 7-days storage at 4° C.

Example 6: Use of IL-2, IL-15, and IL-21 Cytokine Cocktail

This example describes the use of IL-2, IL-15, and IL-21 cytokines, which serve as additional T cell growth factors, in combination with the TIL process of Examples 1 to 10.

Using the process of Examples 1 to 10, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vβ repertoire. IL-15 and IL-21 are described elsewhere herein and in Gruijl, et al., IL-21 promotes the expansion of CD27+CD28+ tumor infiltrating lymphocytes with high cytotoxic potential and low collateral expansion of regulatory T cells, Santegoets, S. J., J Transl Med., 2013, 11:37 (https://www.ncbi.nlm.nih.gov/pmc/articles/PMC3626797/).

The results showed that enhanced TIL expansion (>20%), in both CD4$^+$ and CD8$^+$ cells in the IL-2, IL-15, and IL-21 treated conditions were observed in multiple histologies relative to the IL-2 only conditions. There was a skewing towards a predominantly CD8$^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 7: Qualifying Individual Lots of Gamma-Irradiated Peripheral Mononuclear Cells This Example describes a novel abbreviated procedure for qualifying individual lots of gamma-irradiated peripheral mononuclear cells (PBMCs, also known as MNC) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL.to verify that the received dose of gamma radiation was sufficient to render them replication incompetent.

BACKGROUND

Gamma-irradiated, growth-arrested MNC feeder cells were required for REP of TIL. Membrane receptors on the feeder MNCs bind to anti-CD3 (clone OKT3) antibody and crosslink to TIL in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable feeder cells as this can result in Graft-Versus-Host Disease (GVHD). Feeder cells are therefore growth-arrested by dosing the cells with gamma-irradiation, resulting in double strand DNA breaks and the loss of cell viability of the MNC cells upon reculture.

Evaluation Criteria and Experimental Set-Up

Feeder lots were evaluated on two criteria: 1) their ability to expand TIL in co-culture >100-fold and 2) their replication incompetency.

Feeder lots were tested in mini-REP format utilizing two primary pre-REP TIL lines grown in upright T25 tissue culture flasks. Feeder lots were tested against two distinct TIL lines, as each TIL line is unique in its ability to proliferate in response to activation in a REP. As a control, a lot of irradiated MNC feeder cells which has historically been shown to meet the criteria above was run alongside the test lots.

To ensure that all lots tested in a single experiment receive equivalent testing, sufficient stocks of the same pre-REP TIL lines were available to test all conditions and all feeder lots.

For each lot of feeder cells tested, there was a total of six T25 flasks: Pre-REP TIL line #1 (2 flasks); Pre-REP TIL line #2 (2 flasks); and Feeder control (2 flasks). Flasks containing TIL lines #1 and #2 evaluated the ability of the feeder lot to expand TIL. The feeder control flasks evaluated the replication incompetence of the feeder lot.

EXPERIMENTAL PROTOCOL

Day -2/3, Thaw of TIL lines

Prepared CM2 medium. Warmed CM2 in 37° C. water bath. Prepared 40 ml of CM2 supplemented with 3000 IU/ml IL-2. Keep warm until use. Placed 20 ml of pre-warmed CM2 without IL-2 into each of two 50 ml conical tubes labeled with names of the TIL lines used. Removed the two designated pre-REP TIL lines from LN2 storage and transferred the vials to the tissue culture room. Thawed vials by placing them inside a sealed zipper storage bag in a 37° C. water bath until a small amount of ice remains.

Using a sterile transfer pipet, immediately transferred the contents of vial into the 20 ml of CM2 in the prepared, labeled 50 ml conical tube. QS to 40 ml using CM2 without IL-2 to wash cells. Centrifuged at 400×CF for 5 minutes. Aspirated the supernatant and resuspend in 5 ml warm CM2 supplemented with 3000 IU/ml IL-2.

Removed small aliquot (20 µl) in duplicate for cell counting using an automated cell counter. Record the counts. While counting, placed the 50 ml conical tube with TIL cells into a humidified 37° C., 5% $CO_2$ incubator, with the cap loosened to allow for gas exchange. Determined cell concentration and diluted TIL to $1 \times 10^6$ cells/ml in CM2 supplemented with IL-2 at 3000 IU/ml.

Cultured in 2 ml/well of a 24-well tissue culture plate in as many wells as needed in a humidified 37° C. incubator until Day 0 of the mini-REP. Cultured the different TIL lines in separate 24-well tissue culture plates to avoid confusion and potential cross-contamination.

Day 0, Initiate Mini-REP

Prepared enough CM2 medium for the number of feeder lots to be tested. (e.g., for testing 4 feeder lots at one time, prepared 800 ml of CM2 medium). Aliquotted a portion of the CM2 prepared above and supplemented it with 3000 IU/ml IL-2 for the culturing of the cells. (e.g., for testing 4 feeder lots at one time, prepare 500 ml of CM2 medium with 3000 IU/ml IL-2).

Working with each TIL line separately to prevent cross-contamination, removed the 24-well plate with TIL culture from the incubator and transferred to the BSC.

Using a sterile transfer pipet or 100-1000 µl Pipettor and tip, removed about 1 ml of medium from each well of TIL to be used and place in an unused well of the 24-well tissue culture plate.

Using a fresh sterile transfer pipet or 100-1000 µl Pipettor and tip, mixed remaining medium with TIL in wells to resuspend the cells and then transferred the cell suspension to a 50 ml conical tube labeled with the TIL name and recorded the volume.

Washed the wells with the reserved media and transferred that volume to the same 50 ml conical tube. Spun the cells at 400×CF to collect the cell pellet. Aspirated off the media supernatant and resuspend the cell pellet in 2-5 ml of CM2 medium containing 3000 IU/ml IL-2, volume to be used based on the number of wells harvested and the size of the pellet—volume should be sufficient to ensure a concentration of $>1.3 \times 10^6$ cells/ml.

Using a serological pipet, mixed the cell suspension thoroughly and recorded the volume. Removed 200 µl for a cell count using an automated cell counter. While counting, placed the 50 ml conical tube with TIL cells into a humidified, 5% $CO_2$, 37° C. incubator, with the cap loosened to allow gas exchange. Recorded the counts.

Removed the 50 ml conical tube containing the TIL cells from the incubator and resuspend them cells at a concentration of $1.3 \times 10^6$ cells/ml in warm CM2 supplemented with 3000 IU/ml IL-2. Returned the 50 ml conical tube to the incubator with a loosened cap.

Repeated steps above for the second TIL line.

Just prior to plating the TIL into the T25 flasks for the experiment, TIL were diluted 1:10 for a final concentration of $1.3 \times 10^5$ cells/ml as per below.

Prepare MACS GMP CD3 Pure (OKT3) Working Solution

Took out stock solution of OKT3 (1 mg/ml) from 4° C. refrigerator and placed in BSC. A final concentration of 30 ng/ml OKT3 was used in the media of the mini-REP.

600 ng of OKT3 were needed for 20 ml in each T25 flask of the experiment; this was the equivalent of 60 µl of a 10 µs/ml solution for each 20 ml, or 360 µl for all 6 flasks tested for each feeder lot.

For each feeder lot tested, made 400 µl of a 1:100 dilution of 1 mg/ml OKT3 for a working concentration of 10 µg/ml (e.g., for testing 4 feeder lots at one time, make 1600 µl of a 1:100 dilution of 1 mg/ml OKT3: 16 µl of 1 mg/ml OKT3+1.584 ml of CM2 medium with 3000 IU/ml IL-2.)

Prepare T25 Flasks

Labeled each flask and filled flask with the CM2 medium prior to preparing the feeder cells. Placed flasks into 37° C. humidified 5% $CO_2$ incubator to keep media warm while waiting to add the remaining components. Once feeder cells were prepared, the components will be added to the CM2 in each flask.

TABLE 21

Solutions

| Component | Volume in co-culture flasks | Volume in control (feeder only) flasks |
|---|---|---|
| CM2 + 3000 IU/ml IL-2 | 18 ml | 19 ml |
| MNC: $1.3 \times 10^7$/ml in CM2 + 3000IU IL-2 (final concentration $1/.3 \times 10^7$/flask) | 1 ml | 1 ml |
| OKT3: 10 µg/ml in CM2 + 3000IU of IL-2 | 60 µl | 60 µl |
| TIL: $1.3 \times 10^5$/ml in CM2 with 3000IU of IL-2 (final concentration $1.3 \times 10^5$/flask) | 1 ml | 0 |

Prepare Feeder Cells

A minimum of $78 \times 10^6$ feeder cells were needed per lot tested for this protocol. Each 1 ml vial frozen by SDBB had $100 \times 10^6$ viable cells upon freezing. Assuming a 50% recovery upon thaw from LN2 storage, it was recommended to thaw at least two 1 ml vials of feeder cells per lot giving an estimated $100 \times 10^6$ viable cells for each REP. Alternately, if supplied in 1.8 ml vials, only one vial provided enough feeder cells.

Before thawing feeder cells, pre-warmed approximately 50 ml of CM2 without IL-2 for each feeder lot to be tested. Removed the designated feeder lot vials from LN2 storage, placed in zipper storage bag, and place on ice. Thawed vials inside closed zipper storage bag by immersing in a 37° C. water bath. Removed vials from zipper bag, spray or wipe with 70% EtOH and transferred vials to BSC.

Using a transfer pipet immediately transferred the contents of feeder vials into 30 ml of warm CM2 in a 50 ml conical tube. Washed vial with a small volume of CM2 to remove any residual cells in the vial. Centrifuged at 400×CF for 5 minutes. Aspirated the supernatant and resuspended in 4 ml warm CM2 plus 3000 IU/ml IL-2. Removed 200 µl for cell counting using the Automated Cell Counter. Recorded the counts.

Resuspended cells at $1.3 \times 10^7$ cells/ml in warm CM2 plus 3000 IU/ml IL-2. Diluted TIL cells from $1.3 \times 10^6$ cells/ml to $1.3 \times 10^5$ cells/ml.

Setup Co-Culture

Diluted TIL cells from $1.3 \times 10^6$ cells/ml to $1.3 \times 10^5$ cells/ml. Added 4.5 ml of CM2 medium to a 15 ml conical tube. Removed TIL cells from incubator and resuspended well using a 10 ml serological pipet. Removed 0.5 ml of cells from the $1.3 \times 10^6$ cells/ml TIL suspension and added to the 4.5 ml of medium in the 15 ml conical tube. Returned TIL stock vial to incubator. Mixed well. Repeated for the second TIL line.

Transferred flasks with pre-warmed media for a single feeder lot from the incubator to the BSC. Mixed feeder cells by pipetting up and down several times with a 1 ml pipet tip and transferred 1 ml ($1.3 \times 10^7$ cells) to each flask for that feeder lot. Added 60 µl of OKT3 working stock (10 µg/ml) to each flask. Returned the two control flasks to the incubator.

Transferred 1 ml ($1.3 \times 10^5$) of each TIL lot to the correspondingly labeled T25 flask. Returned flasks to the incubator and incubate upright. Did not disturb until Day 5.

Repeated for all feeder lots tested.

Day 5, Media Change

Prepared CM2 with 3000 IU/ml IL-2. 10 ml is needed for each flask. With a 10 ml pipette, transferred 10 ml warm CM2 with 3000 IU/ml IL-2 to each flask. Returned flasks to the incubator and incubated upright until Day 7. Repeated for all feeder lots tested.

Day 7, Harvest

Removed flasks from the incubator and transfer to the BSC, care as taken not to disturb the cell layer on the bottom of the flask. Without disturbing the cells growing on the bottom of the flasks, removed 10 ml of medium from each test flask and 15 ml of medium from each of the control flasks.

Using a 10 ml serological pipet, resuspended the cells in the remaining medium and mix well to break up any clumps of cells. After thoroughly mixing cell suspension by pipetting, removed 200 µl for cell counting. Counted the TIL using the appropriate standard operating procedure in conjunction with the automatic cell counter equipment. Recorded counts in Day 7.

Repeated for all feeder lots tested.

Feeder control flasks were evaluated for replication incompetence and flasks containing TIL were evaluated for fold expansion from Day 0 according to Table 22 below.

Day 7, Continuation of Feeder Control Flasks to Day 14

After completing the Day 7 counts of the feeder control flasks, added 15 ml of fresh CM2 medium containing 3000 IU/ml IL-2 to each of the control flasks. Returned the control flasks to the incubator and incubated in an upright position until Day 14.

Day 14, Extended Non-Proliferation of Feeder Control Flasks

Removed flasks from the incubator and transfer to the BSC, care was taken not to disturb the cell layer on the bottom of the flask. Without disturbing the cells growing on the bottom of the flasks, removed approximately 17 ml of medium from each control flasks. Using a 5 ml serological pipet, resuspended the cells in the remaining medium and mixed well to break up any clumps of cells. Recorded the volumes for each flask.

After thoroughly mixing cell suspension by pipetting, removed 200 µl for cell counting. Counted the TIL using the appropriate standard operating procedure in conjunction with the automatic cell counter equipment. Recorded counts.

Repeated for all feeder lots tested.

Results and Acceptance Criteria

Results

The dose of gamma irradiation was sufficient to render the feeder cells replication incompetent. All lots were expected to meet the evaluation criteria and also demonstrated a reduction in the total viable number of feeder cells remaining on Day 7 of the REP culture compared to Day 0.

All feeder lots were expected to meet the evaluation criteria of 100-fold expansion of TIL growth by Day 7 of the REP culture.

Day 14 counts of Feeder Control flasks were expected to continue the non-proliferative trend seen on Day 7.

Acceptance Criteria

The following acceptance criteria were met for each replicate TIL line tested for each lot of feeder cells Acceptance was two-fold, as follows (outlined in Table 22 below).

TABLE 22

| Acceptance Criteria | |
| --- | --- |
| Test | Acceptance criteria |
| Irradiation of MNC/Replication Incompetence | No growth observed at 7 and 14 days |
| TIL expansion | At least a 100-fold expansion of each TIL (minimum of $1.3 \times 10^7$ viable cells) |

Evaluated whether the dose of radiation was sufficient to render the MNC feeder cells replication incompetent when cultured in the presence of 30 ng/ml OKT3 antibody and 3000 IU/ml IL-2. Replication incompetence was evaluated by total viable cell count (TVC) as determined by automated cell counting on Day 7 and Day 14 of the REP.

Acceptance criteria was "No Growth," meaning the total viable cell number has not increased on Day 7 and Day 14 from the initial viable cell number put into culture on Day 0 of the REP.

Evaluated the ability of the feeder cells to support TIL expansion. TIL growth was measured in terms of fold expansion of viable cells from the onset of culture on Day 0 of the REP to Day 7 of the REP. On Day 7, TIL cultures achieved a minimum of 100-fold expansion, (i.e., greater than 100 times the number of total viable TIL cells put into culture on REP Day 0), as evaluated by automated cell counting.

Contingency Testing of MNC Feeder Lots that do not Meet Acceptance Criteria

In the event that an MNC feeder lot did not meet the either of the acceptance criteria outlined above, the following steps will be taken to retest the lot to rule out simple experimenter error as its cause.

If there are two or more remaining satellite testing vials of the lot, then the lot was retested. If there were one or no remaining satellite testing vials of the lot, then the lot was failed according to the acceptance criteria listed above.

In order to be qualified, the lot in question and the control lot had to achieve the acceptance criteria above. Upon meeting these criteria, the lot was then released for use.

Example 8: Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it was been shown that, in all cases, irradiated PBMC lots from SDBB (San Diego Blood Bank) expand TIL >100-fold on Day 7 of a REP. This modified qualification protocol was intended to apply to irradiated donor PBMC lots from SDBB which were then further tested to verify that the received dose of gamma radiation was sufficient to render them replication incompetent. Once demonstrated that they maintained replication incompetence over the course of 14 days, donor PBMC lots were considered "qualified" for usage to produce clinical lots of TIL.

BACKGROUND

Gamma-irradiated, growth-arrested PBMC were required for current standard REP of TIL. Membrane receptors on the PBMCs bind to anti-CD3 (clone OKT3) antibody and crosslink to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable PBMCs as this could result in Graft-Versus-Host Disease (GVHD). Donor PBMCs are therefore growth-arrested by dosing the cells with gamma-irradiation, resulting in double strand DNA breaks and the loss of cell viability of the PBMCs upon reculture.

Evaluation Criteria 7.2.1 Evaluation criterion for irradiated PBMC lots was their replication incompetency.

Experimental Set-up

Feeder lots were tested in mini-REP format as if they were to be co-cultured with TIL, using upright T25 tissue culture flasks. Control lot: One lot of irradiated PBMCs, which had historically been shown to meet the criterion of 7.2.1, was run alongside the experimental lots as a control. For each lot of irradiated donor PBMC tested, duplicate flasks were run.

Experimental Protocol

Day 0

Prepared ~90 ml of CM2 medium for each lot of donor PBMC to be tested. Kept CM2 warm in 37° C. water bath. Thawed an aliquot of $6\times10^6$ IU/ml IL-2. Returned the CM2 medium to the BSC, wiping with 70% EtOH prior to placing in hood. For each lot of PBMC tested, removed about 60 ml of CM2 to a separate sterile bottle. Added IL-2 from the thawed $6\times10^6$ IU/ml stock solution to this medium for a final concentration of 3000 IU/ml. Labeled this bottle as "CM2/IL2" (or similar) to distinguish it from the unsupplemented CM2.

Prepare OKT3

Took out the stock solution of anti-CD3 (OKT3) from the 4° C. refrigerator and placed in the BSC. A final concentration of 30 ng/ml OKT3 was used in the media of the mini-REP. Prepared a 10 µg/ml working solution of anti-CD3 (OKT3) from the 1 mg/ml stock solution. Placed in refrigerator until needed.

For each PBMC lot tested, prepare 150 µl of a 1:100 dilution of the anti-CD3 (OKT3) stock. For example, for testing 4 PBMC lots at one time, prepare 600 µl of 10 µg/ml anti-CD3 (OKT3) by adding 6 µl of the 1 mg/ml stock solution to 594 µl of CM2 supplemented with 3000 IU/ml IL-2.

Prepare Flasks 7.4.8 Added 19 ml per flask of CM2/IL-2 to the labeled T25 flasks and placed flasks into 37° C., humidified, 5% $CO_2$ incubator while preparing cells.

Prepare Irradiate PBMC

Retrieved vials of PBMC lots to be tested from LN2 storage. These were placed at −80° C. or kept on dry ice prior to thawing. Placed 30 ml of CM2 (without IL-2 supplement) into 50 ml conical tubes for each lot to be thawed. Labeled each tube with the different lot numbers of the PBMC to be thawed. Capped tubes tightly and place in 37° C. water bath prior to use. As needed, returned 50 ml conical tubes to the BSC, wiping with 70% EtOH prior to placing in the hood.

Removed a vial PBMC from cold storage and place in a floating tube rack in a 37° C. water bath to thaw. Allowed thaw to proceed until a small amount of ice remains in the vial. Using a sterile transfer pipet, immediately transferred the contents of the vial into the 30 ml of CM2 in the 50 ml conical tube. Removed about 1 ml of medium from the tube to rinse the vial; returned rinse to the 50 ml conical tube. Capped tightly and swirl gently to wash cells.

Centrifuged at 400×g for 5 min at room temperature. Aspirated the supernatant and resuspend the cell pellet in 1 ml of warm CM2/IL-2 using a 1000 µl pipet tip. Alternately, prior to adding medium, resuspended cell pellet by dragging capped tube along an empty tube rack. After resuspending the cell pellet, brought volume to 4 ml using CM2/IL-2 medium. Recorded volume.

Removed a small aliquot (e.g., 100 µl) for cell counting using an automated cell counter. Performed counts in duplicate according to the particular automated cell counter SOP. It most likely was necessary to perform a dilution of the PBMC prior to performing the cell counts. A recommended starting dilution was 1:10, but this varied depending on the type of cell counter used. Recorded the counts.

Adjusted concentration of PBMC to $1.3\times10^7$ cells/ml using CM2/IL-2 medium. Mixed well by gentle swirling or by gently aspirating up-and-down using a serological pipet.

Set Up Culture Flasks

Returned two labeled T25 flasks to the BSC from the tissue culture incubator. Returned the 10 µg/ml vial of anti-CD3/OKT3 to the BSC. Added 1 ml of the 1.3×10$^7$ PBMC cell suspension to each flask. Added 60 μl of the 10 μg/ml anti-CD3/OKT3 to each flask. Returned capped flasks to the tissue culture incubators for 14 days of growth without disturbance. Placed anti-CD3/OKT3 vial back into the refrigerator until needed for the next lot. Repeated for each lot of PBMC to be evaluated.

Day 14, Measurement of Non-Proliferation of PBMC

Returned the duplicate T25 flasks to the BSC. For each flask, using a fresh 10 ml serological pipet, removed ~17 ml from each of the flasks, then carefully pulled up the remaining media to measure the volume remaining in the flasks. Recorded volume.

Mixed sample well by pipetting up and down using the same serological pipet.

Removed a 200 μl sample from each flask for counting. Counted cells using an automated cell counter. Repeated steps 7.4.26-7.4.31 for each lot of PBMC being evaluated.

Results and Acceptance Criterion

Results

The dose of gamma irradiation was expected to be sufficient to render the feeder cells replication incompetent. All lots were expected to meet the evaluation criterion, demonstrating a reduction in the total viable number of feeder cells remaining on Day 14 of the REP culture compared to Day 0.

Acceptance Criterion: The following acceptance criterion were met for each irradiated donor PBMC lot tested: "No growth"—meant that the total number of viable cells on Day 14 was less than the initial viable cell number put into culture on Day 0 of the REP.

Contingency Testing of PBMC Lots which do not Meet Acceptance Criterion.

In the event than an irradiated donor PBMC lot did not meet the acceptance criterion above, the following steps were taken to retest the lot to rule out simple experimenter error as the cause of its failure. If there were two or more remaining satellite vials of the lot, then the lot was retested. If there are one or no remaining satellite vials of the lot, then the lot was failed according to the acceptance criterion above.

To be qualified, a PBMC lot going through contingency testing had both the control lot and both replicates of the lot in question achieve the acceptance criterion. Upon meeting this criterion, the lot was then released for use.

Example 9: Preparation of Il-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL 1N acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution (6×10$^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left( \frac{\text{Vial Mass (mg)} \times \text{Biological Activity} \left( \frac{IU}{mg} \right)}{6 \times 10^6 \frac{IU}{mL}} \right) - HAc \text{ vol (mL)} =$$

$$1\% \ HSA \ \text{vol (mL)}$$

$$\left( \frac{1 \text{ mg} \times 25 \times 10^6 \frac{IU}{mg}}{6 \times 10^6 \frac{IU}{mL}} \right) - 2 \text{ mL} = 2.167 \text{ mL } HSA$$

For example, according to CellGenix's rhIL-2 lot 10200121 COA, the specific activity for the 1 mg vial is 25×10$^6$ IU/mg. It recommends reconstituting the rhIL-2 in 2 mL 0.2% HAc.

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquotted vial into smaller volumes and stored in cryovials at −20° C. until ready to use. Avoided freeze/thaw cycles. Expired 6 months after date of preparation. Rh-IL-2 labels included vendor and catalog number, lot number, expiration date, operator initials, concentration and volume of aliquot.

Example 10: Cryopreservation Process

This example describes the cryopreservation process method for TILs prepared with the abbreviated, closed procedure described above in Example 8 using the CryoMed Controlled Rate Freezer, Model 7454 (Thermo Scientific).

The equipment used, in addition to that described in Example 9, is as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 11: Production of a Cryopreserved TIL Cell Therapy Using a Closed System This examples describes the cGMP manufacture of Iovance Biotherapeutics, Inc. TIL Cell Therapy Process in G-Rex Flasks according to current Good Tissue Practices and current Good Manufacturing Practices. This material will be manufactured under US FDA Good Manufacturing Practices Regulations (21 CFR Part 210, 211, 1270, and 1271), and applicable ICH Q7 standards for Phase I through Commercial Material.

The process summary is provided in Table 23 below.

TABLE 23

Process summary

| Estimated Day (post-seed) | Activity | Target Criteria | Anticipated Vessels | Estimated Total Volume (mL) |
|---|---|---|---|---|
| 0 | Tumor Dissection | ≤50 desirable tumor fragments per G-Rex100MCS | G-Rex100MCS 1 flask | ≤1000 |
| 11 | REP Seed | 5 – 200 × 10$^6$ viable cells per G-Rex500MCS | G-Rex500MCS 1 flasks | ≤5000 |
| 16 | REP Split | 1 × 10$^9$ viable cells per G-Rex500MCS | G-Rex500MCS ≤5 flasks | ≤25000 |
| 22 | Harvest | Total available cells | 3-4 CS-750 bags | ≤530 |

Throughout this Example, assume 1.0 mL/L=1.0 g/kg, unless otherwise specified. Once opened, the following expiries apply at 2° C. –8° C.: Human Serum, type AB (HI) Gemini, 1 month; 2-mercaptoethanol, 1 month. Gentamicin Sulfate, 50 mg/ml stock may be kept at room temperature for 1 month. Bags containing 10 L of AIM-V media may be warmed at room temperature once only for up to 24 hours prior to use. During the Day 22 harvest two Gatherex™ may be used to harvest the TIL from the G-Rex500MCS flasks.

Day 0 CMI Media Preparation

Prepared RPMI 1640 Media. In the BSC, using an appropriately sized pipette, removed 100.0 mL from 1000 mL RPMI 1640 Media and placed into an appropriately sized container labeled "Waste".

In the BSC added reagents to RPMI 1640 Media bottle. Added the following reagents to the RPMI 1640 Media bottle as shown in table. Recorded volumes added. Amount Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

Capped RPMI 1640 Media bottle and swirled bottle to ensure reagents were mixed thoroughly. Filtered RPMI 1640 Media from Step 8.1.6 through 1 L 0.22-micron filter unit. Labeled filtered media. Aseptically capped the filtered media and labeled with the following information.

Thawed one 1.1 mL IL-2 aliquot (6×10$^6$ IU/mL) (BR71424) until all ice had melted. Recorded IL-2: Lot # and Expiry. Transferred IL-2 stock solution to media. In the BSC, transferred 1.0 mL of IL-2 stock solution to the CM1 Day 0 Media Bottle prepared in Step 8.1.8. Added CM1 Day 0 Media 1 bottle and IL-2 (6×10$^6$ IU/mL) 1.0 mL. Capped and swirled the bottle to mix media containing IL-2. Relabeled as "Complete CM1 Day 0 Media".

Removed 20.0 mL of media using an appropriately sized pipette and dispensed into a 50 mL conical tube. In BSC, transferred 25.0 mL of "Complete CM1 Day 0 Media" (prepared in Step 8.1.13) to a 50 mL conical tube. Labeled the tube as "Tissue Pieces". Aseptically passed G-Rex100MCS (W3013130) into the BSC. In the BSC, closed all clamps on the G-Rex100MCS, leaving vent filter clamp open. Connected the red line of G-Rex100MCS flask to the larger diameter end of the repeater pump fluid transfer set (W3009497) via luer connection. Staged Baxa pump next to BSC. Removed pump tubing section of repeater pump fluid transfer set from BSC and installed in repeater pump. Within the BSC, removed the syringe from Pumpmatic Liquid-Dispensing System (PLDS) (W3012720) and discarded.

Connected PLDS pipette to the smaller diameter end of repeater pump fluid transfer set via luer connection and placed pipette tip in "Complete CM1 Day 0 Media" for aspiration. Opened all clamps between media and G-Rex100MCS. Pumped Complete CM1 media into G-Rex100MCS flask. Set the pump speed to "High" and "9" and pumped all Complete CM1 Day 0 Media into G-Rex100MCS flask. Once all media was transferred, cleared the line and stopped pump.

Disconnected pump from flask. Ensured all clamps were closed on the flask, except vent filter. Removed the repeater pump fluid transfer set from the red media line, and placed a red cap (W3012845) on the red media line. Removed G-Rex100MCS flask from BSC, heated seal off the red cap from the red line near the terminal luer. Labeled G-Rex100MCS flask with QA provided in-process "Day 0" label. Attached sample "Day 0" label below. Incubator parameters: 37.0±2.0° C.; $CO_2$ Percentage: 5.0±1.5% $CO_2$.

Placed the 50 mL conical tube" in incubator for ≥30 minutes of warming.

Day 0 Tumor Wash Media Preparation

Added Gentamicin to HBSS. In the BSC, added 5.0 mL Gentamicin (W3009832 or W3012735) to 1×500 mL HBSS Media (W3013128) bottle. Recorded volumes. Added per bottle: HBSS (500.0 mL); Gentamicin sulfate, 50 mg/ml (5.0 mL). Mixed reagents thoroughly. Filtered HBSS containing gentamicin prepared in Step 8.2.1 through a 1 L 0.22-micron filter unit (W1218810). Aseptically capped the filtered media and labeled with the following information.

Day 0 Tumor Processing

Obtained tumor specimen and transferred into suite at 2-8° C. immediately for processing and recorded tumor information. Labeled three 50 ml conical tubes: the first as "Forceps," the second as "Scalpel," and the third as "Fresh Tumor Wash Media". Labeled 5×100 mm petri dishes as "Wash 1," "Wash 2," "Wash 3," "Holding," and "Unfavorable." Labeled one 6 well plate as "Favorable Intermediate Fragments."

Using an appropriately sized pipette, transferred 5.0 mL of "Tumor Wash Media" into each well of one 6-well plate for favorable intermediate tumor fragments (30.0 mL total). Using an appropriately sized pipette, transferred 50.0 mL of "Tumor Wash Media" prepared in Step 8.2.4 into each 100 mm petri dish for "Wash 1," "Wash 2," "Wash 3," and "Holding" (200.0 mL total). Using an appropriately sized pipette, transfer 20.0 mL of "Tumor Wash Media" prepared in Step 8.2.4 into each 50 mL conical (60.0 mL total).

Aseptically removed lids from two 6-well plates. The lids were utilized for selected tumor pieces. Aseptically passed the tumor into the BSC. Recorded processing start time.

Tumor Wash 1: Using forceps, removed the tumor from the specimen bottle and transferred to the "Wash 1". Using forceps, gently washed tumor and record time. Transferred 20.0 mL (or available volume) of solution from the tumor specimen bottle into a 50 mL conical per sample plan. Labeled and stored bioburden sample collected at 2-8° C. until submitted for testing.

Tumor Wash 2: Using a new set of forceps, removed the tumor from the "Wash 1" dish and transferred to the "Wash 2" dish. Using forceps, washed tumor specimen by gently agitating for ≥3 minutes and allowed it to sit. Recorded time.

Using a transfer pipette, placed 4 individual drops of Tumor Wash Media from the conical into each of the 6 circles on the upturned lids of the 6-well plates (2 lids). Placed an extra drop on two circles for a total of 50 drops.

Tumor Wash 3: Using forceps, removed the tumor from the "Wash 2" dish and transferred to the "Wash 3" dish. Using forceps, washed tumor specimen by gently agitating and allowed it to sit for ≥3 minutes. Recorded time.

Placed a ruler under 150 mm dish lid. Using forceps, aseptically transferred tumor specimen to the 150 mm dissection dish lid. Arranged all pieces of tumor specimen end to end and recorded the approximate overall length and number of fragments. Assessed the tumor for necrotic/fatty tissue. Assessed whether >30% of entire tumor area observed to be necrotic and/or fatty tissue; if yes, ensure tumor was of appropriate size if so proceeded. Assessed whether <30% of entire tumor area were observed to be necrotic or fatty tissue; if yes, proceeded.

Clean-Up Dissection. If tumor was large and >30% of tissue exterior was observed to be necrotic/fatty, performed "clean up dissection" by removing necrotic/fatty tissue while preserving tumor inner structure using a combination of scalpel and/or forceps. To maintain tumor internal structure, used only vertical cutting pressure. Did not cut in a sawing motion with scalpel.

Using a combination of scalpel and/or forceps, cut the tumor specimen into even, appropriately sized fragments (up to 6 intermediate fragments). To maintain tumor internal structure, use only vertical cutting pressure. Did not cut in a sawing motion with scalpel. Ensured to keep non-dissected intermediate fragments completely submerged in "Tumor Wash Media". Transferred each intermediate fragment to the "holding" dish Manipulated one intermediate fragment at a time, dissected the tumor intermediate fragment in the dissection dish into pieces approximately 3×3×3 mm in size, minimizing the amount of hemorrhagic, necrotic, and/or fatty tissues on each piece. To maintain tumor internal structure, used only vertical cutting pressure. Did not cut in a sawing motion with scalpel.

Selected up to eight (8) tumor pieces without hemorrhagic, necrotic, and/or fatty tissue. Used the ruler for reference. Continued dissection until 8 favorable pieces have been obtained, or the entire intermediate fragment has been dissected. Transferred each selected piece to one of the drops of "Tumor Wash Media".

After selecting up to eight (8) pieces from the intermediate fragment, placed remnants of intermediate fragment into a new single well of "Favorable Intermediate Fragments" 6-well plate.

If desirable tissue remains, selected additional Favorable Tumor Pieces from the "favorable intermediate fragments" 6-well plate to fill the drops for a maximum of 50 pieces. Recorded the total number of dissected pieces created.

Removed the "Tissue Pieces" 50 mL conical tube from the incubator. Ensured conical tube was warmed for ≥30 min. Passed "Tissue Pieces" 50 mL conical into the BSC, ensuring not to compromise the sterility of open processing surfaces.

Using a transfer pipette, scalpel, forceps or combination, transferred the selected 50 best tumor fragments from favorable dish lids to the "Tissue Pieces" 50 mL conical tube. If a tumor piece was dropped during transfer and desirable tissue remains, additional pieces from the favorable tumor intermediate fragment wells were added. Recorded numbers of pieces.

Removed G-Rex100MCS containing media from incubator. Aseptically passed G-Rex100MCS flask into the BSC. When transferring the flask, did not hold from the lid or the bottom of the vessel. Transferred the vessel by handling the sides. In the BSC, lifted G-Rex100MCS flask cap, ensuring that sterility of internal tubing was maintained. Swirled conical tube with tumor pieces to suspend and quickly poured the contents into the G-Rex100MCS flask.

Ensured that the tumor pieces were evenly distributed across the membrane of the flask. Gently tilted the flask back and forth if necessary to evenly distribute the tumor pieces. Recorded number of tumor fragments on bottom membrane of vessel and number of observed to be floating in vessel. NOTE: If the number of fragments seeded were NOT equivalent to number of collected in Step 8.3.36H, contacted Area Management, and document in Section 10.0.

Incubated G-Rex100MCS at the following parameters: Incubated G-Rex flask: Temperature LED Display: 37.0±2.0° C.; CO2 Percentage: 5.0±1.5% CO2. Performed calculations to determine the proper time to remove G-Rex100MCS incubator on Day 11. Calculations: Time of incubation; lower limit=time of incubation+252 hours; upper limit=time of incubation+276 hours.

Day 11—Media Preparation

Monitored Incubator. Incubator parameters: Temperature LED Display: 37.0±2.0° C.; $CO_2$ Percentage: 5.0±1.5% CO2. Warmed 3×1000 mL RPMI 1640 Media (W3013112) bottles and 3×1000 mL AIM-V (W3009501) bottles in an incubator for ≥30 minutes. Recorded time. Media: RPMI 1640 and AIM-V. Placed an additional 1×1000 ml bottle of AIM-V Media (W3009501) at room temperature for further use.

Removed the RPMI 1640 Media when time was reached. Record end incubation time in Step 8.4.4. Ensure media was warmed for ≥30 min. In the BSC, removed 100.0 mL from each of the three pre-warmed 1000 mL RPMI 1640 Media bottles and placed into an appropriately sized container labeled "Waste". In the BSC added the following reagents to each of the three RPMI 1640 Media bottles and recorded volumes added to each bottle. GemCell Human serum, Heat Inactivated Type AB (100.0 mL), GlutaMax (10.0 mL), Gentamicin sulfate, 50 mg/ml (1.0 mL), 2-mercaptoethanol (1.0 mL).

Caped bottles and swirled to ensure reagents were mixed thoroughly. Filtered each bottle of media through a separate 1 L 0.22-micron filter unit. Aseptically capped the filtered media and labeled each bottle with CM1 Day 11 Media. Thawed 3×1.1 mL aliquots of IL-2 ($6 \times 10^6$ IU/mL) (BR71424) until all ice had melted Recorded IL 2 lot # and Expiry.

Removed the three bottles of AIM-V Media from the incubator. Recorded end incubation time. Ensured media had been warmed for ≥30 minutes. Using a micropipette, added 3.0 mL of thawed IL-2 into one 1 L bottle of pre-warmed AIM-V media. Rinse micropipette tip with media after dispensing IL-2. Use a new sterile micropipette tip for each aliquot. Recorded the total volume added. Labeled bottle as "AIM-V Containing IL-2". Aseptically transferred a 10 L Labtainer Bag and a repeater pump transfer set into the BSC. Closed all lines on a 10 L Labtainer bag. Attached the larger diameter tubing end of a repeater pump transfer set to the middle female port of the 10 L Labtainer Bag via luer lock connection.

Staged the Baxa pump next to the BSC. Fed the transfer set tubing through the Baxa pump. Set the Baxa Pump to "High" and "9". Removed syringe from Pumpmatic Liquid-Dispensing System (PLDS) and discarded. Ensured to not compromise the sterility of the PLDS pipette.

Connected PLDS pipette to smaller diameter end of repeater pump fluid transfer set via luer connection and placed pipette tip in AIM-V media containing IL-2 bottle (prepared in Step 8.4.13) for aspiration. Opened all clamps between media bottle and 10 L Labtainer.

Using the PLDS, transfer pre-warmed AIM-V media containing IL-2 prepared in Step 8.4.13, as well as two additional AIM-V bottles into the 10 L Labtainer bag. Added the three bottles of filtered CM1 Day 11 Media from Step 8.4.10. After addition of final bottle, cleared the line to the bag. NOTE: Stopped the pump between addition of each bottle of media. Removed PLDS from the transfer set and placed a red cap on the luer of the line in the BSC. Gently massaged the bag to mix. Labeled the media bag with the following information. Expiration date was 24 hours from the preparation date.

Attached a 60 mL syringe to the available female port of the "Complete CM2 Day 11 Media" bag. Removed 20.0 mL of media and place in a 50 mL conical tube. Placed a red cap on the female port of the "Complete CM2 Day 11 Media" Bag. Labeled and stored Media Retain Sample at 2-8° C. until submitted for testing. Heat sealed off the red cap on the transfer set line, close to red cap. Kept the transfer set on the bag.

In the BSC, added 4.5 mL of AIM-V Media that had been labelled with "For Cell Count Dilutions" and lot number to four 15 mL conical tubes. Labeled the tubes with the lot number and tube number (1-4). Labeled 4 cryovials "Feeder" and vial number (1-4). Transferred any remaining 2-mercaptoethanol, GlutaMax, and human serum from the BSC to 2-8° C.

Outside of the BSC, weld a 1 L Transfer Pack to the transfer set attached to the "Complete CM2 Day 11 Media" bag prepared. Labeled transfer pack as "Feeder Cell CM2 Media" and lot number. Made a mark on the tubing of the 1 L Transfer Pack tubing a few inches away from the bag. Placed the empty Transfer Pack onto the scale so that the tubing was on the scale to the point of the mark. Tared the scale and left the empty Transfer Pack on the scale.

Set the Baxa pump to "Medium" and "4." Pumped 500.0±5.0 mL of "Complete CM2 Day 11" media prepared in Step 8.4.22 into Cell CM2 Media" transfer pack. Measured by weight and recorded the volume of Complete CM2 media added to the Transfer Pack.

Once filled, heated seal the line. Separated CM2 Day 11 media bag with transfer set from feeder cell media transfer pack, kept weld toward 1 L transfer pack. Placed "Complete CM2 Day 11 Media" prepared in incubator until use.

Day 11—TIL Harvest

Incubator parameters: Temperature LED Display: 37.0±2.0° C.; CO2 Percentage: 5.0±1.5% CO2. Performed check to ensure incubation parameters are met before removing G-Rex100MCS from incubator. Lower limits the same as described above.

Recorded Time of Removal from incubator. Carefully removed G-Rex100MCS from incubator and ensured all clamps were closed except large filter line. Recorded processing start time.

Labeled a 300 mL Transfer pack as "TIL Suspension". Sterile welded the TIL Suspension transfer (single line) of a Gravity Blood Filter. Placed the 300 mL Transfer Pack on a scale and record dry weight. Labeled 1 L Transfer Pack as "Supernatant".

Sterile welded the red media removal line from the G-Rex100MCS to the "Supernatant" transfer pack. Sterile welded the clear cell removal line from the G-Rex100MCS to one of the two spike lines on the top of the blood filter connected to the "TIL Suspension" transfer pack. Placed G-Rex100MCS on the left side of the GatheRex and the "Supernatant" and "TIL Suspension" transfer packs to the right side.

Install the red media removal line from the G Rex100MCS to the top clamp (marked with a red line) and tubing guides on the GatheRex. Installed the clear harvest line from the G-Rex100MCS to the bottom clamp (marked with a blue line) and tubing guides on the GatheRex. Attached the gas line from the GatheRex to the sterile filter of the G-Rex100MCS flask. Before removing the supernatant from the G-Rex100MCS flask, ensured all clamps on the cell removal lines were closed. Transferred –900 mL of culture supernatant from the G-Rex100MCS to the 1 L Transfer Pack. Visually inspected G-Rex100MCS flask to ensure flask is level and media has been reduced to the end of the aspirating dip tube.

After removal of the supernatant, closed all clamps to the red line.

Vigorously tapped flask and swirled media to release cells. Performed an inspection of the flask to ensure all cells have detached. NOTE: Contacted area management if cells did not detach. Tilted flask away from collection tubing and allowed tumor pieces to settle along edge. Slowly tipped flask toward collection tubing so pieces remained on the opposite side of the flask. If the cell collection straw is not at the junction of the wall and bottom membrane, rapping the flask while tilted at a 450 angle is usually sufficient to properly position the straw.

Released all clamps leading to the TIL Suspension transfer pack. Using the GatheRex, transferred the cell suspension through the blood filter into the 300 mL transfer pack. Maintained the tilted edge until all cells and media are collected. Inspected membrane for adherent cells. Rinsed the bottom of the G-Rex100MCS. Cover ~¼ of gas exchange membrane with rinse media. Ensured all clamps are closed. Heat sealed (per Process Note 5.12) the TIL suspension transfer pack as close to the weld as possible so that the overall tubing length remains approximately the same. Heat sealed the "Supernatant" transfer pack. Maintained enough line to weld. Recorded weight of TIL Suspension transfer pack and calculated the volume of cell suspension.

Welded a 4" plasma transfer set to "supernatant" transfer pack, retaining the luer connection on the 4" plasma transfer set, and transferred into the BSC. Welded a 4" plasma transfer set to 300 mL "TIL Suspension" transfer pack, retained the luer connection on the 4" plasma transfer set, and transferred into the BSC.

Drew up approximately 20.0 mL of supernatant from the 1 L "Supernatant" transfer pack and dispense into a sterile 50 mL conical tube labeled "Bac-T." Removed a 1.0 mL sample from the 50 mL conical labeled BacT using an appropriately sized syringe and inoculated the anaerobic bottle.

Labeled 4 cryovials with vial number (1-4). Using separate 3 mL syringes, pulled 4×1.0 mL cell count samples from TIL Suspension Transfer Pack using the luer connection, and placed in respective cryovials. Placed a red cap (W3012845) on the line. Placed TIL Transfer Pack in incubator until needed. Perform cell counts and calculations. Perform initial cell counts undiluted. If no dilution needed, "Sample [µL]"=200, "Dilution [µL]"=0.

Record cell counts and TIL numbers. If Total Viable TIL Cells is <5×10$^6$ cells, proceeded to "Day 11 G-Rex Fill and Seed". If Total Viable TIL Cells is >5×10$^6$, proceed to "Calculation for flow cytometry".

Calculation for Flow Cytometry.

If the Total Viable TIL Cell count was ≥4.0×10$^7$, calculated the volume to obtain 1.0×10$^7$ cells for the flow cytometry sample. Total viable cells required for flow cytometry: 1.0×10$^7$ cells. Volume of cells required for flow cytometry: Viable cell concentration divided by 1.0×10$^7$ cells.

If Applicable: Recalculated Total Viable Cells and Volume flow. Calculated the remaining Total Viable Cells and remaining volume after the removal of cytometry sample below.

TIL Cryopreservation of Sample

If Applicable: Calculated Volume for Cryopreservation. Calculated the volume of cells required to obtain 1×10$^7$ cells for cryopreservation.

TABLE 24

| Cryopreservation calculation | | |
|---|---|---|
| Total Viable TIL required for cryopreservation | Viable Cell Concentration | Volume of Cells required for cryopreservation C = A ÷ B |
| A. 1 × 10$^7$ cells | B. cells/mL | C. mL |

If Applicable: Removed sample for Cryopreservation. Removed the calculated volume from the TIL Suspension transfer pack. Placed in appropriately sized conical tube and label as "Cryopreservation Sample 1×10$^7$ cells," dated, and lot number. Placed a red cap (W3012845) on the TIL Suspension transfer pack.

Centrifuged the "Cryopreservation Sample 1×10$^7$ cells" according to the following parameters: Speed: 350×g, Time: 10:00 minutes, Temperature: Ambient, Brake: Full (9); Acceleration: Full (9).

Added CS-10. In BSC, aseptically aspirate supernatant. Gently tap bottom of tube to resuspend cells in remaining fluid. Added CS-10. Slowly added 0.5 mL of CS10. Recorded volume added. Cryopreservation Sample Vials Filled at ~0.5 mL.

Day 11—Feeder Cells

Obtained 3 bags of feeder cells with at least two different lot numbers from LN2 freezer. Kept cells on dry ice until ready to thaw. Recorded feeder cell information. Confirmed that at least two different lots of feeder cells were obtained. Placed the Feeder Cell bags into individual zip top bags, based on Lot number, and thawed 37.0±2.0° C. water bath or cytotherm for ~3-5 minutes or until ice has just disappeared.

Feeder cell harness preparation. Welded 4S-4M60 to a CC2 Cell Connect (W3012820), replacing a single spike of the Cell Connect apparatus with the 4-spike end of the 4S-4M60 manifold. Welded as needed.

Attached media transfer pack Weld the "Feeder Cell CM2 Media" transfer pack to a CC2 luer. The bag will be attached to the side of the harness with the needless injection port. Transferred the assembly containing the Complete CM2 Day 11 Media into the BSC.

Pool thawed feeder cells. Within the BSC, pulled 10 mL of air into a 100 mL syringe. Used this to replace the 60 mL syringe on the CC2. Wiped each port on the feeder cell bags with an alcohol pad prior to removing the cover. Spike the three feeder bags using three of the spikes of the CC2. Maintained constant pressure while turning the spike in one direction. Ensure to not puncture the side of the port. Opened the stopcock so that the line from the feeder cell bags is open and the line to the needless injection port is closed. Drew up the contents of the feeder cell bags into the syringe. All three bags drained at once. Once feeder cell bags had been drained, while maintaining pressure on the syringe, clamped off the line to the feeder cell bags. Did not detach syringe below, the syringe from the harness. Recorded the total volume of feeder cells in the syringe.

Added feeder cells to transfer pack. Turned the stopcock so the line to the feeder cell bag was closed and the line to the media Transfer Pack was open. Ensured the line to media transfer pack is unclamped. Dispensed the feeder cells from the syringe into the "Feeder Cell CM2 Media" transfer pack. Clamped off the line to the transfer pack containing the feeder cells and leave the syringe attached to the harness. Massaged bag to mix the pooled feeder cells in the transfer pack. Labeled bag as "Feeder Cell Suspension".

Calculated the total volume of feeder cell suspension. Removed cell count samples. Using a separate 3 mL syringe for each sample, pulled 4×1.0 mL cell count samples from Feeder Cell Suspension Transfer Pack using the needless injection port. Aliquoted each sample into labeled cryovials.

Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution.

Recorded Cell Count and Sample volumes. If Total Viable Cells are <5×10$^9$, proceed. If Total Viable Cells are ≥5×10$^9$, proceeded as above for higher cells counts. Obtained additional Feeder Cells as needed and added to transfer pack as discussed above. Calculated the volume of Feeder Cell Suspension that was required to obtain 5×10$^9$, viable feeder cells. Calculated the volume of excess feeder cells to remove. Round down to nearest whole number.

Removed excess feeder cells. In a new 100 mL syringe, pulled up 10 mL of air and attached the syringe to the harness. Opened the line to the "Feeder Cell Suspension" transfer pack. Using the syringe drew up the volume of feeder cells calculated in Step 8.6.71C plus an additional 10.0 mL from the Transfer Pack into a 100 mL syringe. Closed the line to the Feeder Cell Suspension transfer pack once the volume of feeder cells is removed. Did not remove final syringe. Once a syringe has been filled, replaced it with a new syringe. Multiple syringes could be used to remove total volume. With each new syringe, pulled in 10 mL of air. Recorded the total volume (including the additional 10 mL) of feeder cells removed.

Added OKT3. In the BSC, using a 1.0 mL syringe and 16 G needle, drew up 0.15 mL of OKT3. Aseptically removed the needle from the syringe and attach the syringe to the needless injection port. Injected the OKT3. Opened the stopcock to the "Feeder Cell Suspension" transfer pack and added 10 mL of feeder cells removed in Step 8.6.73 to flush OKT3 through the line. Turned the syringe upside down and push air through to clear the line to the Feeder Cell Suspension transfer pack. Left the remaining feeder cell suspension in the syringe. Closed all clamps and remove the harness from the BSC. Heat sealed the Feeder Cell Suspension transfer pack, leaving enough tubing to weld.

Day 11 G-Rex Fill and Seed

Set up G-Rex500MCS. Removed a G-Rex500MCS from packaging and inspected the flask for any cracks or kinks in the tubing. Ensured all luer connections and closures were tight. Closed all clamps on the G-Rex500MCS lines except for the vent filter line. Using a marker drew a line at the 4.5 L gradation. Removed the "Complete CM2 Day 11 Media", from the incubator.

Prepared to pump media. Welded the red line of the G-Rex500MCS to the repeater pump transfer set attached to the complete CM2 Day 11 Media. Hung the "Complete CM2 Day 11 Media" bag on an IV pole. Fed the pump tubing through the Baxa pump. Pumped media into G-Rex500MCS. Set the Baxa pump to "High" and "9". Pumped 4.5 L of media to the G-Rex500MCS, filling to the line marked on the flask at the 4.5 L gradation. Heat sealed the red line of the G-Rex500MCS near the weld. Labeled the flask with the "Day 11" label. Welded the Feeder Cell: Suspension transfer pack to the flask. Sterile welded the red line of the G-Rex500MCS to the "Feeder Cell Suspension" transfer pack.

Added Feeder Cells to G-Rex500MCS. Opened all clamps between Feeder Cell Suspension and G-Rex500MCS and added Feeder Cell Suspension to flask by gravity feed. Heat sealed the red line near the weld. Welded the TIL Suspension transfer pack to the flask. Sterile weld the red line of the G-Rex500MCS to the "TIL Suspension" transfer pack.

Added TIL to G-Rex500MCS. Opened all clamps between TIL Suspension and G-Rex500MCS and added TIL Suspension to flask by gravity feed. Heat sealed the red line near the weld to remove the TIL suspension bag.

Incubated G-Rex500MCS. Checked that all clamps on the G-Rex500MCS were closed except the large filter line and place in the incubator. Incubator parameters: Temperature LED Display: 37.0±2.0° C., CO2 Percentage: 5.0±1.5% CO2.

Calculated incubation window. Performed calculations to determine the proper time to remove G-Rex500MCS from incubator on Day 16. Lower limit: Time of incubation+108 hours. Upper limit: Time of incubation+132 hours.

Day 11 Excess TIL Cryopreservation

Froze Excess TIL Vials. Recorded and verified the total number of vials placed into the Control Rate Freezer (CRF). Upon completion of freeze, transfer vials from CRF to the appropriate storage container.

Day 16 Media Preparation

Pre-warmed AIM-V Media. Removed three CTS AIM V 10 L media bags from 2-8° C. at least 12 hours prior to use and place at room temperature protected from light. Labeled each bag. Record warming start time and date. Ensured all bags have been warmed for a duration between 12 and 24 hours.

Attached the larger diameter end of a fluid pump transfer set to one of the female ports of a 10 L Labtainer bag using the Luer connectors. Setup 10 L Labtainer for Supernatant Label as "Supernatant". Setup 10 L Labtainer for Supernatant. Ensure all clamps were closed prior to removing from the BSC.

Thawed 5×1.1 mL aliquots of IL-2 ($6 \times 10^6$ IU/mL) (BR71424) per bag of CTS AIM V media until all ice had melted. Aliquoted 100.0 mL of Glutamax into an appropriately sized receiver. Recorded the volume added to each receiver and labeled each receiver as "GlutaMax."

Added IL-2 to GlutaMax. Using a micropipette, added 5.0 mL of IL-2 to each GlutaMax receiver. Ensured to rinse the tip per process note 5.18 and used a new pipette tip for each mL added. Recorded volume added to each Glutamax receiver and labeled each receiver as "GlutaMax+IL-2" and receiver number.

Prepared CTS AIM V media bag for formulation. Ensured CTS AIM V 10 L media bag (W3012717) was warmed at room temperature and protected from light for 12-24 hours prior to use. Recorded end incubation time. In the BSC, closed clamp on a 4" plasma transfer set, then connected to the bag using the spike ports. Maintained constant pressure while turning the spike in one direction. Ensured to not puncture the side of the port. Connected the larger diameter end of a repeater pump fluid transfer set to the 4" plasma transfer set via luer.

Stage Baxa pump next to BSC. Removed pump tubing section of repeater pump fluid transfer set from BSC and installed in repeater pump.

Prepared to formulate media. In BSC, removed syringe from Pumpmatic Liquid-Dispensing System (PLDS) and discarded. Ensured to not compromise the sterility of the PLDS pipette. Connected PLDS pipette to smaller diameter end of repeater pump fluid transfer set via luer connection and placed pipette tip in "GlutaMax+IL-2" prepared above for aspiration. Open all clamps between receiver and 10 L bag.

Pumped GlutaMax+IL-2 into bag. Set the pump speed to "Medium" and "3" and pump all "GlutaMax+IL-2" into 10 L CTS AIM V media bag. Once no solution remains, clear line and stop pump. Recorded the volume of GlutaMax containing IL-2 added to each Aim V bag below.

Removed PLDS. Ensured all clamps were closed, and removed the PLDS pipette from the repeater pump fluid transfer set. Removed repeater pump fluid transfer set and red cap the 4" plasma transfer set.

Labeled each bag of "Complete CM4 Day 16 media" prepared.

Removed Media Retain per Sample Plan. Using a 30 mL syringe, removed 20.0 mL of "Complete CM4 Day 16 media" by attaching syringe to the 4" plasma transfer set and dispensed sample into a 50 mL conical tube. Ensure 4" plasma transfer set was either clamped or red capped after removal of syringe.

Attached new repeater pump fluid transfer set. Attached the larger diameter end of a new fluid pump transfer set onto the 4" plasma transfer set that was connected to the "Complete CM4 Day 16 media" bag. Labeled with sample plan inventory label and stored media retain sample at 2-8° C. until submitted for testing.

Monitored Incubator. If applicable, monitor for additional bags prepared. Incubator parameters: Temperature LED Display: 37.0±2.0° C., CO2 Percentage: 5.0±1.5% CO2.

Warmed Complete CM4 Day 16 Media. Warmed the first bag of Complete CM4 Day 16 Media in incubator for ≥30 minutes until ready for use. If applicable, warmed additional bags.

Prepared Dilutions. In the BSC, added 4.5 mL of AIM-V Media that had been labelled with "For Cell Count Dilutions" to each 4×15 mL conical tube. Labeled the conical tubes. Labeled 4 cryovials.

Day 16 REP Spilt

Monitored Incubator. Incubator parameters: Temperature LED Display: 37.0±2.0° C., CO2 Percentage: 5.0±1.5% CO2

Removed G-Rex500MCS from Incubator. Performed check below to ensure incubation parameters are met before removing G-Rex500MCS from incubator: upper limit, lower limit, time of removal. Removed G-Rex500MCS from the incubator.

Heat sealed a 1 L transfer pack (W3006645), leaving ~12" of line. Labeled 1 L transfer pack as TIL Suspension. Place 1 L transfer pack, including the entire line, on a scale and record dry weight.

GatheRex Setup. Sterile welded the red media removal line from the G-Rex500MCS to the repeater pump transfer set on the 10 L labtainer bag "Supernatant" prepared above. Sterile welded the clear cell removal line from the G-Rex500MCS to the TIL Suspension transfer pack prepared above. Placed G-Rex500MCS flask on the left side of the GatheRex. Placed the supernatant labtainer bag and TIL suspension transfer pack to the right side. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex. Attached the gas line from the GatheRex to the sterile filter of the G-Rex500 MCS. NOTE: Before removing the supernatant from the G-Rex500MCS, ensured all clamps on the cell removal lines were closed.

Volume Reduction of G-Rex500MCS. Transferred ~4.5 L of culture supernatant from the G-Rex500MCS to the 10 L Labtainer per SOP-01777. Visually inspect G-Rex500MCS to ensure flask as level and media had been reduced to the end of the aspirating dip tube.

Prepared flask for TIL Harvest. After removal of the supernatant, closed all clamps to the red line.

Initiation of TIL Harvest. Recorded the start time of the TIL harvest. Vigorously tap flask and swirl media to release cells. Performed an inspection of the flask to ensure all cells have detached. Tilted the flask to ensure hose is at the edge of the flask. If the cell collection straw is not at the junction of the wall and bottom membrane, rapping the flask while tilted at a 450 angle is usually sufficient to properly position the straw.

TIL Harvest. Released all clamps leading to the TIL suspension transfer pack. Using the GatheRex transferred the cell suspension into the TIL Suspension transfer pack. NOTE: Be sure to maintain the tilted edge until all cells and media are collected. Inspected membrane for adherent cells.

Rinsed flask membrane. Rinsed the bottom of the G-Rex500MCS. Cover ~¼ of gas exchange membrane with rinse media. Closed clamps on G-Rex500MCS. Ensured all clamps were closed on the G-Rex500MCS.

Heat sealed. Heat sealed the Transfer Pack containing the TIL as close to the weld as possible so that the overall tubing length remained approximately the same. Heat sealed the 10 L Labtainer containing the supernatant and passed into the BSC for sample collection.

Recorded weight of Transfer Pack with cell suspension and calculate the volume suspension. Prepared transfer pack for sample removal. Welded a 4" Plasma Transfer Set, to the TIL Suspension transfer pack from above, leaving the female luer end attached as close to the bag as possible.

Removed testing samples from cell supernatant. In the BSC, remove 10.0 mL of supernatant from 10 L labtainer using female luer port and appropriately sized syringe. Placed into a 15 mL conical tube and label as "BacT" and Retain the tube for BacT sample. Using a separate syringe, removed 10.0 mL of supernatant and placed into a 15 mL conical tube. Retained the tube for *Mycoplasma* sample for testing. Labeled tube as "*Mycoplasma* diluent". Closed supernatant bag. Placed a red cap on the luer port to close the bag, and pass out of BSC.

Removed Cell Count Samples. In the BSC, using separate 3 mL syringes for each sample, removed 4×1.0 mL cell count samples from "TIL Suspension" transfer pack using the luer connection. Placed samples in cryovials prepared above.

Removed *Mycoplasma* Samples. Using a 3 mL syringe, removed 1.0 mL from TIL Suspension transfer pack and place into 15 mL conical labeled "*Mycoplasma* diluent" prepared above. Labeled and stored *Mycoplasma* sample at 2-8° C. until submitted for testing.

Prepared Transfer Pack for Seeding. In the BSC, attached the large diameter tubing end of a Repeater Pump Fluid Transfer Set to the Luer adapter on the transfer pack containing the TIL. Clamped the line close to the transfer pack using a hemostat. Placed a red cap onto the end of the transfer set.

Placed TIL in Incubator. Removed cell suspension from the BSC and place in incubator until needed. Recorded time.

Performed Cell Counts. Performed cell counts and calculations utilizing NC-200. Diluted cell count samples initially by adding 0.5 mL of cell suspension into 4.5 mL of AIM-V media prepared above. This gave a 1:10 dilution.

Calculated flasks for subculture. Calculated the total number of flasks to seed. NOTE: Rounded the number of G-Rex500MCS flasks to see up to the neared whole number.

TABLE 25

Flask calculation

| Total Viable Cell Count A | Target Cells Required per Flask B | Number of G-Rex500MCS Flasks to Seed C = A ÷ B |
|---|---|---|
| cells | $1.0 \times 10^9$ cells/flask | flasks |

The maximum number of G-Rex500MCS flasks to seed was five. If the calculated number of flasks to seed exceeded five, only five were seeded USING THE ENTIRE VOLUME OF CELL SUSPENSION AVAILABLE.

Determined number of additional media bags needed. Calculated the number of media bags required in addition to the bag prepared above. Round the number of media bags required up to the next whole number.

TABLE 26

Media bag calculation

| Number of G-Rex500MCS Flasks to Seed A | Number of Media Bag Required B = A ÷ 2* | Number of Bags Prepared in above C | Number of Additional Bags to Prepare D = B − C |
|---|---|---|---|
| | | 1 | |

Prepared additional media as needed. Prepared one 10 L bag of "CM4 Day 16 Media" for every two G-Rex-500M flask needed calculated in Step 8.10.59D. Proceeded to Step 8.10.62 and seeded the first GREX-500M flask(s) while additional media is prepared and warmed.

Prepared additional media bags as needed. Prepared and warmed the calculated number of additional media bags determined above.

Filled G-Rex500MCS. Opened a G-Rex500MCS on the benchtop and inspected for cracks in the vessel or kinks in the tubing. Ensured all luer connections and closures were tight. Made a mark at the 4500 mL line on the outside of the flask with a marker. Closed all clamps on the G-Rex500MCS except the large filter line. Sterile welded the red media line of a G-Rex500MCS to the fluid transfer set on the media bag prepared above.

Prepared to pump media. Hung "CM4 Day 16 Media" on an IV pole. Fed the pump tubing through the Baxa pump.

Pumped media into G-Rex500MCS. Set the Baxa pump on "High" and "9" and pump 4500 mL of media into the flask. Pumped 4.5 L of "CM4 Day 16 Media" into the G-Rex500MCS, filling to the line marked on the flask as above. Once 4.5 L of media had been transferred, stopped the pump.

Heat Sealed. Heat sealed the red media line of G-Rex500MCS, near the weld created, removing the media bag.

Repeated Fill. Repeat filling and sealing steps for each flask calculated in above as media is warmed and prepared for use. Multiple flasks may be filled at the same time using gravity fill or multiple pumps. Fill only two flasks per bag of media.

Recorded and labelled flask(s) filled. Labeled each flask alphabetically and with "Day 16" labels.

As needed incubated flask. Held flask in incubator while waiting to seed with TIL. Recorded the total number of flasks filled.

Calculated volume of cell suspension to add. Calculated the target volume of TIL suspension to add to the new G-Rex500MCS flasks.

TABLE 27

Cell suspension volume

| Total Volume of TIL suspension A | Number of flask (s) filled | Target Volume of cell suspension to transfer to each flask C = A ÷ B |
|---|---|---|
| mL | | mL |

If number of flasks exceeds five only five will be seeded, USING THE ENTIRE VOLUME OF CELL SUSPENSION.

Prepared Flasks for Seeding. Removed G-Rex500MCS from Step 8.10.70 from the incubator.

Prepared for pumping. Closed all clamps on G-Rex500MCS except large filter line. Fed the pump tubing through the Baxa pump.

Removed TIL from incubator. Removed "TIL Suspension" transfer pack from the incubator and record incubation end time.

Prepared cell suspension for seeding. Sterile welded "TIL Suspension" transfer pack from above to pump inlet line.

Placed TIL suspension bag on a scale. Primed the line from the TIL suspension bag to the weld using the Baxa pump set to "Low" and "2". Tared the scale.

Seeded flask with TIL Suspension. Set Baxa pump to "Medium" and "5". Pump the volume of TIL suspension calculated above into flask. Record the volume of TIL Suspension added to each flask.

Heat sealed. Heat sealed the "TIL Suspension" transfer pack, leaving enough tubing to weld on the next flask.

Filled remaining flasks. Between each flask seeded, ensured to mix "TIL Suspension" transfer pack and repeat filling and sealing steps to seed all remaining flaks.

Monitored Incubator. If flasks must be split among two incubators, ensure to monitor both. Incubator parameters: Temperature LED Display: 37.0±2.0° C., $CO_2$ Percentage: 5.0±1.5% $CO_2$. Recorded the time each flask is placed in the incubator.

Calculated incubation window. Performed calculations below to determine the time range to remove G-Rex500MCS from incubator on Day 22. Lower limit: time+132 hours; upper limit: time+156 hours.

Day 22 Wash Buffer Preparation

Prepared 10 L Labtainer Bag. In BSC, attach a 4" plasma transfer set to a 10 L Labtainer Bag via luer connection. Prepared 10 L Labtainer Bag Label as "Supernatant", lot number, and initial/date. Closed all clamps before transferring out of the BSC. NOTE: Prepared one 10 L Labtainer Bag for every two G-Rex500MCS flasks to be harvested.

Welded fluid transfer set. Outside the BSC, closed all clamps on 4S-4M60. Welded repeater fluid transfer set to one of the male luer ends of 4S-4M60.

Passed Plasmalyte-A and Human Albumin 25% into the BSC. Passed the 4S-4M60 and repeater fluid transfer set assembly into the BSC.

TABLE 28

Components

| Component Description | Amount Needed |
|---|---|
| Plasmalyte-A | 3000.0 mL |
| Human Albumin 25% | 120.0 mL |
| 4S-4M60 with Repeater Fluid Transfer Set | 1 Apparatus |
| | Step 8.11.7 |

TABLE 29

| Plasmalyte-A | |
|---|---|
| Latex: | Not Made with Natural Rubber Latex |
| Container Type: | VIAFLEX |
| PVC: | Contains PVC |
| DEHP: | Contains DEHP |
| Volume: | 500 ML |
| Total Calories: | 21 Kcal/L |
| Sodium: | 140 mEq/L |
| Potassium: | 5 mEq/L |
| Magnesium: | 3 mEq/L |
| Acetate: | 27 mEq/L |
| Chloride: | 98 mEq/L |
| Gluconate: | 23 mEq/L |
| Osmolarity (mOsmol/L): | 294 |
| Specific Gravity: | 1.01 |
| pH: | 7.4 |
| Fill Range Volume (mL): | 530-565 |
| Shelf Life from manufacture: | 15 months |
| Contains Preservative: | No |
| Storage Recommendations: | Store at room temperature (25° C./77° F.); brief exposure up to 40° C./104° F. does not adversely affect the product. |
| Packaging: | Single Pack |
| Rx Only: | Yes |

**As commercially available from http://ecatalog.baxter.com/ecatalog/loadproduct.html?cid=20016&lid=10001&hid=20001&pid=821874.

Pumped Plasmalyte into 3000 mL bag. Spiked three bags of Plasmalyte-A to the 4S-4M60 Connector set. NOTE: Wipe the port cover with an alcohol swab (W3009488) prior to removing. NOTE: Maintain constant pressure while turning the spike in one direction. Ensure to not puncture the side of the port. Connected an Origen 3000 mL collection bag via luer connection to the larger diameter end of the repeater pump transfer set. Closed clamps on the unused lines of the 3000 mL Origen Bag. Staged the Baxa pump next to the BSC. Fed the transfer set tubing through the Baxa pump situated outside of the BSC. Set pump to "High" and "9". Opened all clamps from the Plasmalyte-A to the 3000 mL Origen Bag. Pumped all of the Plasmalyte-A into the 3000 mL Origen bag. Once all the Plasmalyte-A had been transferred, stopped the pump. If necessary, removed air from 3000 mL Origen bag by reversing the pump and manipulating the position of the bag. Closed all clamps.

Remove the 3000 mL bag from the repeater pump fluid transfer set via luer connection and placed a red cap (W3012845) on the line to the bag.

Added Human Albumin 25% to 3000 mL Bag. Opened vented mini spike. Without compromising sterility of spike, ensured blue cap is securely fastened. Spiked the septum of a Human Albumin 25% bottle with the vented mini spike. NOTE: Ensured to not compromise the sterility of the spike. Repeated two times for a total of three (3) spiked Human Albumin 25% bottles. Removed the blue cap from one vented mini spike and attach a 60 mL syringe to the Human Serum Albumin 25% bottle. Draw up 60 mL of Human Serum Albumin 25%. It may be necessary to use more than one bottle of Human Serum Albumin 25%. If necessary, disconnect the syringe from the vented mini spike and connect it to the next vented mini spike in a Human Serum Albumin 25% bottle. Once 60 mL has been obtained, remove the syringe from the vented mini spike. Attach syringe to needleless injection port on 3000 mL Origen bag filled with Plasmalyte-A. Dispensed all of the Human Albumin 25%. Repeated to obtain a final volume of 120.0 mL of Human Albumin 25%. Gently mixed the bag after all of the Human Albumin 25% had been added. Labeled as "LOVO-Wash Buffer" and assign a 24 hour expiry.

Prepared IL-2 Diluent. Using a 10 mL syringe, removed 5.0 mL of LOVO Wash Buffer using the needleless injection port on the LOVO Wash Buffer bag. Dispensed LOVO wash buffer into a 50 mL conical tube and label as "IL-2 Diluent".

CRF Blank Bag LOVO Wash Buffer Aliquotted. Using a 100 mL syringe, drew up 70.0 mL of LOVO Wash Buffer from the needleless injection port. NOTE: Wiped the needleless injection port with an alcohol pad before each use. Placed a red cap on the syringe and label as "blank cryo bag" and lot number. NOTE: Held the syringe at room temp until needed in Step 8.14.3

Completed Wash Buffer Prep. Closed all clamps on the LOVO Wash Buffer bag.

Thawed IL-2. Thawed one 1.1 mL of IL-2 ($6 \times 10^6$ IU/mL), until all ice has melted. Record IL-2 Lot number and Expiry. NOTE: Ensured IL-2 label is attached.

IL-2 Preparation. Added 50 µL IL-2 stock ($6 \times 10^6$ IU/mL) to the 50 mL conical tube labeled "IL-2 Diluent."

IL-2 Preparation. Relabeled conical as "IL-2 $6 \times 104$", the date, lot number, and 24 hour expiry. Cap and store at 2-8° C.

Cryopreservation Prep. Placed 5 cryo-cassettes at 2-8° C. to precondition them for final product cryopreservation.

Prepared Cell Count Dilutions. In the BSC, added 4.5 mL of AIM-V Media that has been labelled with lot number and "For Cell Count Dilutions" to 4 separate 15 mL conical tubes and labeled the tubes.

Prepared Cell Counts. Labeled 4 cryovials with vial number (1-4).

Day 22 TIL Harvest

Monitored the incubator. Incubator Parameters Temperature LED display: 37±2.0° C., $CO_2$ Percentage: 5%±1.5%.

Removed G-Rex500MCS Flasks from Incubator. Check flasks and confirm incubation parameters were met before removing G-Rex500MCS from incubator (incubation time).

Prepared TIL collection bag Labeled a 3000 mL collection bag as "TIL Suspension", lot number, and initial/date.

Sealed off extra connections. Heat sealed off two leur connections on the collection bag near the end of each connection.

GatheRex Setup. Sterile welded (per Process Note 5.11) the red media removal line from the G-Rex500MCS to the 10 L labtainer bag prepared above. NOTE: Referenced Process Note 5.16 for use of multiple GatheRex devices. Sterile welded (per Process Note 5.11) the clear cell removal line from the G-Rex500MCS to the TIL Suspension collection bag prepared above. Placed the G-Rex500MCS flask on the left side of the GatheRex. Placed the supernatant Labtainer bag and pooled TIL suspension collection bag to the right side. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex. Attached the gas line from the GatheRex to the sterile filter of the G-Rex500MCS. Before removing the supernatant from the G-Rex500MCS, ensured all clamps on the cell removal lines were closed.

Volume Reduction. Transferred ~4.5 L of supernatant from the G-Rex500MCS to the Supernatant bag. Visually inspected G-Rex500MCS to ensure flask is level and media had been reduced to the end of the aspirating dip tube. Repeat step if needed.

Prepared flask for TIL Harvest. After removal of the supernatant, closed all clamps to the red line.

Initiated collection of TIL. Recorded the start time of the TIL harvest. Vigorously tap flask and swirl media to release cells. Performed an inspection of the flask to ensure all cells have detached. Placed "TIL Suspension" 3000 mL collection bag on dry wipes on a flat surface. Tilted the flask to ensure hose is at the edge of the flask. NOTE: If the cell collection hose was not at the junction of the wall and bottom membrane, rapping the flask while tilted at a 45° angle is usually sufficient to properly position the hose.

TIL Harvest. Released all clamps leading to the TIL suspension collection bag. Using the GatheRex, transferred the TIL suspension into the 3000 mL collection bag. NOTE: Maintained the tilted edge until all cells and media were collected. Inspect membrane for adherent cells.

Rinsed flask membrane. Rinsed the bottom of the G-Rex500MCS. Covered ~¼ of gas exchange membrane with rinse media.

Close dclamps on G-Rex500MCS. Ensure all clamps are closed.

Heat sealed. Heat seal the collection bag containing the TIL as close to the weld as possible so that the overall tubing length remained approximately the same. Heat sealed the Supernatant bag.

Completed harvest of remaining G-Rex 500 MCS flasks. Repeat steps above, pooling all TIL into the same collection bag. It was necessary to replace the 101 supernatant bag after every 2nd flask.

Prepared LOVO source bag. Obtained a new 3000 mL collection bag. Labeled as "LOVO Source Bag", lot number, and Initial/Date. Heat sealed the tubing on the "LOVO Source bag", removing the female luers, leaving enough line to weld.

Weighed LOVO Source Bag. Placed an appropriately sized plastic bin on the scale and tare. Place the LOVO Source Bag, including ports and lines, in the bin and record the dry weight.

Transferred cell suspension into LOVO source bag. Closed all clamps of a 170 µm gravity blood filter.

Transferred cell suspension into LOVO source bag. Sterile welded the long terminal end of the gravity blood filter to the LOVO source bag. Sterile welded one of the two source lines of the filter to "pooled TIL suspension" collection bag. Once weld was complete, heat sealed the unused line on the filter to remove it. Opened all necessary clamps and elevate the TIL suspension by hanging the collection bag on an IV pole to initiate gravity-flow transfer of TIL through the blood filter and into the LOVO source bag. Gently rotated or knead the TIL Suspension bag while draining in order to keep the TIL in even suspension.

Closed all clamps. Once all TIL were transferred to the LOVO source bag, closed all clamps.

Heat Sealed. Heat sealed (per Process Note 5.12) as close to weld as possible to remove gravity blood filter.

Removed Cell Counts Samples. In the BSC, using separate 3 mL syringes for each sample, removed 4×1.0 mL cell count samples from the LOVO source bag using the needless injection port. Placed samples in the cryovials prepared in Step 8.11.36.

Performed Cell Counts. Performed cell counts and calculations utilizing NC-200. Diluted cell count samples initially by adding 0.5 mL of cell suspension into 4.5 mL of AIM-V media prepared above. This gave a 1:10 dilution.

Recorded Cell Count and Sample Volumes. Calculated Total Viable TIL Cells. If Total Viable cells $\geq 1.5 \times 10^9$, proceeded. Calculate Total Nucleated Cells.

Prepared *Mycoplasma* Diluent. In the BSC, removed 10.0 mL from one supernatant bag via luer sample port and placed in a 15 mL conical. Label 15 mL conical "*Mycoplasma* Diluent".

LOVO

Turned on the LOVO and started the "TIL G-Rex Harvest" protocol and followed screen prompts. Buffer type was PlasmaLyte. Followed the LOVO touch screen prompts.

Determined the final product target volume. Using the total nucleated cells (TNC) value and the chart below, determined the final product target volume and recorded (mL).

TABLE 30

| Calculate final product volume | |
|---|---|
| Cell Range | Final Product (Retentate) Volume to Target (mL) |
| 0 < Total (Viable + Dead) Cells $\leq 7.1 \times 10^{10}$ | 165 |
| $7.1 \times 10^{10}$ < Total (Viable + Dead) Cells $\leq 1.1 \times 10^{11}$ | 215 |

TABLE 30-continued

| Calculate final product volume | |
|---|---|
| Cell Range | Final Product (Retentate) Volume to Target (mL) |
| $1.1 \times 10^{11}$ < Total (Viable + Dead) Cells $\leq 1.5 \times 10^{11}$ | 265 |

Followed the LOVO touch screen prompts.

Loaded disposable kit. Prior to loading the disposable kit, wipe pressure sensor port with an alcohol wipe followed by a lint-free wipe. Load the disposable kit. Follow screen directions on loading the disposable kit.

Removed filtrate bag. When the standard LOVO disposable kit had been loaded, touched the Next button. The Container Information and Location Screen displayed. Removed filtrate bag from scale Ensured Filtrate container was New and Off-Scale Entered Filtrate capacity. Sterile welded a LOVO Ancillary Bag onto the male luer line of the existing Filtrate Bag. Ensured all clamps are open and fluid path is clear. Touch the Filtrate Container Capacity entry field. A numeric keypad displays. Enter the total new Filtrate capacity (5,000 mL). Touch the button to accept the entry. NOTE: Estimated Filtrate Volume should not exceed 5000 mL.

Placed Filtrate container on benchtop. NOTE: If tubing was removed from the F clamp during welding, placed the tubing back into the clamp. Placed the new Filtrate container on the benchtop. DID NOT hang the Filtrate bag on weigh scale #3. Weigh scale #3 will be empty during the procedure.

Followed the LOVO touch screen prompts after changes to the filtrate container.

Ensured kit was loaded properly. The Disposable Kit Dry Checks overlay displays. Checked that the kit was loaded properly and all clamps were open. Checked all tubing for kinks or other obstructions and correct if possible. Ensured kit was properly installed and check all Robert's clamps. Pressed the Yes button. All LOVO mechanical clamps closed automatically and the Checking Disposable Kit Installation screen displays. The LOVO went through a series of pressurizing steps to check the kit.

Kit Check Results. If the Kit check passed, proceeded to the next step. *If No, a second Kit Check could be performed after checks have been complete. *If No, Checked all tubing for kinks or other obstructions and correct *If No, Ensured kit was properly installed and check all Robert's clamps. If the 2nd kit check failed: Contact area management and prepare to installation of new kit in Section 10.0. Repeat Step 8.13.23-Step 8.13.30 needed.

Attached PlasmaLyte. The Connect Solutions screen displayed. The wash value would always be 3000 mL. Entered this value on screen.

Sterile welded the 3000 mL bag of PlasmaLyte to the tubing passing through Clamp 1. Hung the PlasmaLyte bag on an IV pole placing both corner bag loops on the hook.

Verified that the PlasmaLyte was attached. Opened any plastic clamps. Verified that the Solution Volume entry was 3000 mL. Touched the "Next" button. The Disposable Kit Prime overlay displayed. Verified that the PlasmaLyte was attached and any welds and plastic clamps on the tubing leading to the PlasmaLyte bag were open, then touched the Yes button Observed that the PlasmaLyte is moving. Disposable kit prime starts and the Priming Disposable Kit Screen displays.

Visually observed that PlasmaLyte moving through the tubing connected to the bag of PlasmaLyte. If no fluid was moving, pressed the Pause Button on the screen and determined if a clamp or weld was still closed. Once the problem had been solved, pressed the Resume button on the screen to resume the Disposable Kit Prime. Followed the LOVO touch screen prompts.

Attached Source container to tubing. Sterile weld the LOVO Source Bag prepared in Step 8.12.31 to the tubing passing through Clamp S per Process Note 5.11. It could be necessary to remove the tubing from the clamp. Note: Made sure to replace source tubing into the S clamp if removed.

Hung Source container. Hung the Source container on the IV pole placing both corner bag loops on the hook. DID NOT hang the Source on weigh scale #1. Opened all clamps to the source bag.

Verified Source container was attached. Touched the Next button. The Source Prime overlay displayed. Verified that the Source was attached to the disposable kit, and that any welds and plastic clamps on the tubing leading to the Source were open. Touched the Yes button.

Confirm PlasmaLyte was moving. Source prime started and the Priming Source Screen displayed. Visually observed that PlasmaLyte is moving through the tubing attached to the Source bag. If no fluid is moving, press the Pause Button on the screen and determine if a clamp or weld is still closed. Once the problem was solved, pressed the Resume button on the screen to resume the Source Prime.

Started Procedure Screen. When the Source prime finishes successfully, the Start Procedure Screen displays. Pressed Start, the "Pre-Wash Cycle 1" pause screen appears immediately after pressing start.

Inverted In Process Bag. Removed the In Process Bag from weigh scale #2 (can also remove tubing from the In Process top port tubing guide) and manually invert it to allow the wash buffer added during the disposable kit prime step to coat all interior surfaces of the bag. Re-hang the In Process Bag on weigh scale #2 (label on the bag was facing to the left). Replace the top port tubing in the tubing guide, if it was removed.

Inverted Source bag. Before pressing the Start button, mixed the Source bag without removing it from the IV pole by massaging the bag corners and gently agitating the cells to create a homogeneous cell suspension. Pressed the Resume button. The LOVO started processing fluid from the Source bag and the Wash Cycle 1 Screen displays.

Source Rinse Pause. The Rinse Source Pause screen displayed once the source container was drained and the LOVO had added wash buffer to the Source bag. Without removing the Source bag from IV pole, massaged the corners and mixed well. Pressed Resume.

Mixed In Process Bag Pause. To prepare cells for another pass through the spinner, the In Process Bag was diluted with wash buffer. After adding the wash buffer to the In Process Bag, the LOVO pauses automatically and displays the "Mix In Process Bag" Pause Screen. Without removing the bag from the weigh scale, mixed the product well by gently squeezing the bag. Press Resume.

Massaged In Process Corners Pause. When the In Process Bag was empty, wash buffer was added to the bottom port of the In Process Bag to rinse the bag. After adding the rinse fluid, the LOVO paused automatically and displayed the "Massage IP corners" Pause Screen. When the "Massage IP corners" Pause Screen displayed, DO NOT remove the bag from weigh scale #2. With the In Process Bag still hanging on weigh scale #2, massage the corners of the bag to bring any residual cells into suspension. Ensured the bag was not swinging on the weigh scale and pressed the Resume button.

Waited for Remove Products Screen. At the end of the LOVO procedure, the Remove Products Screen displayed. When this Screen displays, all bags on the LOVO kit could be manipulated. Note: Did not touch any bags until the Remove Products displayed.

Removed retentate bag. Placed a hemostat on the tubing very close to the port on the Retentate bag to keep the cell suspension from settling into the tubing. Heat sealed (per Process Note 5.12) below the hemostat, making sure to maintain enough line to weld in Step 8.13.48. Removed the retentate bag.

Prepared retentate bag for formulation. Welded the female luer lock end of a 4" Plasma Transfer Set to the retentate bag. Transferred the retentate bag.

Removed Products. Followed the instructions on the Remove Products Screen. Closed all clamps on the LOVO kit to prevent fluid movement.

Removed Products. Touched the Next button. All LOVO mechanical clamps opened and the Remove Kit Screen displayed.

Recorded Data. Followed the instructions on the Remove Kit screen. Touched the "Next" button. All LOVO mechanical clamps close and the Results Summary Screen displays. Recorded the data from the results summary screen. Closed all pumps and filter support. Removed the kit when prompted to do so by the LOVO. All Times recorded were recorded directly from the LOVO.

Final Formulation and Fill

Target volume/bag calculation. From Table 31 below, selected the number of CS750 bags to be filled, target fill volume per bag, volume removed for retain per bag, and final target volume per bag that corresponded to the Volume of LOVO Retentate from above.

TABLE 31

Target volume/bag calculation

| Volume of LOVO product | Volume of CS10 to add to product | Final Predicted Volume of formulated product | Number of bags to be | Target Fill Volume per bag | Volume removed for retain per bag | Final Target Volume per bag |
|---|---|---|---|---|---|---|
| 165 mL | 165 mL | 330 mL | 3 | 107 mL | 7 mL | 100 mL |
| 215 mL | 215 mL | 430 mL | 4 | 105 mL | 5 mL | 100 mL |
| 265 mL | 265 mL | 530 mL | 4 | 130 mL | 5 mL | 125 mL |

Prepared CRF Blank. Calculated volume of CS-10 and LOVO wash buffer to formulate blank bag.

TABLE 32

Calculated volumes.

| Final Target Volume per Bag A | Blank LOVO Wash Buffer Volume B = A/2 | Blank CS-10 Volume (mL) C = B |
|---|---|---|
| mL | mL | mL |

Prepared CRF Blank. Outside of the BSC, using the syringe of LOVO Wash Buffer prepared in above, added volume calculated to an empty CS750 bag via luer connection. Note: Blank CS750 bag formulation does not need to be done aseptically. Using an appropriately sized syringe, added the volume of CS-10 calculated to the same CS750 bag prepared above. Placed a red cap on the CS750 bag. Removed as much air as possible from the CS-750 bag as possible. Heat sealed the CS750 bag as close to the bag as possible, removing the tubing. Label CS750 bag with "CRF Blank", lot number, and initial/date. Placed the CRF Blank on cold packs until it was placed in the CRF.

Calculated required volume of IL-2. Calculated the volume of IL-2 to add to the Final Product

TABLE 33

Calculated IL-2 volume

| Parameter | Formula | Result |
|---|---|---|
| Final Retentate Volume | Step 8.13.51 | A. mL |
| Final Formulated Volume | B = A × 2 | B. mL |
| Final IL-2 Concentration desired (IU/mL) | 300 IU/mL | C. 300 IU/mL |
| IU of IL-2 Required | D = B × C | D. IU |
| IL-2 Working Stock from Step 8.11.33 | $6 \times 10^4$ IU/mL | E. $6 \times 10^4$ IU/mL |
| Volume of IL-2 to Add to Final Product | F = D ÷ E | F. mL |

Assembled Connect apparatus. Sterile welded a 4S-4M60 to a CC2 Cell Connect replacing a single spike of the Cell Connect apparatus with the 4-spike end of the 4S-4M60 manifold.

Assembled Connected apparatus. Sterile welded the CS750 Cryobags to the harness prepared above, replacing one of the four male luer ends (E) with each bag. Welded (per Process Note 5.11) CS-10 bags to spikes of the 4S-4M60. Kept CS-10 cold by placing the bags between two cold packs conditioned at 2-8° C.

Prepared TIL with IL-2. Using an appropriately sized syringe, removed amount of IL-2 determined above from the "IL-2 6×104" aliquot. Connect the syringe to the retentate bag prepared above via the Luer connection and inject IL-2. Clear the line by pushing air from the syringe through the line.

Labeled Formulated TIL Bag. Closed the clamp on the transfer set and label bag as "Formulated TIL" and passed the bag out of the BSC.

Added the Formulated TIL bag to the apparatus. Once IL-2 had been added, welded the "Formulated TIL" bag to the remaining spike on the apparatus.

Added CS10. Passed the assembled apparatus with attached Formulated TIL, CS-750 bags, and CS-10 into the BSC. NOTE: The CS-10 bag and all CS-750 bags were placed between two cold packs preconditioned at 2-8° C. Did not place Formulated TIL bag on cold packs. Ensured all clamps were closed on the apparatus. Turn the stopcock so the syringe was closed.

Switched Syringes. Drew ~10 mL of air into a 100 mL syringe and replaced the 60 mL syringe on the apparatus.

Added CS10. Turned stopcock so that the line to the CS750 bags is closed. Open clamps to the CS-10 bags and pull volume calculated above into syringe. NOTE: Multiple syringes will be used to add appropriate volume of CS-10. Closed clamps to CS-10 and open clamps to the Formulated TIL bag and add the CS-10. Add first 10.0 mL of CS10 at approximately 10.0 mL/minute. Add remaining CS-10 at approximate rate of 1.0 mL/sec. Note: Multiple syringes were used to add appropriate volume of CS-10. Recorded time. NOTE: The target time from first addition of CS-10 to beginning of freeze is 30 minutes. Recorded the volume of each CS10 addition and the total volume added. Closed all clamps to the CS10 bags.

Prepared CS-750 bags. Turned the stopcock so that the syringe was open. Opened clamps to the Formulated TIL bag and drew up suspension stopping just before the suspension reaches the stopcock. Closed clamps to the formulated TIL bag. Turned stopcock so that it was open to the empty CS750 final product bags. Using a new syringe, removed as much air as possible from the CS750 final product bags by drawing the air out. While maintaining pressure on the syringe plunger, clamped the bags shut. Draw ~20 mL air into a new 100 mL syringe and connect to the apparatus. NOTE: Each CS-750 final product bag should be between two cold packs to keep formulated TIL suspension cold.

Dispensed cells. Turned the stopcock so the line to the final product bags was closed. Pulled the volume calculated above from the Formulated TIL bag into the syringe. NOTE: Multiple syringes could be used to obtain correct volume. Turned the stopcock so the line to the formulated TIL bag is closed. Working with one final product bag at a time, dispense cells into a final product bag. Recorded volume of cells added to each CS750 bag above. Cleared the line with air from the syringe so that the cells are even with the top of the spike port. Closed the clamp on the filled bag. Repeated steps for each final product bag, gently mixing formulated TIL bag between each. Recorded volume of TIL placed in each final product bag below.

Removed air from final product bags and take retain. Once the last final product bag was filled, closed all clamps. Drew 10 mL of air into a new 100 mL syringe and replace the syringe on the apparatus. Manipulating a single bag at a time, drew all of the air from each product bag plus the volume of product for retain determined above. NOTE: Upon removal of sample volume, inverted the syringe and used air to clear the line to the top port of the product bag. Clamped the line to the bag once the retain volume and air was removed.

Recorded volume of retain removed from each bag.

Dispensed Retain. Dispensed retain into a 50 mL conical tube and label tube as "Retain" and lot number. Repeat for each bag.

Prepared final product for cryopreservation. With a hemostat, clamped the lines close to the bags. Removed syringe and red cap luer connection on the apparatus that the syringe was on. Passed apparatus out of the BSC. Heat sealed (per Process Note 5.12) at F, removing the empty retentate bag and the CS-10 bags. NOTE: Retained luer connection for syringe on the apparatus. Disposed of empty retentate and CS-10 Bags.

Labeled final product bags. Attached sample final product label below.

Prepared final product for cryopreservation. Held the cryobags on cold pack or at 2-8° C. until cryopreservation.

Removed Cell Count Sample. Using an appropriately sized pipette, remove 2.0 mL of retain removed above and placed in a 15 mL conical tube to be used for cell counts.

Performed Cell Counts. Performed cell counts and calculations utilizing the NC-200. NOTE: Diluted only one sample to appropriate dilution to verify dilution is sufficient. Diluted additional samples to appropriate dilution factor and proceed with counts. Recorded Cell Count sample volumes. NOTE: If no dilution needed, "Sample [μL]"=200, "Dilution [μL]"=0. Determined the Average of Viable Cell Concentration and Viability of the cell counts performed.

Calculated Flow Cytometry Sample. Performed calculation to ensure sufficient cell concentration for flow cytometry sampling.

TABLE 34

Calculate flow cytometry cell concentration

| Viable Cell Concentration A | Target Volume Required for $6 \times 10^7$ TVC B = $6 \times 10^7$ cells/A | Is B ≤1.0 mL? (Yes/No**) |
|---|---|---|
| | mL | |

Calculated IFN-γ. Sample Performed calculation to ensure sufficient cell concentration for IFN-γ sampling.

Heat Sealed. Once sample volumes had been determined, heat sealed Final Product Bags as close to the bags as possible to remove from the apparatus.

TABLE 35

Labeling and collection of samples

| Sample | Number of Containers | Sample Volume to Add to Each | Container Type |
|---|---|---|---|
| *Mycoplasma | 1 | 1.0 mL | 15 mL Conical |
| Endotoxin | 2 | 1.0 mL | 2 mL Cryovial |
| Gram Stain | 1 | 1.0 mL | 2 mL Cryovial |
| IFN-g | 1 | 1.0 mL | 2 mL Cryovial |
| Flow Cytometry | 1 | 1.0 mL | 2 mL Cryovial |
| **Bac-T Sterility | 2 | 1.0 mL | Bac-T Bottle |
| QC Retain | 4 | 1.0 mL | 2 mL Cryovial |
| Satellite Vials | 10 | 0.5 mL | 2 mL Cryovial |

For the *Mycoplasma* sample, add formulated cell suspension volume to the 15 mL conical labelled "*Mycoplasma* Diluent" from above. Sterility & BacT. Testing Sampling. In the BSC, remove a 1.0 mL sample from the retained cell suspension collected in above using an appropriately sized syringe and inoculate the anaerobic bottle. Repeat the above for the aerobic bottle.

Labeled and stored samples. Labeled all samples with sample plan inventory labels and store appropriately until transfer. Proceeded to next steps for cryopreservation of final product and samples.

Final Product Cryopreservation

Prepared Controlled Rate Freezer. Verified the CRF had been set up prior to freeze. Record CRF Equipment. Cryopreservation is performed.

Set up CRF probes. Punctured the septum on the CRF blank bag. Inserted the 6 mL vial temperature probe.

Placed final product and samples in CRF. Placed blank bag into preconditioned cassette and transferred into the approximate middle of the CRF rack. Transferred final product cassettes into CRF rack and vials into CRF vial rack. Transferred product racks and vial racks into the CRF. Recorded the time that the product is transferred into the CRF and the chamber temperature.

Determined the time needed to reach 4° C.±1.5° C. and proceed with the CRF run. Once the chamber temperature reached 4° C.±1.5° C., started the run. Recorded time.

Completed and Stored. Stopped the CRF after the completion of the run. Remove cassettes and vials from CRF. Transferred cassettes and vials to vapor phase LN2 for storage.

Example 12: Novel Cryopreserved Tumor Infiltrating Lymphocytes (LN-144) Administered to Patients with Metastatic Melanoma Demonstrated Efficacy and Tolerability in a Multicenter Phase 2 Clinical Trial Background The safety and efficacy of adoptive cell therapy (ACT) utilizing tumor infiltrating lymphocytes (TIL) has been studied in hundreds of patients with metastatic melanoma, and has demonstrated meaningful and durable objective response rates (ORR).[1] In an ongoing Phase 2 trial, C-144-01 utilizing centralized GMP manufacturing of TIL, both non-cryopreserved Generation 1 (Gen 1) and cryopreserved Generation 2 (Gen 2) TIL manufacturing processes were assessed.

Figure 25:
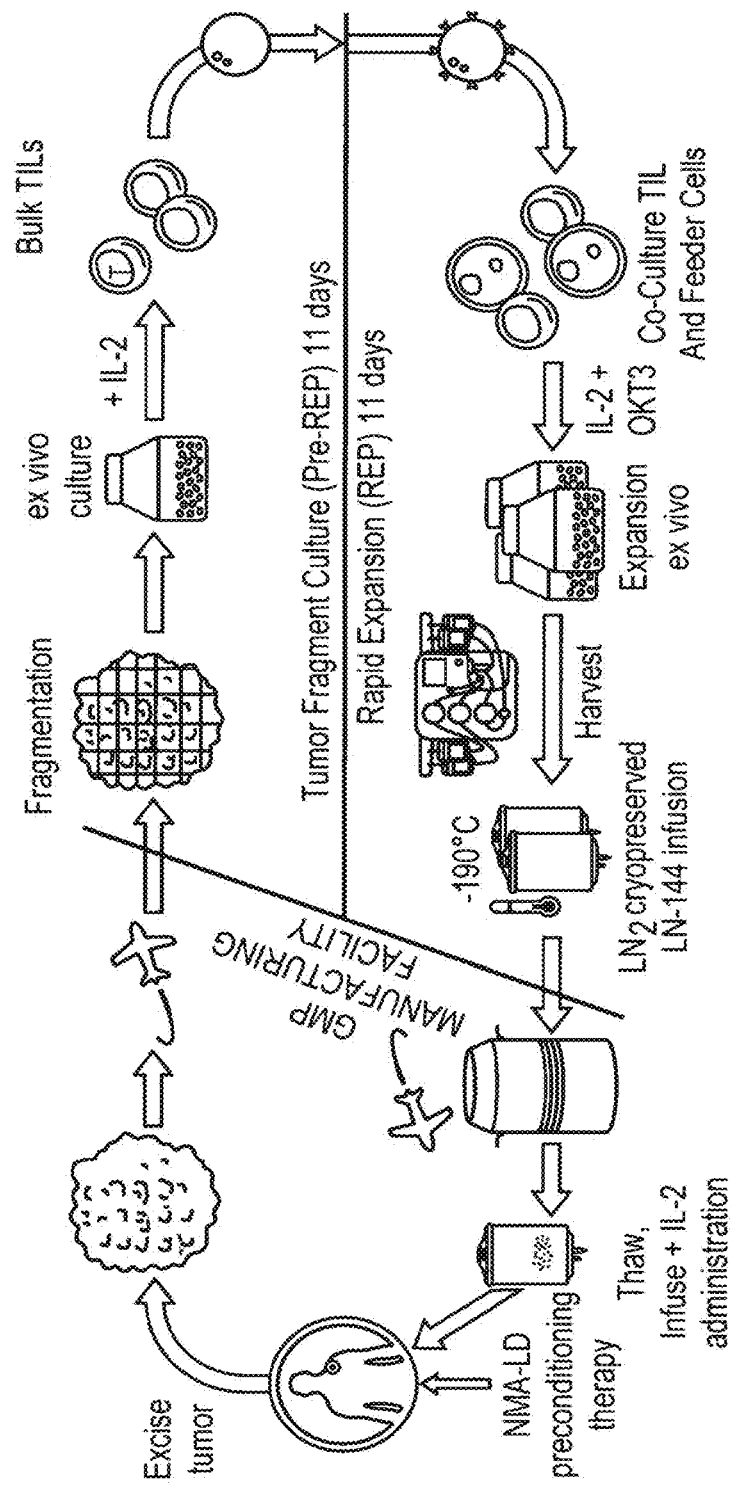
FIG. 25: Scheme of Gen 2 cryopreserved LN-144 manufacturing process.

Gen 1 is approximately 5-6 weeks in duration of manufacturing (administered in Cohort 1 of C-144-01 study), while Gen 2 is 22 days in duration of manufacturing (process 2A, administered in Cohort 2 of C-144-01 study). Preliminary data from Cohort 1 patients infused with the Gen 1 LN-144 manufactured product, was encouraging in treating post-PD-1 metastatic melanoma patients as the TIL therapy produced responses.[2] Benefits of Gen 2 included: (A) reduction in the time patients and physicians wait to infuse TIL to patient; (B) cryopreservation permits flexibility in scheduling, distribution, and delivery; and (C) reduction of manufacturing costs. Preliminary data from Cohort 2 is presented herein. FIG. 25 shows an embodiment of the Gen 2 cryopreserved LN-144 manufacturing process (process 2A).

Study Design: C-144-01 Phase 2 Trial in Metastatic Melanoma

Phase 2, Multicenter, 3-Cohort Study to Assess the Efficacy and Safety of Autologous Tumor Infiltrating Lymphocytes (LN-144) for Treatment of Patients with Metastatic Melanoma.

Key Inclusion Criteria: (1) Measurable metastatic melanoma and ≥1 lesion resectable for TIL generation; (2) Progression on at least one prior line of systemic therapy; (3) Age≥18; and (4) ECOG PS 0-1.

Figure 26:
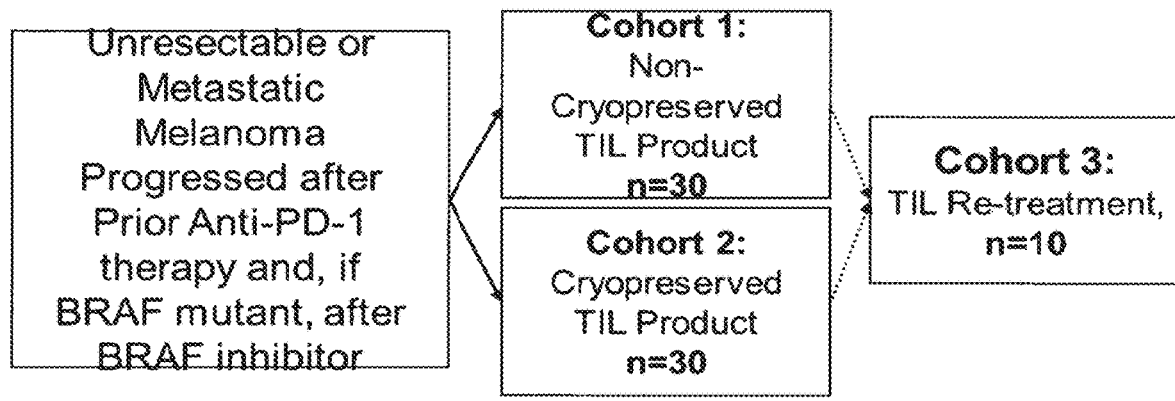
FIG. 26: Scheme of study design of multicenter phase 2 clinical trial of novel cryopreserved TILs administered to patients with metastatic melanoma.

Treatment Cohorts: (1) Non-Cryopreserved LN-144 product; (2) Cryopreserved LN-144 product; and (3) Retreatment with LN-144 for patients without response or who progress after initial response. FIG. 26 shows the study design.

Endpoints: (1) Primary: Efficacy defined as ORR and (2) Secondary: Safety and Efficacy.

Methods

Cohort 2 Safety Set: 13 patients who underwent resection for the purpose of TIL generation and received any component of the study treatment.

Cohort 2 Efficacy Set: 9 patients who received the NMA-LD preconditioning, LN-144 infusion and at least one dose of IL-2, and had at least one efficacy assessment. 4 patients did not have an efficacy assessment at the time of the data cut.

Biomarker data has been shown for all available data read by the date of the data cut.

Results

FIG. 27 provides a table illustrating the Comparison Patient Characteristics from Cohort 1 (ASCO 2017) vs Cohort 2. Cohort 2 has: 4 median prior therapies; all patients have received prior anti-PD-1 and anti-CTLA-4; and had higher tumor burden reflected by greater sum of diameters (SOD) for target lesions and higher mean LDH at Baseline. FIG. 28 provides a table showing treatment emergent adverse events (≥30%).

Figure 29:
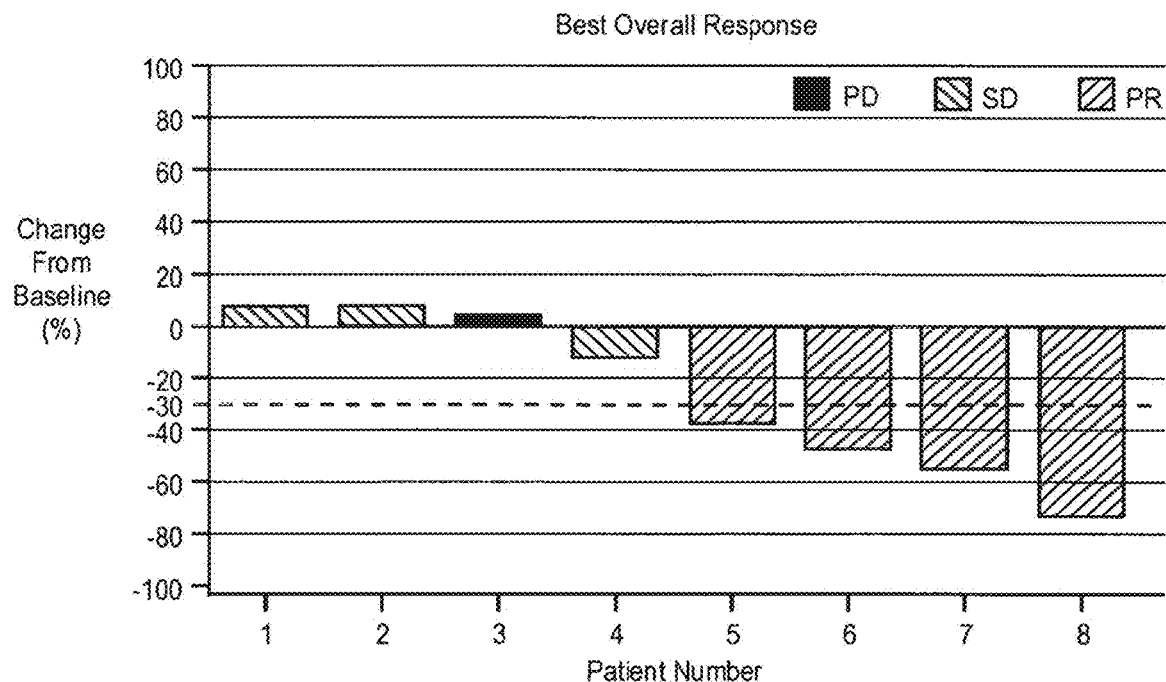
FIG. 29: Efficacy of the infusion product and TIL therapy.

For Cohort 2 (cryopreserved LN-144), the infusion product and TIL therapy characteristics were (1) mean number of TIL cells infused: $37 \times 10^9$, and (2) median number of IL-2 doses administrations was 4.5. FIG. 29 shows the efficacy of the infusion product and TIL therapy for Patients #1 to #8.

Figure 30:
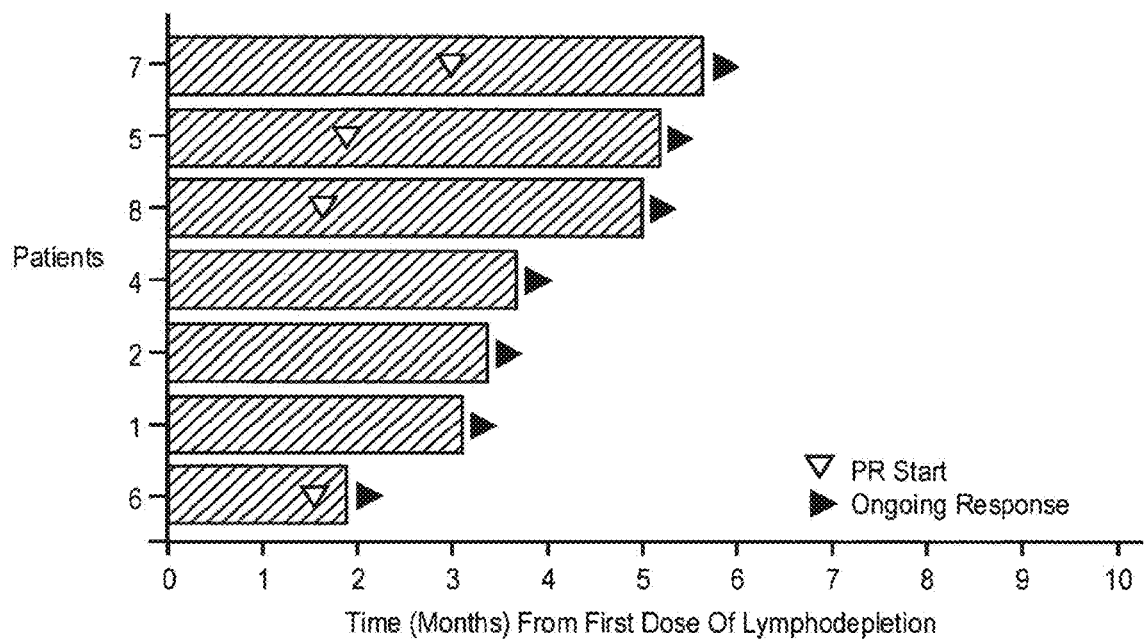
FIG. 30: Clinical status of response evaluable patients with SD or a better response.

FIG. 30 shows the clinical status of response evaluable patients with stable disease (SD) or a better response. A partial response (PR) for Patient 6 was unconfirmed as the patient did not reached the second efficacy assessment yet. One patient (Patient 9) passed away prior to the first assessment (still considered in the efficacy set).

Of the 9 patients in the efficacy set, one patient (Patient 9) was not evaluable (NE) due to melanoma-related death prior to first tumor assessment not represented on FIG. 30. Responses were seen in patients treated with Gen 2. The disease control rate (DCR) was 78%. Time to response was similar to Cohort 1. One patient (Patient 3) with progressive disease (PD) as best response was not included in the swim lane plot.

Figure 31:
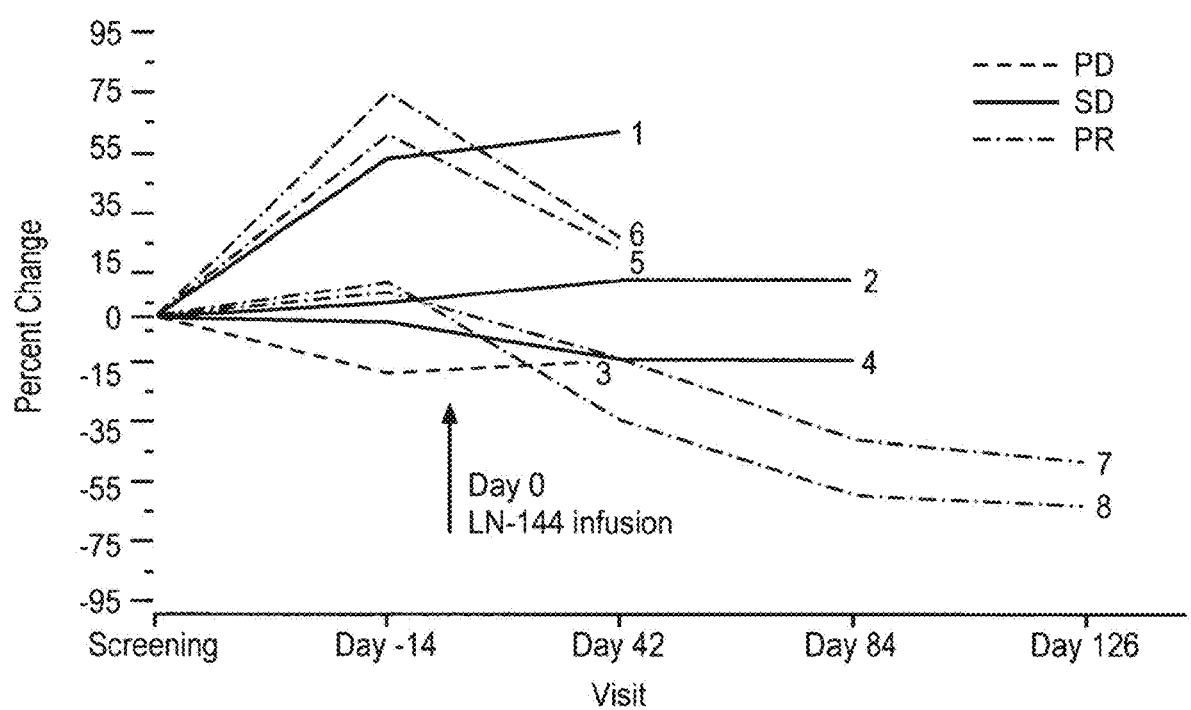
FIG. 31: Percent change in sum of diameters.

FIG. 31 shows the percent change in sum of diameters. Patient 9 had no post-LN-144 disease assessment due to melanoma-related death prior to Day 42. Day −14: % change of Sum of Diameters from Screening to Baseline (Day −14). Day −14 to Day 126: % change of SOD from Baseline. Day −14=Baseline. Day 0=LN-144 infusion.

Figure 32:
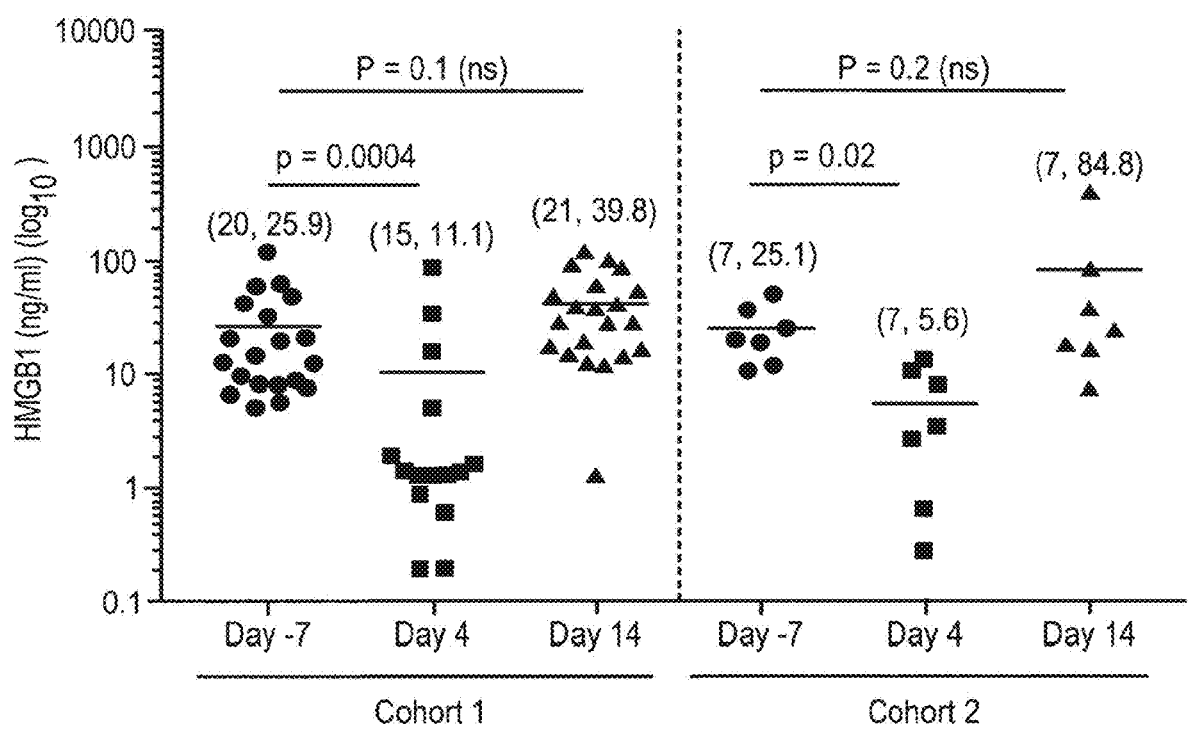
FIG. 32: An increase of HMGB1 level was observed upon TIL treatment.

Upon TIL treatment, an increase of HMGB1 was observed (FIG. 32). Plasma HMGB1 levels were measured using HMGB1 ELISA kit (Tecan US, Inc). Data shown represents fold change in HMGB1 levels pre (Day −7) and post (Day 4 and Day 14) LN-144 infusion in Cohort 1 and Cohort 2 patients (p values were calculated using two-tailed paired t-test based on log-transformed data). Sample size (bold and italicized) and mean (italicized) values are shown in parentheses for each time point. HMGB1 is secreted by activated immune cells and released by damaged tumor cells. The increased HMGB1 levels observed after treatment with LN-144 are therefore suggestive of an immune-mediated mechanism of anti-tumor activity.

Figure 33:
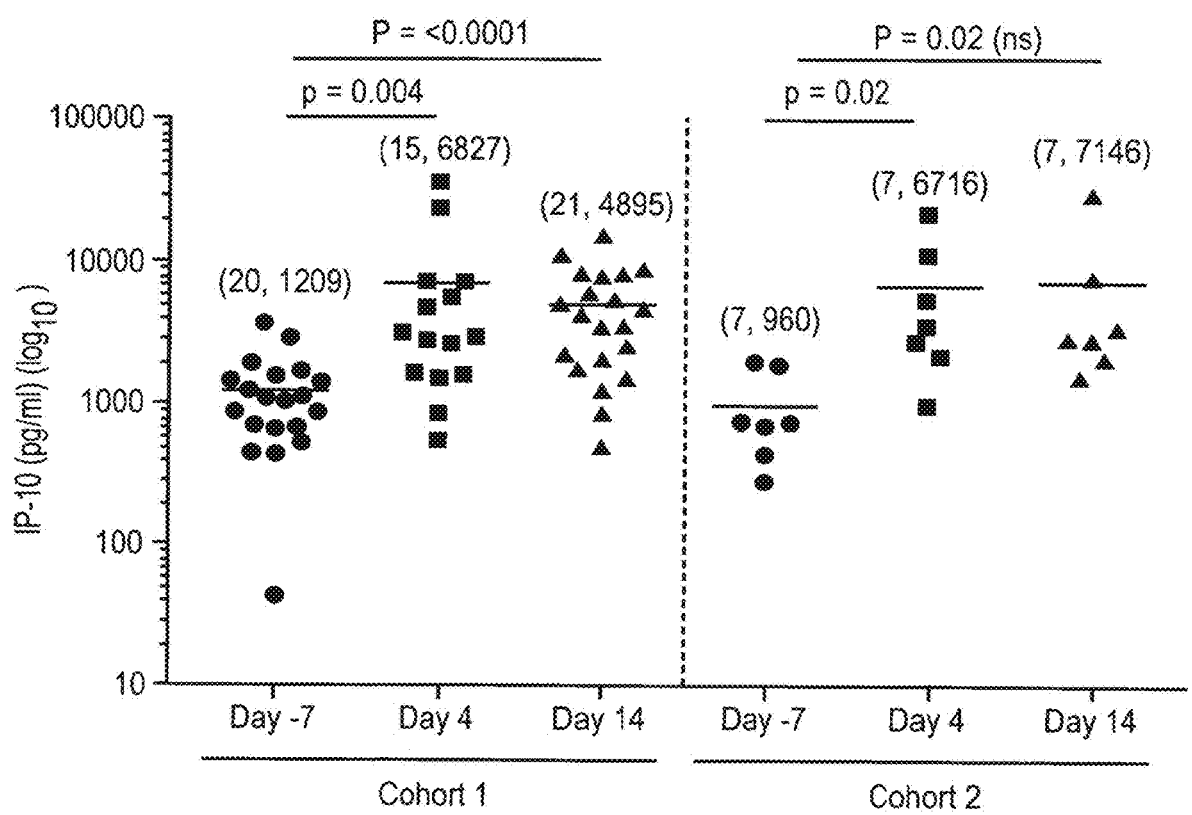
FIG. 33: An increase in the biomarker IL-10 was observed post-LN-144 infusion.
Figure 36:
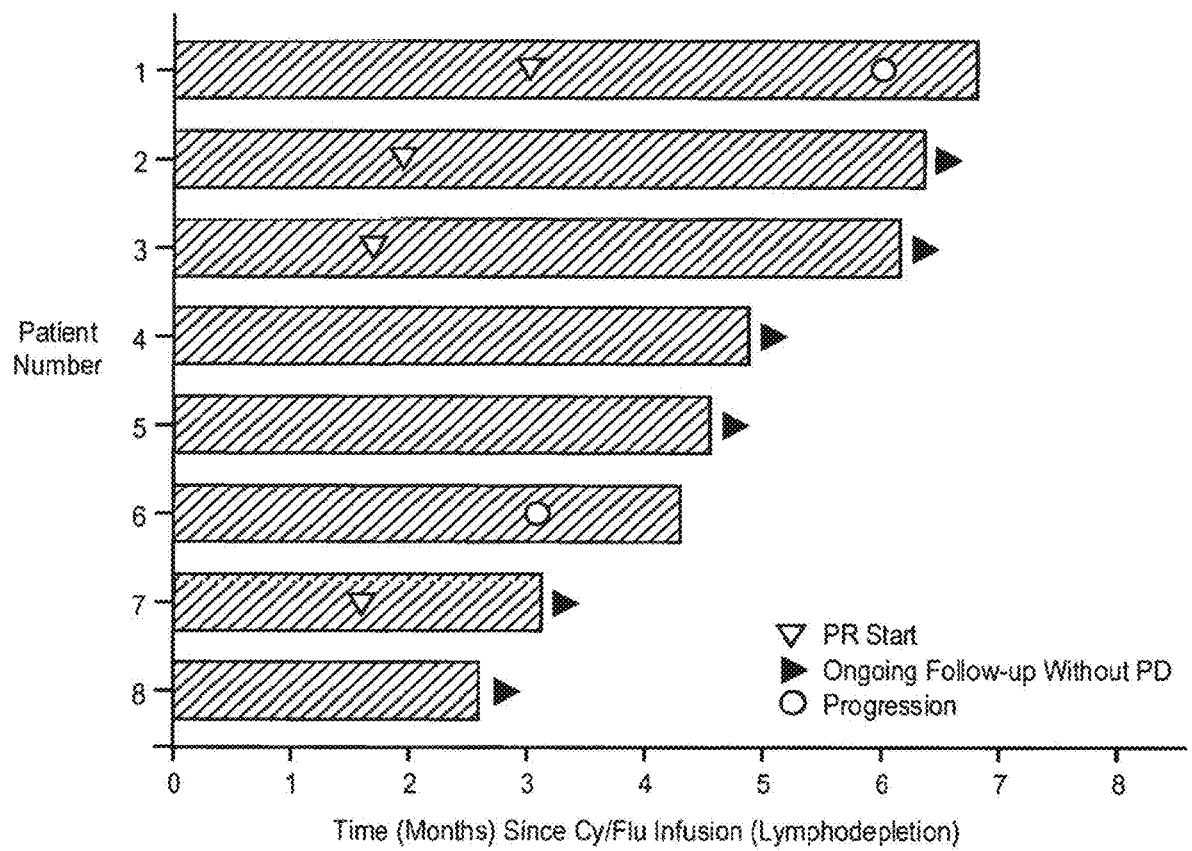
FIG. 36: Time to response for evaluable patients (stable disease or better) in Cohort 2 from the second data cut (N=17 patients). Of the 10 patients in the efficacy set, one patient (Patient 10) was not evaluable due to a melanoma-related death prior to the first tumor assessment not represented on the figure.
Figure 37:
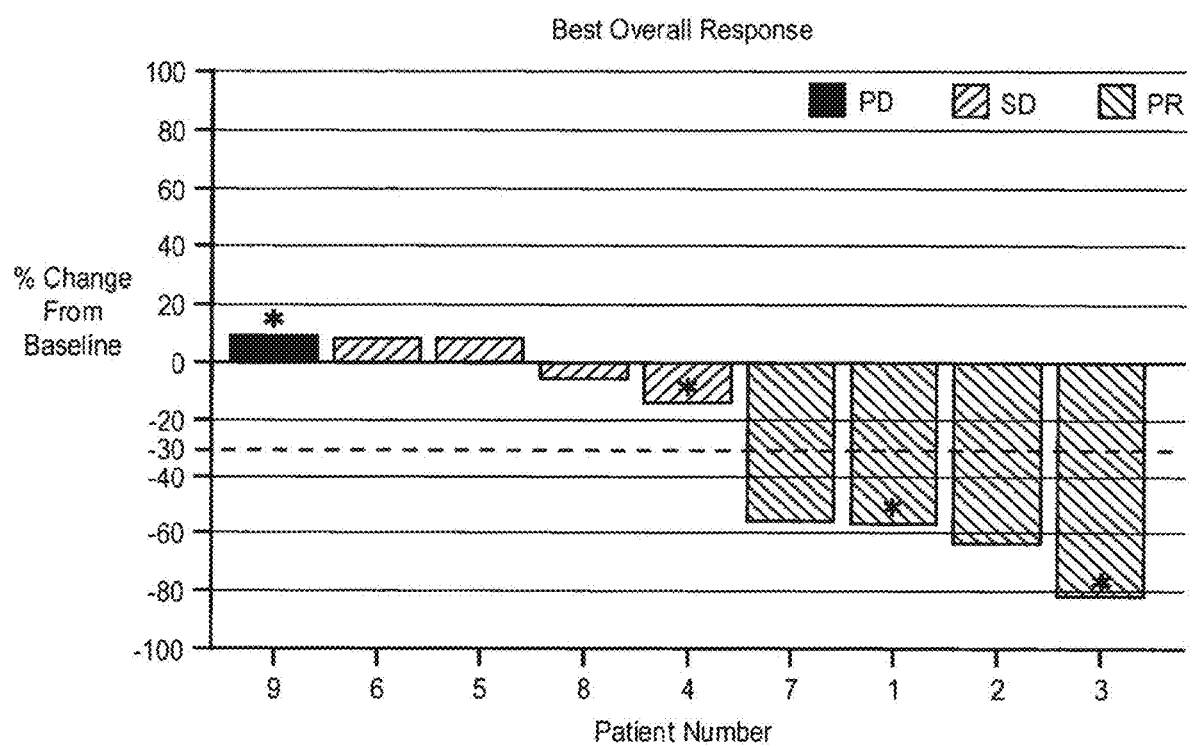
FIG. 37: Updated efficacy data for Cohort 2 from the second data cut (N=17 patients). The mean number of TILs infused is $34 \times 10^9$. The median number of prior therapies was 4.5. Patients with a BRAF mutation responded as well as patients with wild-type BRAF (a * refers to patients with a BRAF mutation). One patient (Patient 10) was not evaluable due to a melanoma-related death prior to the first tumor assessment but was still considered in the efficacy set. Abbreviations: PR, partial response; SD, stable disease; PD, progressive disease.
Figure 39:
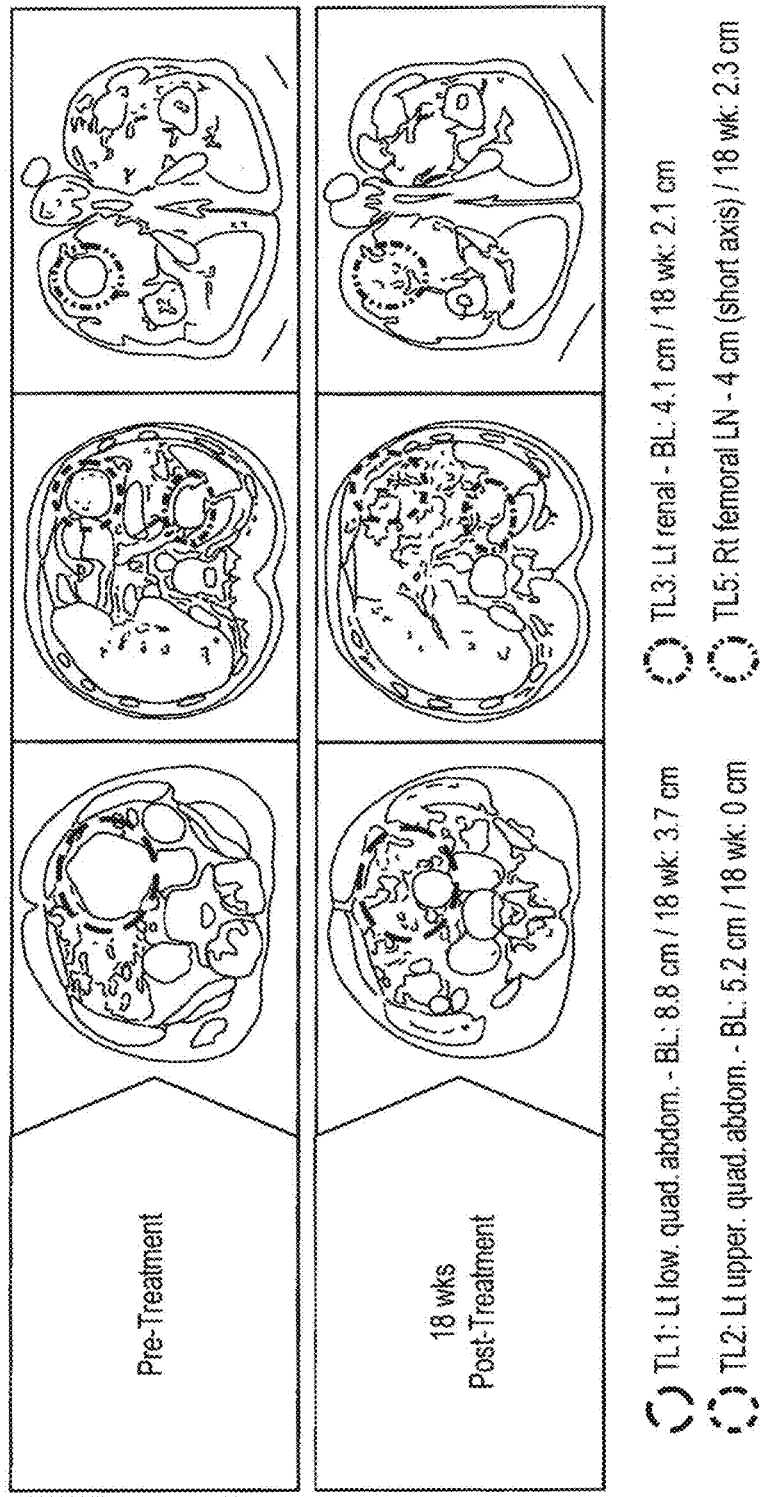
FIG. 39: Representative computed tomography scan of a patient (003-015) with a PR from Cohort 2, second data cut.
Figure 40:
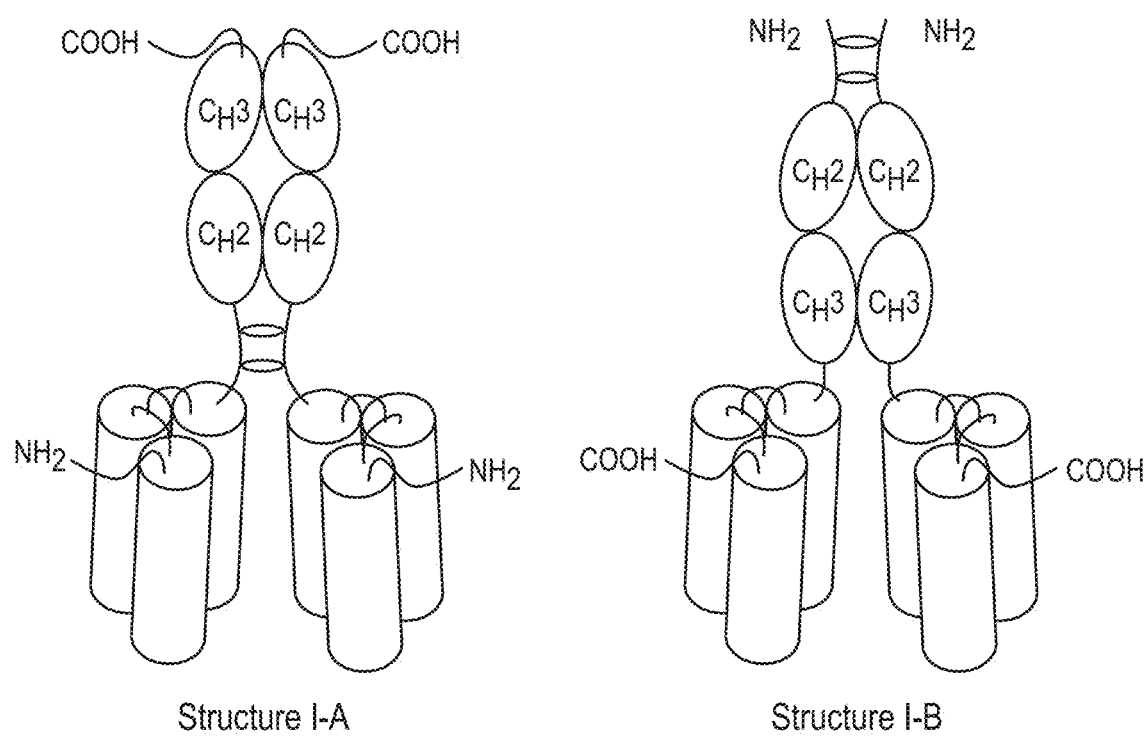
FIG. 40: Provides the structures I-A and I-B. The cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.

Plasma IP-10 levels were measured using Luminex assay. Data shown in FIG. 33 represents fold change in IP-10 levels pre (Day −7) and post (Day 4 and Day 14) LN-144 infusion in Cohort 1 and Cohort 2 patients (p values were calculated using two-tailed paired t-test based on log-transformed data). Sample size (bold and italicized) and mean (italicized) values are shown in parentheses for each time point. The post-LN-144 infusion increase in 1P-10 is being monitored to understand possible correlation with TIL persistence.

Updated data from Cohort 2 (n=17 patients) is reported in FIG. 34 to FIG. 39. In comparison to Cohort 1 and an embodiment of the Gen 1 process, which showed a DCR of 64% and an overall response rate (ORR) of 29% (N=14), Cohort 2 and an embodiment of the Gen 2 process showed a DCR of 80% and an ORR of 40% (N=10).

Conclusions

Preliminary results from the existing data demonstrate comparable safety between Gen 1 and Gen 2 LN-144 TIL products. Administration of TILs manufactured with the Gen 2 process (process 2A, as described herein) leads to surprisingly increased clinical responses seen in advanced disease metastatic melanoma patients, all had progressed on anti-PD-1 and anti-CTLA-4 prior therapies. The DCR for cohort 2 was 78%.

Preliminary biomarker data is supportive of the cytolytic mechanism of action proposed for TIL therapy.

The embodiment of the Gen 2 manufacturing process described herein takes 22 days. This process significantly shortens the duration of time a patient has to wait to receive their TIL, offers flexibility in the timing of dosing the patients, and leads to a reduction of cost of manufacturing, while providing other advantages over prior approaches that allow for commercialization and registration with health regulatory agencies. Preliminary clinical data in metastatic melanoma using an embodiment of the Gen 2 manufacturing process also indicates a surprising improvement in clinical efficacy of the TILs, as measured by DCR, ORR, and other clinical responses, with a similar time to response and safety profile compared to TILs manufactured using the Gen 1 process.

REFERENCES

[1] Goff, et al. Randomized, Prospective Evaluation Comparing Intensity of Lymphodepletion Before Adoptive Transfer of Tumor-Infiltrating Lymphocytes for Patients With Metastatic Melanoma. *J Clin Oncol.* 2016 Jul. 10; 34(20): 2389-97.

[2] Sarnaik A, Kluger H, Chesney J, et al. Efficacy of single administration of tumor-infiltrating lymphocytes (TIL) in heavily pretreated patients with metastatic melanoma following checkpoint therapy. *J Clin Oncol.* 2017; 35 [suppl; abstr 3045].

Example 13: Historical Control Study

A historical control study may be used for comparison of the treatment outcomes in patients with double-refractory metastatic melanoma to the outcomes of TIL therapies disclosed herein, such as those therapies described in Example 2 and Example 3. In an embodiment, a patient treated with TIL therapies disclosed herein exhibits an improved response to the response expected from a historical control. In an embodiment, a patient treated with TIL therapies disclosed herein exhibits an improved response to the response expected from a historical control, wherein the improved response is determined as overall response rate. In an embodiment, a patient treated with TIL therapies disclosed herein exhibits an improved response to the response expected from a historical control, wherein the improved response is determined as overall response rate, wherein the improvement in overall response rate is at least 5%, at least 10%, at least 15%, at least 20%, at least 25%, or at least 50%. In an embodiment, a patient treated with TIL therapies disclosed herein exhibits an improved response to the response expected from a historical control, wherein the improved response is determined as duration of response. In an embodiment, a patient treated with TIL therapies disclosed herein exhibits an improved response to the response expected from a historical control, wherein the improved response is determined as duration of response, wherein the improvement in duration of response is at least 5%, at least 10%, at least 15%, at least 20%, at least 25%, or at least 50%.

The historical control study to determine the response of double-refractory patients to other therapies may be performed using data obtained from the treatment records of metastatic melanoma patients. Patients must be exposed to 3 or more lines of therapies for melanoma after the initial diagnosis of melanoma. Lines of systemic therapies are counted per the following rules and start and stop dates of each therapy are considered:

All agents received within 28 days of the first line (1 L) start constituted the 1 L regimen, and could include a single agent or combine multiple agents; 1 L end corresponded to either the first gap of >90 days in the all 1 L agents or the initiation of a new agent that was not part of 1 L (i.e., switch to a new line);

Subsequent lines of therapy are identified as the earliest of (a) initiation of an agent not in the previous treatment regimen (after the initial 28 day period to identify 1 L regimen), or (b) initiation of any agent after a gap of >90 days in the previous treatment. Regimens used in subsequent lines were identified based on all agents received within 28 days of the start of the respective line of therapy In general, ipilumimab and nivolumab administered as a combination are considered to be one therapy and BRAF and MEK inhibitors administered in combination (e.g., dabrafenib and trametinib) considered to be one therapy.

All patients must have been treated with at least one anti-PD-1 (or anti-PD-L1) therapy and failed (i.e., are refractory or relapsed). Availability of the scan date that led to disease progression if the line of therapy contains anti-PD1 therapy is preferred. For the last therapy on record (3rd or later), an overall response per visit and date of either disease progression or death (if applicable) are required.

For the last line of therapy on record, either i) target and non-target lesions measures per each assessment, or ii) overall response per visit by RECIST is required.

Certain baseline disease status and baseline characteristics before the initiation of the last therapy on record are required, to allow for evaluation of whether these patients meet the similar eligibility criteria for other studies described herein (including in Example 2 and Example 3).

I claim:

1. A method of treating double-refractory metastatic melanoma in a patient in need thereof, the method comprising administering a therapeutically effective population of tumor infiltrating lymphocytes (TILs) to the patient, wherein the metastatic melanoma is resistant to a) a PD-1 inhibitor or a PD-L1 inhibitor, and b) a BRAF inhibitor or a combination of a BRAF inhibitor and a MEK inhibitor.

2. The method of claim 1, wherein the double-refractory metastatic melanoma is a cutaneous double-refractory metastatic melanoma.

3. The method of claim 1, wherein the double-refractory metastatic melanoma is refractory to at least two prior systemic treatment courses, not including neo-adjuvant or adjuvant therapies.

4. The method of claim 1, wherein the double-refractory metastatic melanoma is refractory to pembrolizumab.

5. The method of claim 1, wherein the double-refractory metastatic melanoma is refractory to nivolumab.

6. The method of claim 1, wherein the double-refractory metastatic melanoma is refractory to a BRAF inhibitor.

7. The method of claim 1, wherein the double-refractory metastatic melanoma is refractory to a PD-L1 inhibitor.

8. The method of claim 7, wherein the PD-L1 inhibitor is selected from the group consisting of avelumab, atezolizumab, and durvalumab.

9. The method of claim 1, wherein the double-refractory metastatic melanoma is refractory to a combination of a BRAF inhibitor and a MEK inhibitor.

10. The method of claim 9, wherein the BRAF inhibitor is dabrafenib or a pharmaceutically-acceptable salt thereof and the MEK inhibitor is trametinib or a pharmaceutically-acceptable salt or solvate thereof.

11. The method of claim 1, wherein the PD-1 or PD-L1 inhibitor is selected from the group consisting of nivolumab, pembrolizumab, avelumab, atezolizumab, and durvalumab.

12. The method of claim 1, wherein the patient does not possess a BRAF mutation.

13. The method of claim 11, wherein the patient has received at most 4 doses of nivolumab prior to receiving the therapeutically effective population of TILs.

14. The method of claim 1, wherein the BRAF inhibitor is selected from the group consisting of vemurafenib, dabrafenib, and pharmaceutically-acceptable salts thereof.

15. The method of claim 1, wherein the MEK inhibitor is selected from the group consisting of trametinib, cobimetinib, and pharmaceutically-acceptable salts or solvates thereof.

* * * * *

SEQUENCE LISTING

```
<160> NUMBER OF SEQ ID NOS: 126

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
```

145                 150                 155                 160
Ser Trp Thr Asp Gln Asp Ser Lys Asp Ser Thr Tyr Ser Met Ser Ser
                    165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

```
Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125
```

```
Leu Cys Phe Leu Lys Arg Leu Leu Gln Glu Ile Lys Thr Cys Trp Asn
            130                 135                 140
Lys Ile Leu Met Gly Thr Lys Glu His
145                 150
```

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

```
Met Asn Trp Val Asn Val Ile Ser Asp Leu Lys Lys Ile Glu Asp Leu
1               5                   10                  15
Ile Gln Ser Met His Ile Asp Ala Thr Leu Tyr Thr Glu Ser Asp Val
            20                  25                  30
His Pro Ser Cys Lys Val Thr Ala Met Lys Cys Phe Leu Leu Glu Leu
        35                  40                  45
Gln Val Ile Ser Leu Glu Ser Gly Asp Ala Ser Ile His Asp Thr Val
    50                  55                  60
Glu Asn Leu Ile Ile Leu Ala Asn Asn Ser Leu Ser Ser Asn Gly Asn
65                  70                  75                  80
Val Thr Glu Ser Gly Cys Lys Glu Cys Glu Glu Leu Glu Glu Lys Asn
                85                  90                  95
Ile Lys Glu Phe Leu Gln Ser Phe Val His Ile Val Gln Met Phe Ile
            100                 105                 110
Asn Thr Ser
        115
```

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

```
Met Gln Asp Arg His Met Ile Arg Met Arg Gln Leu Ile Asp Ile Val
1               5                   10                  15
Asp Gln Leu Lys Asn Tyr Val Asn Asp Leu Val Pro Glu Phe Leu Pro
            20                  25                  30
Ala Pro Glu Asp Val Glu Thr Asn Cys Glu Trp Ser Ala Phe Ser Cys
        35                  40                  45
Phe Gln Lys Ala Gln Leu Lys Ser Ala Asn Thr Gly Asn Asn Glu Arg
    50                  55                  60
Ile Ile Asn Val Ser Ile Lys Lys Leu Lys Arg Lys Pro Pro Ser Thr
65                  70                  75                  80
Asn Ala Gly Arg Arg Gln Lys His Arg Leu Thr Cys Pro Ser Cys Asp
                85                  90                  95
Ser Tyr Glu Lys Lys Pro Pro Lys Glu Phe Leu Glu Arg Phe Lys Ser
            100                 105                 110
Leu Leu Gln Lys Met Ile His Gln His Leu Ser Ser Arg Thr His Gly
        115                 120                 125
Ser Glu Asp Ser
    130
```

-continued

```
<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 10
<211> LENGTH: 256
<212> TYPE: PRT
<213> ORGANISM: Artificial Sequence
<220> FEATURE:
<223> OTHER INFORMATION: murine 4-1BB Tumor necrosis factor receptor
      superfamily, member 9 (Mus musculus)

<400> SEQUENCE: 10

Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
```

```
                 50                  55                  60
Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
                100                 105                 110

Lys Gln Gly Cys Lys Thr Cys Ser Leu Gly Thr Phe Asn Asp Gln Asn
                115                 120                 125

Gly Thr Gly Val Cys Arg Pro Trp Thr Asn Cys Ser Leu Asp Gly Arg
        130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
                180                 185                 190

Leu Thr Ser Ala Leu Leu Leu Ala Leu Ile Phe Ile Thr Leu Leu Phe
                195                 200                 205

Ser Val Leu Lys Trp Ile Arg Lys Lys Phe Pro His Ile Phe Lys Gln
        210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Gly Tyr Glu Leu
                245                 250                 255

<210> SEQ ID NO 11
<211> LENGTH: 441
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
  1               5                  10                  15

Ser Leu Arg Ile Ser Cys Lys Gly Ser Gly Tyr Ser Phe Ser Thr Tyr
                 20                  25                  30

Trp Ile Ser Trp Val Arg Gln Met Pro Gly Lys Gly Leu Glu Trp Met
                 35                  40                  45

Gly Lys Ile Tyr Pro Gly Asp Ser Tyr Thr Asn Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
               165                 170                 175
Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
            290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
            435                 440

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
```

```
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab

<400> SEQUENCE: 13

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab

<400> SEQUENCE: 14

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45
```

```
Gln Asp Lys Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105

<210> SEQ ID NO 15
<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

Ser Thr Tyr Trp Ile Ser
1               5

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab

<400> SEQUENCE: 16

Lys Ile Tyr Pro Gly Asp Ser Tyr Thr Asn Tyr Ser Pro Ser Phe Gln
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

Arg Gly Tyr Gly Ile Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

Ser Gly Asp Asn Ile Gly Asp Gln Tyr Ala His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: light chain CDR2 for utomilumab

<400> SEQUENCE: 19

Gln Asp Lys Asn Arg Pro Ser
1               5
```

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1               5                   10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 22
<211> LENGTH: 216
<212> TYPE: PRT
<213> ORGANISM: Artificial Sequence
<220> FEATURE:
<223> OTHER INFORMATION: light chain for urelumab

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

```
<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23
```

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro
        115                 120

```
<210> SEQ ID NO 24
<211> LENGTH: 110
<212> TYPE: PRT
<213> ORGANISM: Artificial Sequence
<220> FEATURE:
<223> OTHER INFORMATION: variable light chain for urelumab

<400> SEQUENCE: 24
```

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln
            100                 105                 110

```
<210> SEQ ID NO 25
<211> LENGTH: 5
<212> TYPE: PRT
<213> ORGANISM: Artificial Sequence
<220> FEATURE:
<223> OTHER INFORMATION: heavy chain CDR1 for urelumab

<400> SEQUENCE: 25
```

Gly Tyr Tyr Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: light chain CDR1 for urelumab

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1               5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1               5                   10

<210> SEQ ID NO 31
<211> LENGTH: 230
<212> TYPE: PRT
<213> ORGANISM: Artificial Sequence
<220> FEATURE:
<223> OTHER INFORMATION: Fc domain

<400> SEQUENCE: 31

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp

```
            20                  25                  30
Thr Leu Met Ile Ser Arg Thr Pro Glu Val Thr Cys Val Val Asp
         35                  40                  45
Val Ser His Glu Asp Pro Glu Val Lys Phe Asn Trp Tyr Val Asp Gly
 50                  55                  60
Val Glu Val His Asn Ala Lys Thr Lys Pro Arg Glu Glu Gln Tyr Asn
 65                  70                  75                  80
Ser Thr Tyr Arg Val Val Ser Val Leu Thr Val Leu His Gln Asp Trp
                 85                  90                  95
Leu Asn Gly Lys Glu Tyr Lys Cys Lys Val Ser Asn Lys Ala Leu Pro
             100                 105                 110
Ala Pro Ile Glu Lys Thr Ile Ser Lys Ala Lys Gly Gln Pro Arg Glu
         115                 120                 125
Pro Gln Val Tyr Thr Leu Pro Pro Ser Arg Glu Glu Met Thr Lys Asn
     130                 135                 140
Gln Val Ser Leu Thr Cys Leu Val Lys Gly Phe Tyr Pro Ser Asp Ile
145                 150                 155                 160
Ala Val Glu Trp Glu Ser Asn Gly Gln Pro Glu Asn Asn Tyr Lys Thr
                 165                 170                 175
Thr Pro Pro Val Leu Asp Ser Asp Gly Ser Phe Leu Tyr Ser Lys
             180                 185                 190
Leu Thr Val Asp Lys Ser Arg Trp Gln Gln Gly Asn Val Phe Ser Cys
         195                 200                 205
Ser Val Met His Glu Ala Leu His Asn His Tyr Thr Gln Lys Ser Leu
     210                 215                 220
Ser Leu Ser Pro Gly Lys
225                 230

<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33

Gly Gly Ser Gly Ser Ser Lys Ser Cys Asp Lys Thr His Thr Cys Pro
1               5                   10                  15

Pro Cys Pro Ala Pro Glu
            20

<210> SEQ ID NO 34
<211> LENGTH: 27
<212> TYPE: PRT
<213> ORGANISM: Artificial Sequence
<220> FEATURE:
```

<223> OTHER INFORMATION: linker

<400> SEQUENCE: 34

Gly Gly Pro Gly Ser Ser Ser Ser Ser Ser Lys Ser Cys Asp Lys
1               5                   10                  15
Thr His Thr Cys Pro Pro Cys Pro Ala Pro Glu
            20                  25

<210> SEQ ID NO 35
<211> LENGTH: 27
<212> TYPE: PRT
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Lys Ser Cys Asp Lys
1               5                   10                  15
Thr His Thr Cys Pro Pro Cys Pro Ala Pro Glu
            20                  25

<210> SEQ ID NO 36
<211> LENGTH: 29
<212> TYPE: PRT
<213> ORGANISM: Artificial Sequence
<220> FEATURE:
<223> OTHER INFORMATION: linker

<400> SEQUENCE: 36

Gly Gly Pro Gly Ser Ser Ser Ser Ser Ser Ser Lys Ser Cys
1               5                   10
Asp Lys Thr His Thr Cys Pro Pro Cys Pro Ala Pro Glu
            20                  25

<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Lys Ser Cys
1               5                   10
Asp Lys Thr His Thr Cys Pro Pro Cys Pro Ala Pro Glu
            20                  25

<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38

Gly Gly Pro Gly Ser Ser Gly Ser Gly Ser Ser Asp Lys Thr His Thr
1               5                   10                  15
Cys Pro Pro Cys Pro Ala Pro Glu
            20

<210> SEQ ID NO 39
<211> LENGTH: 23
<212> TYPE: PRT
<213> ORGANISM: Artificial Sequence

```
<220> FEATURE:
<223> OTHER INFORMATION: linker

<400> SEQUENCE: 39

Gly Gly Pro Gly Ser Gly Ser Gly Ser Asp Lys Thr His Thr Cys
1               5                   10                  15

Pro Pro Cys Pro Ala Pro Glu
            20

<210> SEQ ID NO 40
<211> LENGTH: 21
<212> TYPE: PRT
<213> ORGANISM: Artificial Sequence
<220> FEATURE:
<223> OTHER INFORMATION: linker

<400> SEQUENCE: 40

Gly Gly Pro Ser Ser Gly Ser Asp Lys Thr His Thr Cys Pro Pro
1               5                   10                  15

Cys Pro Ala Pro Glu
            20

<210> SEQ ID NO 41
<211> LENGTH: 25
<212> TYPE: PRT
<213> ORGANISM: Artificial Sequence
<220> FEATURE:
<223> OTHER INFORMATION: linker

<400> SEQUENCE: 41

Gly Gly Ser Ser Ser Ser Ser Ser Ser Gly Ser Asp Lys Thr His
1               5                   10                  15

Thr Cys Pro Pro Cys Pro Ala Pro Glu
            20                  25

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140
```

Glu Pro Gln Val Tyr Thr Leu Pro Pro Ser Arg Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Gly Ser Gly Ser Gly Ser Gly Ser Gly Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: linker

<400> SEQUENCE: 44

Ser Ser Ser Ser Ser Ser Gly Ser Gly Ser Gly Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

Ser Ser Ser Ser Ser Ser Gly Ser Gly Ser Gly Ser Gly Ser Gly Ser
1               5                   10                  15

<210> SEQ ID NO 46
<211> LENGTH: 254
<212> TYPE: PRT
<213> ORGANISM: Artificial Sequence
<220> FEATURE:
<223> OTHER INFORMATION: 4-1BBL

<400> SEQUENCE: 46

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

```
Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

Leu Arg Gln Gly Met Phe Ala Gln Leu Val Ala Gln Asn Val Leu Leu
1               5                   10                  15

Ile Asp Gly Pro Leu Ser Trp Tyr Ser Asp Pro Gly Leu Ala Gly Val
            20                  25                  30

Ser Leu Thr Gly Gly Leu Ser Tyr Lys Glu Asp Thr Lys Glu Leu Val
        35                  40                  45

Val Ala Lys Ala Gly Val Tyr Tyr Val Phe Phe Gln Leu Glu Leu Arg
    50                  55                  60

Arg Val Val Ala Gly Glu Gly Ser Gly Ser Val Ser Leu Ala Leu His
65                  70                  75                  80

Leu Gln Pro Leu Arg Ser Ala Ala Gly Ala Ala Ala Leu Ala Leu Thr
                85                  90                  95

Val Asp Leu Pro Pro Ala Ser Ser Glu Ala Arg Asn Ser Ala Phe Gly
            100                 105                 110

Phe Gln Gly Arg Leu Leu His Leu Ser Ala Gly Gln Arg Leu Gly Val
        115                 120                 125

His Leu His Thr Glu Ala Arg Ala Arg His Ala Trp Gln Leu Thr Gln
    130                 135                 140

Gly Ala Thr Val Leu Gly Leu Phe Arg Val Thr Pro Glu Ile Pro Ala
145                 150                 155                 160
```

```
<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser
        115

<210> SEQ ID NO 49
<211> LENGTH: 107
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys
            100                 105

<210> SEQ ID NO 50
<211> LENGTH: 119
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50
```

-continued

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Phe Thr Ala Arg Gly Phe Ala Tyr Trp Gly Gln Gly
            100                 105                 110

Thr Leu Val Thr Val Ser Ala
        115
```

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

```
Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
            85                  90                  95

Thr Phe Gly Gly Gly Thr Lys Leu Glu Ile Lys Arg
            100                 105
```

<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Ser Trp Val Arg Gln Ala Pro Gly Lys Gly Leu
    50                  55                  60

Glu Trp Val Ala Asp Ile Lys Asn Asp Gly Ser Tyr Thr Asn Tyr Ala
65                  70                  75                  80
```

```
Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr
        115                 120

<210> SEQ ID NO 53
<211> LENGTH: 109
<212> TYPE: PRT
<213> ORGANISM: Artificial Sequence
<220> FEATURE:
<223> OTHER INFORMATION: variable light chain for H39E3-2

<400> SEQUENCE: 53

Met Glu Ala Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Ser Ser Gly Asn Gln Lys Asn Tyr Leu Trp Tyr Gln Gln Lys
    50                  55                  60

Pro Gly Gln Pro Pro Lys Leu Ile Tyr Tyr Ala Ser Thr Arg Gln
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala
            100                 105

<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
```

```
                145                 150                 155                 160
        Ser Ser Asp Ala Ile Cys Glu Asp Arg Asp Pro Pro Ala Thr Gln Pro
                        165                 170                 175

Gln Glu Thr Gln Gly Pro Pro Ala Arg Pro Ile Thr Val Gln Pro Thr
                        180                 185                 190

Glu Ala Trp Pro Arg Thr Ser Gln Gly Pro Ser Thr Arg Pro Val Glu
                        195                 200                 205

Val Pro Gly Gly Arg Ala Val Ala Ala Ile Leu Gly Leu Gly Leu Val
                        210                 215                 220

Leu Gly Leu Leu Gly Pro Leu Ala Ile Leu Leu Ala Leu Tyr Leu Leu
        225                 230                 235                 240

Arg Arg Asp Gln Arg Leu Pro Pro Asp Ala His Lys Pro Pro Gly Gly
                        245                 250                 255

Gly Ser Phe Arg Thr Pro Ile Gln Glu Glu Gln Ala Asp Ala His Ser
                        260                 265                 270

Thr Leu Ala Lys Ile
                        275

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

Met Tyr Val Trp Val Gln Gln Pro Thr Ala Leu Leu Leu Leu Gly Leu
        1               5                   10                  15

Thr Leu Gly Val Thr Ala Arg Arg Leu Asn Cys Val Lys His Thr Tyr
                        20                  25                  30

Pro Ser Gly His Lys Cys Cys Arg Glu Cys Gln Pro Gly His Gly Met
                        35                  40                  45

Val Ser Arg Cys Asp His Thr Arg Asp Thr Leu Cys His Pro Cys Glu
                        50                  55                  60

Thr Gly Phe Tyr Asn Glu Ala Val Asn Tyr Asp Thr Cys Lys Gln Cys
        65                  70                  75                  80

Thr Gln Cys Asn His Arg Ser Gly Ser Glu Leu Lys Gln Asn Cys Thr
                        85                  90                  95

Pro Thr Gln Asp Thr Val Cys Arg Cys Arg Pro Gly Thr Gln Pro Arg
                        100                 105                 110

Gln Asp Ser Gly Tyr Lys Leu Gly Val Asp Cys Val Pro Cys Pro Pro
                        115                 120                 125

Gly His Phe Ser Pro Gly Asn Asn Gln Ala Cys Lys Pro Trp Thr Asn
                        130                 135                 140

Cys Thr Leu Ser Gly Lys Gln Thr Arg His Pro Ala Ser Asp Ser Leu
        145                 150                 155                 160

Asp Ala Val Cys Glu Asp Arg Ser Leu Leu Ala Thr Leu Leu Trp Glu
                        165                 170                 175

Thr Gln Arg Pro Thr Phe Arg Pro Thr Thr Val Gln Ser Thr Thr Val
                        180                 185                 190

Trp Pro Arg Thr Ser Glu Leu Pro Ser Pro Thr Leu Val Thr Pro
                        195                 200                 205

Glu Gly Pro Ala Phe Ala Val Leu Leu Gly Leu Gly Leu Gly Leu Leu
                        210                 215                 220

Ala Pro Leu Thr Val Leu Leu Ala Leu Tyr Leu Leu Arg Lys Ala Trp
```

-continued

```
                225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
                260                 265                 270

<210> SEQ ID NO 56
<211> LENGTH: 451
<212> TYPE: PRT
<213> ORGANISM: Artificial Sequence
<220> FEATURE:
<223> OTHER INFORMATION: heavy chain for tavolixizumab

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                325                 330                 335
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr
        115

<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab

<400> SEQUENCE: 59

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105

<210> SEQ ID NO 60
<211> LENGTH: 9
<212> TYPE: PRT
<213> ORGANISM: Artificial Sequence
<220> FEATURE:
<223> OTHER INFORMATION: heavy chain CDR1 for tavolixizumab

<400> SEQUENCE: 60

Gly Ser Phe Ser Ser Gly Tyr Trp Asn
1               5

<210> SEQ ID NO 61
```

```
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1               5

<210> SEQ ID NO 64
<211> LENGTH: 11
<212> TYPE: PRT
<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1               5                   10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1               5

<210> SEQ ID NO 66
<211> LENGTH: 444
<212> TYPE: PRT
<213> ORGANISM: Artificial Sequence
<220> FEATURE:
<223> OTHER INFORMATION: heavy chain for 11D4

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
        35                  40                  45
Ser Tyr Ile Ser Ser Ser Ser Thr Ile Asp Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Asp Glu Asp Thr Ala Val Tyr Tyr Cys
                85                  90                  95
Ala Arg Glu Ser Gly Trp Tyr Leu Phe Asp Tyr Trp Gly Gln Gly Thr
               100                 105                 110
Leu Val Thr Val Ser Ser Ala Ser Thr Lys Gly Pro Ser Val Phe Pro
               115                 120                 125
Leu Ala Pro Cys Ser Arg Ser Thr Ser Glu Ser Thr Ala Ala Leu Gly
               130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
               165                 170                 175
Ser Ser Gly Leu Tyr Ser Leu Ser Ser Val Val Thr Val Pro Ser Ser
               180                 185                 190
Asn Phe Gly Thr Gln Thr Tyr Thr Cys Asn Val Asp His Lys Pro Ser
               195                 200                 205
Asn Thr Lys Val Asp Lys Thr Val Glu Arg Lys Cys Cys Val Glu Cys
               210                 215                 220
Pro Pro Cys Pro Ala Pro Pro Val Ala Gly Pro Ser Val Phe Leu Phe
225                 230                 235                 240
Pro Pro Lys Pro Lys Asp Thr Leu Met Ile Ser Arg Thr Pro Glu Val
               245                 250                 255
Thr Cys Val Val Val Asp Val Ser His Glu Asp Pro Glu Val Gln Phe
               260                 265                 270
Asn Trp Tyr Val Asp Gly Val Glu Val His Asn Ala Lys Thr Lys Pro
               275                 280                 285
Arg Glu Glu Gln Phe Asn Ser Thr Phe Arg Val Val Ser Val Leu Thr
290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
               325                 330                 335
Lys Gly Gln Pro Arg Glu Pro Gln Val Tyr Thr Leu Pro Pro Ser Arg
               340                 345                 350
Glu Glu Met Thr Lys Asn Gln Val Ser Leu Thr Cys Leu Val Lys Gly
               355                 360                 365
Phe Tyr Pro Ser Asp Ile Ala Val Glu Trp Glu Ser Asn Gly Gln Pro
               370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
               405                 410                 415
Gly Asn Val Phe Ser Cys Ser Val Met His Glu Ala Leu His Asn His
               420                 425                 430
Tyr Thr Gln Lys Ser Leu Ser Leu Ser Pro Gly Lys
               435                 440
```

<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95
```

```
Ala Arg Glu Ser Gly Trp Tyr Leu Phe Asp Tyr Trp Gly Gln Gly Thr
                100                 105                 110
Leu Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
                100                 105

<210> SEQ ID NO 70
<211> LENGTH: 5
<212> TYPE: PRT
<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5
```

-continued

```
<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1               5

<210> SEQ ID NO 76
<211> LENGTH: 450
<212> TYPE: PRT
<213> ORGANISM: Artificial Sequence
<220> FEATURE:
<223> OTHER INFORMATION: heavy chain for 18D8

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
               165                 170                 175
Phe Pro Ala Val Leu Gln Ser Ser Gly Leu Tyr Ser Leu Ser Ser Val
                180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Thr
                    85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
        210
```

<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120
```

<210> SEQ ID NO 79
<211> LENGTH: 106
<212> TYPE: PRT
<213> ORGANISM: Artificial Sequence
<220> FEATURE:
<223> OTHER INFORMATION: light chain variable region for 18D8

<400> SEQUENCE: 79

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105

<210> SEQ ID NO 80
<211> LENGTH: 5
<212> TYPE: PRT
<213> ORGANISM: Artificial Sequence
<220> FEATURE:
<223> OTHER INFORMATION: heavy chain CDR1 for 18D8

<400> SEQUENCE: 80

Asp Tyr Ala Met His
 1               5

<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81

Gly Ile Ser Trp Asn Ser Gly Ser Ile Gly Tyr Ala Asp Ser Val Lys
 1               5                  10                  15

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
 1               5                  10                  15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala
 1               5                  10

<210> SEQ ID NO 84
<211> LENGTH: 7
<212> TYPE: PRT
<213> ORGANISM: Artificial Sequence
<220> FEATURE:
<223> OTHER INFORMATION: light chain CDR2 for 18D8

<400> SEQUENCE: 84
```

Asp Ala Ser Asn Arg Ala Thr
1               5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr
1               5

<210> SEQ ID NO 86
<211> LENGTH: 120
<212> TYPE: PRT
<213> ORGANISM: Artificial Sequence
<220> FEATURE:
<223> OTHER INFORMATION: heavy chain variable region for Hu119-122

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys

<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

Ser His Asp Met Ser
1               5

<210> SEQ ID NO 89
<211> LENGTH: 17
<212> TYPE: PRT
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1               5                   10                  15

Arg

<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr
1               5                   10

<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

Arg Ala Ser Lys Ser Val Ser Thr Ser Gly Tyr Ser Tyr Met His
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

Leu Ala Ser Asn Leu Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: light chain CDR3 for Hu119-122

<400> SEQUENCE: 93

```
Gln His Ser Arg Glu Leu Pro Leu Thr
1               5
```

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120
```

<210> SEQ ID NO 95
<211> LENGTH: 107
<212> TYPE: PRT
<213> ORGANISM: Artificial Sequence
<220> FEATURE:
<223> OTHER INFORMATION: light chain variable region for Hu106-222

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105
```

<210> SEQ ID NO 96
<211> LENGTH: 5
<212> TYPE: PRT
<213> ORGANISM: Artificial Sequence
<220> FEATURE:
<223> OTHER INFORMATION: heavy chain CDR1 for Hu106-222

<400> SEQUENCE: 96

Asp Tyr Ser Met His

```
<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

Trp Ile Asn Thr Glu Thr Gly Glu Pro Thr Tyr Ala Asp Asp Phe Lys
1               5                   10                  15
Gly

<210> SEQ ID NO 98
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr
1               5

<210> SEQ ID NO 102
<211> LENGTH: 183
<212> TYPE: PRT
<213> ORGANISM: Artificial Sequence
<220> FEATURE:
<223> OTHER INFORMATION: OX40L

<400> SEQUENCE: 102
```

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
            130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 103
<211> LENGTH: 131
<212> TYPE: PRT
<213> ORGANISM: Artificial Sequence
<220> FEATURE:
<223> OTHER INFORMATION: OX40L soluble domain

<400> SEQUENCE: 103

```
Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
            20                  25                  30

Ile Met Lys Val Gln Asn Asn Ser Val Ile Ile Asn Cys Asp Gly Phe
            35                  40                  45

Tyr Leu Ile Ser Leu Lys Gly Tyr Phe Ser Gln Glu Val Asn Ile Ser
50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Asp Phe His
            100                 105                 110

Val Asn Gly Gly Glu Leu Ile Leu Ile His Gln Asn Pro Gly Glu Phe
            115                 120                 125

Cys Val Leu
    130
```

<210> SEQ ID NO 104
<211> LENGTH: 128
<212> TYPE: PRT
<213> ORGANISM: Artificial Sequence
<220> FEATURE:

<223> OTHER INFORMATION: OX40L soluble domain (alternative)

<400> SEQUENCE: 104

Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
    50                  55                  60

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125

<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120

<210> SEQ ID NO 106
<211> LENGTH: 108
<212> TYPE: PRT
<213> ORGANISM: Artificial Sequence
<220> FEATURE:
<223> OTHER INFORMATION: variable light chain for 008

<400> SEQUENCE: 106

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser

```
                    35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105
```

<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Thr Met Asn Trp Val Arg Gln Ala Pro Gly Lys Gly Leu Glu Trp Val
            35                  40                  45

Ser Ser Ile Ser Gly Gly Ser Thr Tyr Tyr Ala Asp Ser Arg Lys Gly
        50                  55                  60

Arg Phe Thr Ile Ser Arg Asp Asn Ser Lys Thr Leu Tyr Leu Gln
65                  70                  75                  80

Met Asn Asn Leu Arg Ala Glu Asp Thr Ala Val Tyr Tyr Cys Ala Arg
                85                  90                  95

Asp Arg Tyr Phe Arg Gln Gln Asn Ala Phe Asp Tyr Trp Gly Gln Gly
            100                 105                 110

Thr Leu Val Thr Val Ser Ser Ala
        115                 120
```

<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108

```
Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Ala Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105
```

```
<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105

<210> SEQ ID NO 111
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
```

```
                  20                  25                  30
Ala Met His Trp Val Arg Gln Ala Pro Gly Lys Gly Leu Glu Trp Val
             35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
                100                 105                 110

Gly Thr Leu Val Thr Val Ser Ser
            115                 120

<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105

<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95
```

Ala Asn Tyr Tyr Gly Ser Ser Leu Ser Met Asp Tyr Trp Gly Gln Gly
            100                 105                 110

Thr Ser Val Thr Val Ser Ser
        115

<210> SEQ ID NO 114
<211> LENGTH: 108
<212> TYPE: PRT
<213> ORGANISM: Artificial Sequence
<220> FEATURE:
<223> OTHER INFORMATION: light chain variable region

<400> SEQUENCE: 114

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 115
<211> LENGTH: 121
<212> TYPE: PRT
<213> ORGANISM: Artificial Sequence
<220> FEATURE:
<223> OTHER INFORMATION: heavy chain variable region

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 116
<211> LENGTH: 108
<212> TYPE: PRT
<213> ORGANISM: Artificial Sequence
<220> FEATURE:
<223> OTHER INFORMATION: light chain variable region -continued

```
<400> SEQUENCE: 116

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120

<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 118

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
```

```
            50                  55                  60
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Asn Pro Tyr Tyr Asp Tyr Val Ser Tyr Tyr Ala Met Asp Tyr Trp
                100                 105                 110

Gly Gln Gly Thr Thr Val Thr Val Ser Ser
            115                 120

<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 119

Asp Ile Val Met Thr Gln Ser His Lys Phe Met Ser Thr Ser Val Arg
  1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Leu Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Arg
                 85                  90                  95

Thr Phe Gly Gly Gly Thr Lys Leu Glu Ile Lys
                100                 105

<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 120

Asp Ile Val Met Thr Gln Ser His Lys Phe Met Ser Thr Ser Val Arg
  1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Leu Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Arg
                 85                  90                  95

Thr Phe Gly Gly Gly Thr Lys Leu Glu Ile Lys
                100                 105
```

```
<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 121
```

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120

```
<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 122
```

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

```
<210> SEQ ID NO 123
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 123
```

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80
```

```
Tyr Ala Glu Ser Val Asn Gly Arg Phe Thr Ile Ser Arg Asp Asp Ser
                85              90                  95

Lys Ser Ser Val Tyr Leu Gln Met Asn Ser Leu Arg Ala Glu Asp Thr
            100             105                 110

Gly Ile Tyr Tyr Cys Thr Trp Gly Glu Val Phe Tyr Phe Asp Tyr Trp
        115             120                 125

Gly Gln Gly Thr Thr Leu Thr Val Ser Ser
    130             135

<210> SEQ ID NO 126
<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
                20                  25                  30

Ala Ser Leu Gly Gly Lys Val Thr Ile Thr Cys Lys Ser Ser Gln Asp
            35                  40                  45

Ile Asn Lys Tyr Ile Ala Trp Tyr Gln His Lys Pro Gly Lys Gly Pro
        50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125
```